(12) United States Patent
Ferrari et al.

(10) Patent No.: US 6,184,348 B1
(45) Date of Patent: *Feb. 6, 2001

US006184348B1

(54) FUNCTIONAL RECOMBINANTLY PREPARED SYNTHETIC PROTEIN POLYMER

(75) Inventors: Franco A. Ferrari, La Jolla; Joseph Cappello, San Diego, both of CA (US)

(73) Assignee: Protein Polymer Technologies, San Diego, CA (US)

( * ) Notice: Under 35 U.S.C. 154(b), the term of this patent shall be extended for 0 days.

This patent is subject to a terminal disclaimer.

(21) Appl. No.: 08/478,029

(22) Filed: Jun. 7, 1995

Related U.S. Application Data

(60) Division of application No. 07/609,716, filed on Nov. 6, 1990, now Pat. No. 5,514,581, which is a continuation-in-part of application No. 07/269,429, filed on Nov. 9, 1988, now abandoned, which is a continuation-in-part of application No. 07/114,618, filed on Oct. 29, 1997, now Pat. No. 5,243,038, which is a continuation-in-part of application No. 06/927,258, filed on Nov. 4, 1986, now abandoned.

(51) Int. Cl.[7] .................... C07K 14/00; C12N 15/11; C12N 15/00
(52) U.S. Cl. .................... 530/350; 530/353; 435/69.1; 935/10; 935/60
(58) Field of Search ................... 435/69.1, 320.1, 435/172.3; 530/350, 353; 536/23.1, 23.4; 935/10, 60

(56) References Cited

U.S. PATENT DOCUMENTS

| | | | |
|---|---|---|---|
| 4,132,746 | 1/1979 | Urry et al. | 525/432 |
| 4,187,852 | 2/1980 | Urry et al. | 600/36 |
| 4,474,851 | 10/1984 | Urry | 428/373 |
| 4,500,700 | 2/1985 | Urry | 528/328 |
| 4,589,882 | 5/1986 | Urry | 623/11 |
| 5,149,657 | 9/1992 | Maugh et al. | 435/320.1 |

FOREIGN PATENT DOCUMENTS 2162190  1/1986 (GB).

OTHER PUBLICATIONS

Mita et al., "Specific Codon Usage Pattern and Its Implication on the Secondary Structure of Silk Fibroin mRNA." J. Mol. Biol. vol. 203:917–925, 1988.*

Raju et al "Primary Structures of Bovine Elastin a, b, and c, Deduced from the Sequences of cDNA Clone." J. of Biol. Chem. vol. 262(12):5755–5762, Apr. 25, 1987*
Tsujimoto et al." The DNA Sequence of *Bombyx mori* Fibroin Gene Including the 5' Flanking, mRNA Coding, Entire Interviewing and Fibroin Protein Coding Regions" Cell vol. 18. 591–600, Oct. 1979.*
Schwarz et al., "Strucutre of Mouse Type IV Collagen" Eur J. Biochem. vol. 157:49–56, 1986.*
Kempe et al., Gene (1985), 39:239–245.
Nakajima et al., Chem. (1980), 93:95638.
Bressan et al., Biochemistry (1987), 26:1497–1503.
Shen, Proc. Nat. Acad. Sci. USA (1984), 81:4627–4631.
Doel et al., Nucleic Acids Res. (1980), 8:4575–4592.
Hartley et al., Gene (1981), 13:347–353.
Gage et al., J. Biol. Chem. (1980), 255:9444–9450.
Gupta et al., Bio/Technology (1983), 1:602–609.
Sadler et al., Gene (1980), 8:279–300.
Jarman et al., World Biotech Rep. (1985), 1:505–512.
Dixon, Bio/Technology (1985), 3:671.
Lotz et al., J. Mol. Biol. (1982), 156:345–357.
Allbertini et al., Cell (1982), 29:319–328.
Bell et al., Int. J. Peptide Protein Res. (1974), 6:155–156.
Urry et al., Protein Elasticity of Sequential Polypeptides (1984), 3:403–436.
Foster et al., "Isolation and Amino Acid Sequences of Tropoelastin Peptides", J. Biol. Chem. (1979), 248:2876–2879.
Sandberg et al., "Elastin Structure, Biosynthesis and Relation to Disease Sates", N. Engl. J. Med. (1981), 304:566–579.

* cited by examiner

Primary Examiner—Remy Yucel
Assistant Examiner—Sean McGarry
(74) Attorney, Agent, or Firm—Richard F. Trecartin; Flehr Hobach Test Albritton & Herbert LLP

(57) ABSTRACT

Novel polymers are provided which are produced by recombinant techniques. The polymers are characterized by having a small repeating sequence which provides for strands capable of associating, resulting in useful structural characteristics, where the strands are joined by turns or loops which are flexible and available for interaction with the environment. Specifically, repeating groups of naturally occurring proteins such as silk are modified by introduction of an amino-acid sequence at a site which provides for a turn between strands to provide for readily available oligopeptides capable of interacting with molecules in the environment.

14 Claims, No Drawings

FUNCTIONAL RECOMBINANTLY PREPARED SYNTHETIC PROTEIN POLYMER

CROSS-REFERENCE TO RELATED APPLICATIONS

This is a division, of application Ser. No. 07/609,716 filed Nov. 6, 1990, and now U.S. Pat. No. 5,514,581, which is a continuation-in-part of application Ser. No. 07/269,429 filed Nov. 9, 1988, and now abandoned which is a continuation-in-part of application Ser. No. 07/114,618, filed Oct. 29, 1987, now U.S. Pat. No. 5,243,038 which is a continuation-in-part of application Ser. No. 06/927,258, filed Nov. 4, 1986, and now abandoned and claims priority to PCT 89/05016, filed Nov. 7, 1989.

INTRODUCTION

1. Technical Field

This invention is related to the production of high molecular weight polymers of amino acids based on biologically and chemically active structural polymers.

2. Background

Recombinant DNA technology has been applied in the isolation of natural genes and the expression of these genes in a variety of host cells. Typically, this technology has had utility in producing biologically active polypeptides, such as interferons or peptide hormones, which were impractical to produce in useful amounts by other means. It was also possible to produce modified proteins by isolating natural genes and utilizing the techniques of site specific, in vitro, mutagenesis to alter these genes and thereby change the polypeptides produced. Other polypeptides have been created by combining sections of various native genes to produce new polypeptides that are chimeric molecules of the several naturally occurring molecules.

With the advent of efficient and automated methods for the chemical synthesis of DNA, it has become possible to synthesize entire genes and to modify such synthetic genes at will during the course of synthesis. However, these various technologies have been applied to the production of natural or modified versions of natural polypeptides. There have been very few attempts to use these technologies to create substantially new polypeptides. In nature, polypeptides have a wide range of chemical, physical and physiological characteristics. Nevertheless there are commercial applications for which known, naturally occurring polypeptides are not appropriate.

While biotechnology is versatile, usually it has been limited in its applications to naturally occurring products or modifications of naturally occurring molecules. One great strength of organic chemical synthesis, by contrast, has been the ability to transform inexpensive carbon materials to a wide variety of polymeric molecules, including naturally occurring molecules, but most importantly entirely new chemical structures, such as polypropylene and polyacrylates, which have defined and predicted chemical properties not associated with naturally occurring molecules.

Such materials, particularly high-molecular weight polymers containing repeating sequences of amino acids, have proven difficult to produce by biochemical means. The genes necessary for producing large peptides containing repeating units of amino acids were unstable and often underwent intermolecular recombination causing deletions of repeating units in the gene. The development of a biotechnology which should produce polymeric molecules by biological processes similar to those available by organic synthesis would significantly broaden the range of applications of biotechnology.

BRIEF DESCRIPTION OF THE RELEVANT LITERATURE

The cloning of multiple lactose operators up to four in tandem is disclosed by Sadler et al., Gene, (1980) 8:279–300. Hybrid bacterial plasmids containing highly repeated satellite DNA is disclosed by Brutlag et al., Cell, (1977) 10:509–519. The synthesis of a poly(aspartyl-phenylalanine) in bacteria is disclosed by Doel et al. Nucleic Acids Research, (1980) 8:4575–4592. A method for enriching for proline content by cloning a plasmid which codes for the production of a proline polymer was disclosed by Kangas et al., Applied and Environmental Microbiology, (1982) 43:629–635. The biological limitations on the length of highly repetitive DNA sequences that may be stably maintained within plasmid replicons is discussed by Gupta et al. in Bio/Technology, p. 602–609, September 1983.

SUMMARY OF THE INVENTION

Methods and compositions are provided for the production of polypeptides having repetitive oligomeric units or strands which interact forming a structural component, where the structural components are separated by different amino-acid sequences having particular functional capabilities. (By "strands" is intended an ordered sequence capable of alignment with a second strand having substantially the same or a complementary sequence e.g., hydrophobic aligns with hydrophobic and hydrophilic aligns with hydrophilic.) The components of the repetitive units provide a structure which allows for availability of the intervening units for interacting with the environment, such as solutions, gases, gels and the like where the intervening sequence is substantially free of steric inhibition to interact with other molecules as compared to the strands. Long nucleic-acid sequences are built up by synthesizing nucleic-acid oligomers which express a plurality of individual repetitive peptide units and the oligomers are joined to provide a polynucleotide of the desired length. By providing for specific restriction sites which are relatively evenly spaced, additional sequences may be introduced at sites which provide for turns or other functional entity between repetitive strands. The resulting nucleic-acid open-reading frames may then be introduced into an appropriate expression vector for expression of the desired protein product.

DESCRIPTION OF THE SPECIFIC EMBODIMENTS

Novel polypeptides are provided which are polyoligomers of repeating, relatively short, amino acid sequence units forming strands, where the strands are separated by a different oligomeric unit which results in a sequence available to the environment of the polypeptide for a variety of functions.

The polypeptides which are encoded for by the nucleic acid sequences of the subject invention provide for strands which may align to provide for a basic structure. The strands will be protein chain segments of more or less linear conformation. The strands may be aligned in reverse or direct alignment, where a plurality of strands are separated by a sequence other than the repetitive sequence as a functional entity between the strands, so as to be accessible to solutes or components in the medium. The strands will be based primarily on repeating units of naturally occurring polymers, where the repeating units generally are at least three amino acids and may include the same amino acid twice.

The polymers of this invention may be used to provide a variety of structures for a variety, of purposes. Depending on the repeating units and their relationship to known polymeric structures, analogous mechanical, e.g., tensile properties, may be achieved, which may be modified for a particular intended purpose. The subject polymers may be used by themselves to produce various articles, including formed objects, coatings, or other structural or non-structural components including fibers, films, membranes, adhesives, emulsions, and the like or with other compounds or compositions to form composites, laminates or combinations of the aforementioned products.

The structurally aligned elements of the polymers may be β-sheets, α-helices, dynamic β-spirals, collagen helices, Type I or II, or combinations thereof, where there will be intervening elements which will be of different sequence and structure and will usually not participate in the aligned elements. For the most part, these intervening sequences will be loops or turns.

The genes of the subject invention comprise multimers of DNA sequences encoding the same amino acid sequence unit, where two or more different multimers encoding different amino acid units may be joined together to form a block copolymer. The individual units will have from 3 to 30 amino acids (9 to 90 nt), more usually 3 or 4 to 25 amino acids (9 to 75 nt), particularly 3 or 4 to 15 amino acids (9 to 45 nt), more particularly 3 or 4 to 9 amino acids (9 to 27 nt), usually having the same amino acid appearing at least twice in the same unit, generally separated by at least one amino acid. The units of the multimer coding for the same amino acid sequence may involve two or more nucleotide sequences, relying on the codon redundancy to achieve the same amino acid sequence.

The units of the strands will generally be at least about 25 amino acids and not more than about 200 amino acids, usually not more than about 100 amino acids, preferably from about 30 to 75 amino acids. The other sequence separating the strands will generally be at least about 4, more usually 6 amino acids and not more than about 50, usually not more than about 30 amino acids, more usually not more than about 20 amino acids.

For the most part the DNA compositions of this invention may be depicted by the following formula:

$$K_k(W(M)_m X_x((N)_n Y_y)_i L_1$$

wherein:

K is a DNA sequence encoding an amino acid sequence of from about 1 to 125 amino acids, usually 1 to 60 amino acids, generally being fewer than about 20% of the total number of amino acids, more generally being fewer than about 10% of the total number of amino acids, which may be any sequence, particularly a naturally occurring sequence where the multimer structural gene has been fused to another DNA sequence in reading frame. K, if present, will have the initiation methionine codon.

k is 0 or 1;

W has the formula:

$$[(A)_n(B)_p]_q$$

wherein:

A is a DNA sequence coding each time that it appears for the same amino acid sequence unit, normally having at least one amino acid appear at least twice in the sequence, where A will generally be from about 9 nucleotides (nt) and not more than about 90 nt, more usually from about 9 or 12 to 75 nucleotides, preferably from about 9 or 12 to 45 nt, more preferably from about 9 or 12 to 27 nt;

where there will usually be at least two different A's, usually not more than ten different A's, more usually not more than six different A's, which code for the same amino acid sequence but differ from each other by at least one nucleotide and may differ by as many as ten nucleotides, usually not differing by more than about five nucleotides from another A sequence, each of the different A's usually being repeated at least twice, at least two different codons are employed for the same amino acid, e.g., GGC and GGA for glycine, in different A's coding for the same amino acid sequence unit;

n will be an integer of at least 2, usually at least 4, more usually at least about 8, and not more than about 250, usually not more than about 200, frequently not more than about 125, and in some instances may not exceed about 50;

B is a DNA sequence different from A coding for an amino acid sequence other than the amino acid sequence unit coded by the A unit and serves as a linking unit between oligomers of A units. B will generally have from about 3 to 45 nt, (1 to 15 amino acids) more usually from about 3 to 30 nt (1 to 10 amino acids);

where the B units appearing in the gene may be the same or different, there usually not being more than about 10 different B units, more usually not more than about 5 different B units, where the B units may differ in from 1 to 45 nt, more usually from about 1 to 15 nt, where the different B's may code for the same or different amino acid sequence;

p is 0 or 1 and may differ each time there is a successive A unit;

q is an integer of at least 1 and will vary with the number of nucleotides in A and B, as well as the values of n and p. The variable q will be selected so as to provide for at least 90 nucleotides for the multimeric portion of the structural gene, preferably at least about 150 nt, more preferably at least 450 nt, and most preferably at least 900 nucleotides and the number of nucleotides will usually not exceed about 10,002, more usually not exceeding about 8,001, generally being in the range of about 900 to 6,000, more usually to about 5,001; and M is a DNA nucleotide sequence of 12 to 150 nt, usually 18 to 150 nt, more usually not more than about 90 nt, which may encode any amino acid sequence, usually encoding a functional sequence which provides for a natural or synthetic sequence resulting in a biological or chemical function or activity;

m and n are the same or different, being 0 to 3, usually 0 to 2, depending on whether a functional group is present in the polymer, usually being 1 to 2, where different, the same or similar functional groups may be combined in a contiguous manner.

X may be the same as or different from W, usually different, and will have the formula $$[A^1)_{n^1}(B^1)_{p^1}]_{q^1}$$

wherein:

$A^1$, $B^1$, $n^1$, $p^1$ and $q^1$ are the same as or different from A, B, n, p and q respectively, at least one being different, wherein the analogous symbols come within the same definition as their counterparts;

x is 0 or 1;

N is the same as or different from and comes within the same definition as M;

Y may be the same as or different from W, usually different, and will have the formula $$[A^2]_{n^2}(B^2)_{p^2}3q^2$$

wherein:
$A^2$, $B^2$, $n^2$, $p^2$ and $q^2$ are the same as or different from A, B, n, p and q respectively, at least one being different, wherein the analogous symbols come within the same definitions as their counterparts.

y is 0 or 1;
L may be the same or different from K, coming within the definition of K, but lacking the initiation methionine codon;
l is 0 or 1;
i is 1 to 100, usually 1 to 50, more usually 1 to 30, particularly 1, when x and y are 0;
when x or y are 1, q, $q^1$ and $q^2$ will be a total of at least 2, usually at least 5 and not more than about 50, usually not more than about 33.

The total number of nucleotides will be at least 90 nucleotides, usually at least about 150 nt, preferably at least about 900 nt and may be 20 knt (kilonucleotides), usually not more than about 15 knt, more usually not more than about 10 knt.

The polypeptide encoded by the above DNA sequence will have the following formula:

$$K_k'(W'M'X_x'N'Y_y')i\ L_1'$$

wherein:
W' will have the following formula $$[(D)_n\ (E)_p]_q$$

wherein:
D is the amino acid sequence encoded for by A and therefore has the numerical limitations based on 3 nucleotides defining a codon that codes for one amino acid;
E is the amino acid sequence encoded for by B, and therefore has the numerical limitations based on 3 nucleotides defining a codon, where each E may be the same or different, depending upon the coding of B;
and, wherein, likewise each of K', W', M', X', N', Y' and L' is the amino acid sequence encoded for by K, W, M, X, N, Y and L respectively. However, in the case of K and L, subsequent processing, such as protease treatment, cyanogen bromide treatment, etc. may result in partial or complete removal of the N- or C-terminal non-multimeric chains.

n, p, q, k, i and l have the same definitions as previously indicated.

Particular polymeric compositions having repeating multimeric units having the same compositions (A) will have the following formula where x and y are 0, $$K_k'\ [(D)_n(E)_p]_q L_1'$$

where all of the symbols have been defined previously; and the DNA sequence will have the formula $$K_k[(A)_n(B)_p]_q\ L_1$$

where all of the symbols have been defined previously.

Particular DNA sequences encoding copolymeric compositions having a repeating unit of two to three multimeric blocks will have the following formula:

$$K_k\ (W''M''X_x''N''Y_y'')_i''L_1$$

wherein:
W" is a multimer having the formula $$[(A^3)_{n^3}(B^3)_{p^3}]_{q^3},$$

where $A^3$ is of 3 to 8, usually 4 to 8 codons, otherwise coming within the definition of A;
$n^3$ will be from about 2 to 12, usually 2 to 10;
$B^3$ is of from 2 to 8, usually 4 to 6 codons;
$p^3$ is 0 or 1;
$q^3$ is of from about 2 to 25, usually 2 to 20;
X" and Y" are the same as or different from W", usually different, coming within the same definitions as W";
M" and N" come within the definitions of M' and N';
i" is at least 2, usually at least 5 and not more than about 75, usually not more than about 50, generally not exceeding 30;
with the other symbols as defined previously.

Where there is only one multimeric type, a preferred formula will simplify to the following formula:

$$K^*_{k^*}(W^*\ (M^*)_{m^*})_i \cdot L^*_1.$$

wherein:
K* is a DNA sequence encoding an amino acid sequence of from about 1 to 125 amino acids, usually 1 to 60 amino acids, which may be any sequence, generally being fewer than about 20% of the total number of amino acids, more generally being fewer than about 10% of the total number of amino acids, particularly a naturally occurring sequence where the multimer structural gene has been fused to another DNA sequence in reading frame. K*, if present, will have the initiation methionine codon;
k* is 0 or 1;
W* has the formula:

$$[(A^*)_{n^*}(B^*)_{p^*}]_{q^*}$$

wherein:
A* is a DNA sequence coding each time that it appears for the same amino acid sequence unit, normally having at least one amino acid appear at least twice in the sequence, where A will generally be at least from about 9 nucleotides (nt) usually from about 9 or 12 to 90 nt, more usually from about 9 or 12 to 75 nt, preferably from about 9 or 12 to 27 nt;

The A*'s may be the same or different; conveniently there may be two different A*'s, usually not more than six different A*s, which code for the same amino acid sequence but differ from each other by at least one nucleotide and may differ by as many as ten nucleotides, usually not differing by more than about five nucleotides from another A* sequence, each of the different A*'s usually being repeated at least twice; in some instances it may be advantageous to have two different codons employed for the same amino acid, e.g., GGC and GGA for glycine, in the same unit;
n* will be an integer of at least 2, usually at least about 4, and not more than about 50, usually not more than about 40, frequently not more than about 35, and in some instances may not exceed about 10;
B* is a DNA sequence different from A coding for an amino acid sequence other than the amino acid sequence unit coded by the A* unit and serves as a linking unit between oligomers of A* units. B* will generally have from about 3 to 45 nt (1 to 15 amino acids), more usually from about 3 to 30 nt (1 to 10 amino acids);
where the B* units appearing in the gene may be the same or different, there usually not being more than about 10 different B* units, more usually not more than about 5 different B* units, where the B units may differ in from 1 to 45 nt, more usually from about 1 to 15 nt, where the different B*'s may code for the same or different amino acid sequence;

p* is 0 or 1 and may differ each time there is a successive (A*)$_n$* unit;

q* is an integer of at least 1 and will vary with the number of nucleotides in A* and B*, as well as the values of n* and p*. The variable q* will be selected so as to provide for at least 90 nucleotides for the strand, preferably at least about 150 nt, and not more than about 600 nt, usually not more than about 501 nt;

M* is a nucleotide sequence of at least 12 nt, usually at least about 18 nt and not more than about 150 nt, usually not more than about 90 nt, usually in the range of about 12 to 90 nt;

m* is 1 to 3, usually 1 to 2, wherein the m*s may be the same of different;

i* is at least 2 and not more than 100, usually not more than about 50, preferably at least about 3 and not more than about 30;

for each i*th unit, m* is 0 or an integer as indicated above, being at least an integer for at least 1 unit, so that the total number of m*'s varies from 1 to i;

L* comes within the definition of K*, except that L* will not have the initiation methionine codon;

1* is 0 or 1.

The total number of nucleotides will be at least 150 nt usually at least 900 nt, and not more than about 10,002 nt, usually not more than about 5,001 nt.

The polypeptide encoded by the above DNA sequence will have the following formula:

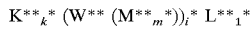

wherein:
W** will have the following formula:

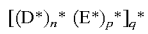

wherein:
D* is the amino acid sequence encoded for by A* and therefore has the numerical limitations based on 3 nucleotides defining a codon that codes for one amino acid;

E* is the amino acid sequence encoded for by B*, and therefore has the numerical limitations based on 3 nucleotides defining a codon, where each E* may be the same or different, depending upon the coding of B*;

K, L and M** are the amino acid sequences encoded for by K*, L* and M*, and therefore have the numerical limitations based on 3 nucleotides defining a codon that codes for one amino acid; K is of from 1 to 125 amino acids, optionally including the initiation methionine, while L is of from 1 to 125 amino acids, and M** is of from 3 to 50 amino acids, particularly including a naturally occurring sequence; and k*, 1*, m*, i*, n*, p* and q* have already been defined.

The compositions of the invention will usually have a molecular weight of at least about 3 kDal, usually 5 kDal, frequently at least 15 kDal and may have molecular weights as high or higher than 500 kDal, usually not exceeding 300 kDal, more usually not exceeding about 250 kDal. The composition will be substantially homogeneous, with each of the molecules of the same molecular weight and chain length.

Copolymers may be prepared, particularly block copolymers. The copolymers may provide a variety of advantages in providing greater flexibility in controlling polymer chemical and physical e.g., mechanical, properties, introduce compatible functions, and produce unique chemical and physical properties due to interactions between the different repeating units.

Usually combinations of multimers will be used, e.g., $((A^a)_n(B^b)_p)_q$, where the symbols A, B, n, p and q are as previously defined and a and b indicate that different multimers are involved, where a and b are in the range of 1 to 3, where a and b are equal to the same number. This intends that $A^1$ and $B^1$ are associated, as are each of the other A's and B's and $A^1$ refers to a sequence which may be the same or different from $A^2$ but $(A^2)_n(B^2)_p$ is different from $(A^2)_n(B^2)_q$ Combinations include using hard and soft groups to enhance flexibility, combining silk and elastin multimers, providing for changes in the structural properties of collagen, by introducing an adhesion-like protein to provide strong bonding to a surface, or the like.

Copolymers will usually be at least about 5 kDal, more usually 10 kDal, usually not more than about 500 kDal, mote usually not more than about 300 kDal.

The unaligned sequence may be the same or different within a multimer or the same or different unaligned sequences in the different multimers.

The nucleotide sequences which are employed will be synthesized, so that the repetitive units may have different codons for the same amino acid as described above. Usually, at least about 25%, more usually at least about 40%, and generally at least about 60%, but not greater than about 95%, preferably not greater than about 90% of the nucleotide sequences encoding the repetitive units will be the same. Greater diversity within those ranges will be employed where the initial constructs are experimentally shown to undergo spontaneous recombination events.

Various natural proteins have repeating structures, such as collagen with a G-X-Y (wherein X equals any amino acid, often ala or pro, and Y equals any amino acid, often pro or hydroxy-pro) repeating unit, elastin with VPGG (SEQ ID NO:01), VPGVG (SEQ ID NO:02), and/or APGVGV (SEQ ID NO:03) units, keratin with a so called "heptad" repeat unit consisting of a seven amino acid oligopeptide with two positions separated by two amino acids, usually positions three and six, occupied consistently with hydrophobic aliphatic or aromatic residues, e.g., AKLKLAE (SEQ ID NO:04) or AKLELAE (SEQ ID NO:05), and mussel adhesive with a decapeptide or hexadecapeptide coming within the sequence A-K-P-P*-S-T-Y-X-P-P*-P-S-T-Y-X-K (SEQ ID NO:06) (P* is hydroxyproline and X is an aromatic amino acid, particularly L-dopa; see U.S. Pat. Nos. 4,585, 585 and 4,687,740). The repeating units may be used individually or in combination, where individual units may alternate in a particular pattern or individual strands may be provided.

Of particular interest are polypeptides which have as a repeating unit SGAGAG (SEQ ID NO:07) (G=glycine; A=alanine; S=serine). This repeating unit is found in a naturally occurring silk fibroin protein, which can be represented as GAGAG(SGAGAG)$_8$SGAAGY (SEQ ID NO:08) (Y=tyrosine).

Also of interest are polypeptides which have as a repeating unit.

where 1 is a basic or acidic amino acid, particularly K or E and the repeating units alternate as to whether 1 is a basic or acidic amino acid. This structure is commonly found in keratin.

For the intervening oligomers or turns between the strands, various sequences may be used, depending upon the desired purpose of the polymer. Thus, the intervening sequence may be unaligned, flexible, accessible, functional or combinations thereof. Thus, the intervening sequence in association with the strand sequence can be designed to provide a wide variety of products which may be formed, fabricated, extruded, spun, woven, coated, or the like. The intervening sequence may provide for a ligand, which may serve to bind to antibodies, naturally occurring receptors, non-amino-acid molecules, or the like. In this way, the polymeric structures may be used to specifically bind a wide variety of molecules serving as affinity columns, use in diagnosis, sensors, cell separation, device coatings having, for example, antithrombogenic properties, cell substrates, and the like.

The intervening sequence may provide chemically active amino acids for chemical crosslink sites, which may serve to covalently attach functional peptides, synthetic or natural polymers or proteins, non-amino acid molecules, and the like. The intervening sequence may be a naturally occurring sequence or a modified naturally occurring sequence. Naturally occurring sequences may be derived from a wide variety of sources with a variety of functions. Such sequences may be a cellular growth inhibitor sequence, e.g., from tenascin (Chiquet-Ehrismann et al., (1988) *Cell* 53:383–390); cell growth promoting attachment factors, e.g., from fibronectin, -RGD-, -REDV- (Humphries et al., (1988) *J. Cell Biol.* 103:2637–2647), vitronectin, -RGD- (Suzuki et al., (1985) *EMBO J.* 4:2519–2524), collagen, -RGD-, and as described in WO 89/03392, laminin B1 -YIGSR- (Graf et al., (1987) *Cell* 48:989–996), bacterial adhesive, -SLF-, -ALF-; (Jacobs et al., (1987) *J. Bacteriology* 1691:735–741), growth hormones and insulin; inclusion sequences (GAGC and GCCV, which provide systems for attachment and cross-linking; VSPD, VCDP and DPGK, which provide an unaligned structure); cellular function activators, such as major histocompatibility complex antigens, Class I and II, particularly the $\alpha_1$, $\alpha_2$, $\beta_1$ and $\beta_2$ regions, e.g., HLA-A2 amino acids 50–80 and 140–170 (Bjorkman et al., (1987) *Nature* 329:512–518) and HLA-D amino acids 1–90 (Todd et al., (1988) *Science* 240:1003–1009); growth factor domains, e.g., EGF, TGF and VGF, IL-1-10, particularly -2, -3 and -4, and erythropoietin; viral attachment sequences, such as human CD4 amino acids 35–60 (Clayton et al., (1988) *Nature* 335:363–366) and 70–95 (Lifson et al., (1988) *Science* 241:712–716); sequences which promote the binding of non-protein molecules, such as the heparin binding domain of vitronectin, metal binding domains, e.g., metallothioneins, H-H, H-C-C-H (SEQ ID NO:10) and C-H-H-C (SEQ ID NO:11), etc. glucose and other sugar binding domains, e.g., lectins, B chains of toxins, such as abrin, ricin, diphtheria toxin, safratoxin, or fragments thereof, etc.; drug or toxin binding domains for detoxification; and chemically active amino acids or amino acid sequences for post-translational modifications, such as N-X-S for N-linked glycosylation and the amino acids, C, M, H, K, R, D, E, W, P, Y, N and Q for chemical modification.

Sequences of specific interest as intervening sequences include:

D P G K G X Y (SEQ ID NO:12)

wherein at least one of X and Y is C;

E P G Y I G S R C D A G Y; (SEQ ID NO:13)

P K G D R G D A G P K; (SEQ ID NO:14)

A V T G R G D S P A S; (SEQ ID NO:15)

G R G G S F G G S S Y G G G S; (SEQ ID NO:16)

G A G C G D P G K G C C V A; (SEQ ID NO:17)

V C D R G Y I G S R C D: and (SEQ ID NO:18)

P K G D R A D A G P K; (SEQ ID NO:19)

where conservative substitutions may be made other than at the functional site.

For the cysteine product it will be desirable to have two or three cysteines in a multimer unit, preferably having a cysteine proximal to each end of the multimer unit. For chemical cleavage the dipeptide DP or EP is desirable.

Other sequences of interest may be epitopes of microorganisms, e.g., virus, bacteria, fungi and protozoa, phosphorylation sites, peptidase recognition sites or the like.

The use of genetic engineering in the preparation of copolymers involving repeating units with intervening sequences is a powerful method for varying properties, by appropriate choice of the different units, the number of units in each multimer, the spacing between them, and the number of repeats of the multimer combination assembly. Thus, by varying the number and arrangement of the primary multimers, a variety of different physical and chemical properties can be achieved.

Exemplary of the use of the block copolymers are combinations of silk units and elastin units to provide products having properties distinctive from polymers only having the same monomeric unit.

To prepare the structural genes, various approaches can be employed. To prepare the oligomers, complementary strands of DNA may be synthesized, so that upon hybridization double-stranded DNA is obtained with the appropriate termini. If desired, each of the oligomeric units may be the same, so that in a single step, a concatemer may be obtained depending upon the conditions of the hybridization. Normally, conventional annealing and ligating conditions will be employed, such as are described in the examples that follow.

If desired, two different oligomeric units may be prepared where the termini of the two units are complementary one with the other, but the termini of the same unit are unable to bind together. In this way one can build individual oligomeric units and then join them together to form the concatemer, where the intervening linking sequences are defined at least in part by the termini. Depending upon the construct, the 5' terminus may provide for the initiation codon methionine, or the structural gene may be joined to an adapter which may provide for a unique sequence (optionally cleavable by enzymatic or chemical treatment) at the 5' terminus or may be inserted into a portion of a gene, usually endogenous to the host, in proper reading frame so as to provide for a fusion product. By providing for appropriate complementary termini between the adapter or truncated gene and the 5' end of the subject structural gene, the sequences can be joined in proper reading frame to provide for the desired protein. Advantages that may be achieved by employing adapters or fusion proteins include having specific sequences for special purposes, such as linking, secretion, complex formation with other proteins, affinity purification, or the like. The 3' region may be similarly modified to provide analogous functions.

Once the structural gene has been assembled, it may be cloned; clones having the desired gene, particularly as to sequence length, may be isolated and the gene may be removed and used to join to a sequence for expression.

The expression construct will include transcriptional and translational initiation and termination regulatory regions, 5' and 3', respectively, of the structural gene. As already indicated, these regions may be created by employing a fusion protein, where the subject structural gene is inserted into a different structural gene downstream from its initiation codon and in reading frame with the initiation codon. Alternatively, various transcriptional and translational initiation regions are available from a wide variety of genes for use in expression hosts, so that these transcriptional and translational initiation regions may be joined to the subject structural gene to provide for transcriptional and translational initiation of the subject structural genes. A wide variety of termination regions are available which may be from the same gene as the transcriptional initiation region or from a different gene. Numerous constructs have been disclosed in the literature, and the same procedures may be applied with the subject gene as have been employed with other structural genes.

Of particular interest is the use of an inducible transcription initiation region. In this manner, the host strain may be grown to high density prior to significant expression of the desired product. Providing for inducible transcription is particularly useful where the peptide is retained in the cellular host rather than secreted by the host.

A number of inducible transcription initiation regions exist and can be employed in particular situations. The inducible regions may be controlled by a particular chemical, such as isopropyl thiogalactoside (IPTG) for inducing the beta-galactosidase gene. Other inducible regions include lambda left and right promoters; various amino acid polycistrons, e.g., histidine and tryptophan; temperature sensitive promoters; and regulatory genes, e.g., $cI^{ts}$ 857.

An alternative system which may be employed with advantage is use of a combination of transcription initiation regions. A first transcription initiation region which regulates the expression of the desired gene but which is not functional in the expression host by failing to be functional with the endogenous RNA polymerase is employed. A second transcription initiation region, such as an inducible region, can then be employed to regulate the expression of an RNA polymerase with which the first transcriptional initiation region is functional. In this manner expression only occurs upon activation of the regulatory region controlling the expression of the exogenous RNA polymerase. This system may be illustrated with the T7 phage transcription initiation region, specifically the initiation regions of genes 9 and 10 of T7 phase.

An alternative system relies on the use of mutants which undergo a developmental change based on a change in the environment, such as a lack of a nutrient, temperature, osmotic pressure, salinity, or the like. Illustrative of this system, strains of *B. subtilis* can be obtained which are incapable of sporulation but which can produce those components which initiate expression of products involved with sporulation. Therefore, by a change in the condition of the medium, a transcription initiation region associated with sporulation will be activated. In this situation, the host provides the necessary inducing agent or activator to initiate expression.

Various other techniques exist for providing for inducible regulation of transcription and translation of a gene in a particular host.

For the most part, the host will be a unicellular organism, either a prokaryote or a eukaryote, selected from bacteria, algae, fungi, filamentous fungi, plant or animal tissue culture cells, etc. Illustrative hosts include *E. coli, B. subtilis, B. stearothermophilus, S. cerevisiae, Aspergillus, Neurospora,* Streptomyces, CHO cells, HeLa cells, etc. and the like. Alternatively, whole plants may be employed.

The expression construct for expression of the desired gene, by itself or in conjunction with any auxiliary genes involved with transcription, will normally be joined to an appropriate vector for introduction into the expression host. A large number of vectors are commercially available with others being described in the literature. The vectors are normally characterized by having one or more unique restriction sites, a replication system for extrachromosomal maintenance in the host, and one or more markers which allow for selective pressure on the host. The markers may provide complementation, prototrophy to an auxotrophic host, resistance to a biocide, e.g., an antibiotic such as penicillin or kanamycin, or the like. In some instances, rather than selective pressure, a marker gene is employed which allows for detection of particular colonies containing the gene. This situation is illustrated by the gene for beta-galactosidase, where a substrate is employed which provides for a colored product.

The expression construct, including any auxiliary genes, may be introduced into the expression vector in accordance with known techniques, particularly employing restriction, insertion, and ligation.

The expression construct may then be used for transformation of the appropriate host. Depending upon the host, either intact cells or protoplasts may be employed, where transformation or conjugation is employed. Conveniently, calcium phosphate precipitated DNA or non-ionic detergents may be employed to introduce the plasmid into the host. It should be appreciated that it is not necessary to employ vectors for host transformation, since bare DNA can be introduced for integration into the genome. However, even where integration is desired, a much greater efficiency of integration is achieved employing the vectors, thus favoring the employment of vectors.

Depending upon the nature of the vector, the expression construct may be maintained on an extrachromosomal element or become integrated into the host. Where integration is desired, it will usually be desirable with prokaryotes and some eukaryotes to have a sequence homologous to a sequence in the chromosome of the host. Usually the sequence will be at least about 200 bp and not more than about 5000 bp, usually not more than about 2000 bp. The choice of the homologous sequence is somewhat arbitrary, but may be used for complementation, where the host is an auxotrophic mutant and the homology provides prototrophy.

The transformants or integrants may then be grown in an appropriate nutrient medium to high density, followed by induction of transcription in accordance with the nature of the transcriptional system of the expression construct. Where the desired protein is retained in the cytoplasm, these cells are harvested and lysed, and, depending upon the use of the protein, the protein may be further purified in accordance with conventional techniques, such as chromatography, solvent extraction, affinity chromatography, centrifugal sedimentation, filtration and the like.

The following examples are offered by way of illustration and not by way of limitation.

EXPERIMENTAL

EXAMPLE 1

DNA Preparation Methods

1. Preparation of plasmid DNA from *E. coli*.

A. Small scale.

Plasmid DNA was prepared from 1.5 ml cultures by either the boiling procedure or the alkaline lysis method (Maniatis et al., Molecular Cloning: A Laboratory Manual. Cold Spring Harbor Laboratory, Cold Spring Harbor. (1982)).

B. Large scale. A plasmid-carrying strain was grown overnight in 1 liter of Luria broth with the appropriate antibiotic. The cells were collected by centrifugation at 10,000 xg for 5 min and resuspended in ml of ice cold TE (10 mM Tris-HCl pH 8, 1 mM EDTA). The cells were centrifuged again, resuspended in 4 ml of TES (TE and 25% w/v sucrose) and homogenized by vortexing. The samples were kept on ice for the following steps. Lysozyme (1 ml of 10 mg/ml) was added to the cell suspension and incubated for 5 min before the addition of 2 ml of 0.5 M EDTA pH 8. After 10 min incubation, 50 ml of proteinase K (40 mg/ml) were added followed 10 min later with 15 ml of lysing buffer (0.1% Triton X-100, 1 mM EDTA, 50 mM Tris-HCl pH 8). After 15–20 min, the cell lysate was centrifuged at 35,000 xg for 90–120 min. The supernatant (19.8 ml) was transferred to a plastic tube with 20 μg of CsCl and 400 μl of ethidium bromide (10 mg/ml). After dissolution, the mixture was divided into two polyallomer ultracentrifuge tubes, sealed with heat and centrifuged in a Beckman Ti 65 motor at 60,000 rpm for 24 hr. The lower plasmid DNA band was removed from the tube with a hypodermic needle. The ethidium bromide was extracted three times with an equal volume of NaCl-saturated isopropanol. Two volumes of $H_2O$ were added to the DNA solution, and then the DNA was precipitated with ethanol.

2. Preparation of double-stranded DNA.

A culture of JM103 was grown to an $OD_{600}$ of about 0.2 and then divided into aliquots of 2 ml. Each aliquot was infected with a fresh plaque of M13 and incubated at 37° C. for about 6 hr with vigorous shaking. Then the cells were pelleted and the supernatant was saved for subsequent infections. The double-stranded phage DNA was extracted by the boiling method (Maniatis et al.).

3. Deproteinization.

Phenol extraction was performed on a convenient volume of DNA sample, typically between 100 μl to 10 ml. The DNA sample was diluted in 0.01 M TRIS-HCl pH 7.5, 1 mM EDTA and an equal volume of water-saturated phenol was added. The sample was vortexed briefly and placed on ice for 3 min. After centrifugation for 3 min in a microfuge, the aqueous layer was removed to a new tube and extracted once with an equal volume of chloroform:isoamylalcohol (24:1).

4. Ethanol precipitation.

DNA in an aqueous buffer was concentrated by ethanol precipitation. To the DNA sample was added 1/10 volume of 3 M sodium acetate pH 7.5 and 2–3 volumes of cold ethanol. The DNA was precipitated for 30 min at −70° C. or overnight at −20° C. and then pelleted by centrifugation in the microfuge for 15 min at 4° C. The pellet was washed once with 200 μl of cold 80% ethanol and pelleted again for 10 min at 4° C. After air drying or lyophilization, the pellets were resuspended in the appropriate buffer.

5. Phosphatase treatment of DNA.

Phosphatase treatment of DNA was performed by adding 1 μl (25 units) of calf intestinal phosphatase (Boehringer Mannheim) directly to the restriction enzyme digestion reaction and continuing the incubation for 30 min at 37° C. The phosphatase was inactivated for 60 min at 65° C. prior to deproteinization by phenol extraction.

6. Fill-in reaction with DNA polymerase I.

DNA was resuspended in buffer containing 50 mM Tris-HCl pH 7.4, 50 mM KCl, 5 mM $MgCl_2$, and 400 μM each of the four deoxynucleotide triphosphates. Ten units of Klenow DNA polymerase (BRL) were added, and the reaction was allowed to proceed for 15 min at room temperature. The DNA was then phenol extracted and ethanol precipitated.

7. T4 polynucleotide kinase reaction.

The reaction (10 μl) contained: T4 polynucleotide kinase (BRL), 150 ng of DNA, 1 μl of 10 x kinase buffer (0.7 M Tris-HCl pH 7.6, 0.1 M $XgCl_2$, 50 mM DTT) and ($^{32}$P]-ATP (200–300 μCi). This was incubated at 37° C. for 30 min and then the DNA was purified using a NACS column (Bethesda Research Labs).

8. Digestion with restriction endonucleases.

DNA was digested with restriction endonucleases (REN) in 1 x "AA" buffer [10 x AA buffer is 330 mM Tris-acetate, pH 7.9, 660 mM potassium acetate, 100 mM magnesium acetate, 50 M dithiothreitol (DTT) and 1 mg/ml bovine serum albumin (nuclease free)]. Whenever possible, the concentration of DNA was kept below 1 μg/25 μl. Incubation was at 37° C. for 1–4 hrs for most restriction endonucleases except for BalI, BanI and NaeI digestions which were incubated overnight.

9. Analytical agarose gel electrophoresis of DNA.

To DNA samples for gel analysis was added 0.2 volumes of loading buffer (5 x electrophoresis buffer, 0.01% bromphenol blue dye, 50 mM EDTA, and 50% glycerol). Then the samples were loaded into lanes of a horizontal submerged electrophoresis unit containing a 1.0% (w/v) agarose gel. The electrophoresis buffer was either 1 x TAC or ½ x TBE. The 1 x TAC is 40 mM Tris-base, 10 mM EDTA, adjusted to pH 7.8 with acetic acid. The ½ x TBE is 0.045 M Tris-base, 0.045 M boric acid, 1 mM EDTA, pH 8. The gel was run at 40–50 V for 18 hr, then removed and stained with 0.5 g/ml ethidium bromide for 30 min. The DNA bands were visualized on a long wavelength UV transilluminator.

10. Preparative agarose gel electrophoresis.

The procedures and materials are the same as for the analytical agarose gel electrophoresis. The only difference is the use of low melting point (LMD) agarose, ranging in concentration from 0.5 to 2.5% (w/v) depending on the size of the DNA fragment to be purified. DNA restriction fragments were excised from the LMP agarose gels after visualization with ethidium bromide.

11. NACS purification.

Gel fragments containing DNA were melted at 70° C. for 5 min and diluted approximately 5 fold with TE1 (10 mM Tris-HCl pH 7.5, 0.2 M NaCl). The gel solution was applied to a NACS column (BRL). The column was washed with 5 ml of the same buffer. The bound DNA was eluted with 300 μl of either TE2 (10 mM Tris-HCl pH 7.5, 1.0 M NaCl) for DNA fragments smaller than 1000 bp or TE3 (10 mM Tris-HCl pH 7.5, 2M NaCl) for larger fragments. The eluted DNA was concentrated by ethanol precipitation.

12. DNA ligation.

Reactions for ligating cohesive ends contained: 1 μg DNA, 1 x AA buffer (see step 8, above) 1 mM ATP and 20 units of T4 DNA ligase (BRL) in a 20 μl final reaction volume. The ligation was allowed to proceed for 16–18 hr at 15° C. or 1–2 hr at room temperature. For blunt-ended ligations the reactions contained 1 μg DNA, 25 mM Tris-HCl pH 7.5, 5 MM $MgCl_2$, 5 mM DTT, 0.25 mM spermidine, 200 mg BSA, 1 mM hexamine cobalt chloride (HCC), 0.5 M ATP and 400 units T4 DNA ligase (NEB) in a 20 μl reaction volume. The ligation was allowed to proceed for 30 min to 1 hr at room temperature.

Bacterial Transformation Methods

1. Preparation of transformation-competent E. coli cells.

A culture of 200 ml of sterile L broth was inoculated with a small loopful of E. coli cells. This was incubated with shaking at 37° C. until the $OD_{600}$ was approximately 0.5. The culture was placed on ice for 10 min and centrifuged at 6,000xg for 10 min. The cell pellet was resuspended in 100 ml of ice-cold 0.1 M $MgCl_2$, kept on ice for 30–40 min and centrifuged again. The pellet was resuspended in 2 ml of ice-cold 100 mM $CaCl_2$, transferred to a sterile test tube and incubated on ice for 24 hr. The competent cells were then aliquoted and stored at −70° C.

2. Transformation of E. coli.

An aliquot of frozen competent cells were thawed on ice. To 50 μl of cells, 0.1 to 1 μg of DNA was added and the mixture was incubated on ice for 30 min. The tube was removed from ice and placed in a 42° C. bath for 2 min. L broth (1 ml) was added and the transformation mix incubated with shaking at the desired temperature (usually 30° C. or 37° C.) for 2 hr. Then one-tenth of the transformation was plated on L broth plates containing the appropriate antibiotic and, when necessary, XGAL and IPTG were added.

Antibody Production, Protein Chemistry and Electrophoresis of Proteins

1. Preparation of antibody to artificially synthesized Peptides.

Synthetic peptide of sequence $(GAGAGS)_8GAAGY$ was coupled to BSA using the glutaraldehyde procedure of Kagen and Glick (1979) infra. The degree of coupling was monitored using trace amounts of radioactive iodinated synthetic peptide. Peptide conjugates at a concentration of 1 mg/ml in complete Freund's adjuvant were used to immunize rabbits at day 0. Animals were re-injected with antigen in Freund's incomplete adjuvant at day 30 and titered at day 60. Positive sera was detected using a microtiter RIA using the synthetic peptide as antigen. Kagen and Glick (1979), in Methods of Radioimmunoassay, Jaffe and Berman (eds.), Academic Press, p 328.

The synthetic peptide of 53 amino acids as described above was prepared on an Applied Biosystems peptide synthesizer. The yield of this material, which has a molecular weight of 3640 was approximately 0.5 grams. The peptide was coupled to bovine serum albumin. The material was sent to Antibodies, Inc. for preparation of antibodies in rabbits. Antisera was obtained that reacted with synthetic peptides of the SLPIII sequence. These antisera have been useful for the detection of fusion peptides containing gly-ala sequences.

Following the procedure described above two additional peptides were synthesized having the formula YTITVYAVT-GRGDSPASSKPISINYC (SEQ ID NO:20) of fibronectin (the FCB portion) and (SEQ ID NO:21) the sequence $(GAP[GPP]_4)_2$ (the repeat unit of the collagen-like protein ("CLP") portion), which were coupled to keyhole limpet hemocyanin for use as immunogens. Polyclonal antisera were then prepared as described above which bound to the FCB and CLP peptides, respectively.

2. Polyacrylamide gel electrophoresis of proteins.

Approximately $10^9$ E. coli cells from growing cultures were pelleted by centrifugation at 10,000 xg for 5 min. The cell pellets were resuspended in 100 to 500 μl of 2X sample buffer (100 mM Tris-HCl pH 6.8, 4% SDS, 10% β-mercaptoethanol, 60% glycerol or sucrose) and sonicated for 30 sec using a Tekmar sonic disruptor. Samples were boiled for approximately 5 min and 20 to 100 μl of the cell lysates were loaded on an SDS-polyacrylamide gel (7.5 to 16% w/v). The gels were prepared following the procedure of Laemmli (*Nature*, 27:_80–685 (1970)). The proteins in the gels were stained with 2% Coomassie brilliant blue in 10% methanol, 7.5% acetic acid for 1 hr and destained in 10% methanol, 7.5% acetic acid overnight.

3. Immunoblotting of proteins in gels.

After protein electrophoresis, one of the flanking glass plates was removed from the polyacrylamide gel. The gel surface was wetted with transfer buffer (25 mM Tris-HCl, 192 mM glycine, 20% methanol). A piece of nitrocellulose paper (Sartorius, SM11307) was saturated with transfer buffer and laid on the gel. Air bubbles between the filter and the gel were removed. The gel and nitrocellullose filter were placed in the transfer unit as specified by manufacturer (Bio-Rad). Transfer was allowed to proceed at 200 mA for 3–4 hr. Then the nitrocellulose filter was removed and stained with Amido-Schwartz for 3 min (0.05% Amido black, 45% deionized $H_2O$, 45% methanol, 10% acetic acid) and destained in $H_2O$. The filter was incubated for at least 10 min at room temperature in "BLOTTO" 5% w/v nonfat dry milk, 50 mM Tris-HCl pH 7.4, 0.9% w/v NaCl, 0.2% w/v sodium azide). The filter was placed in serum appropriately diluted (1:50 to 1:500) in 0.5X Blotto (2.5% nonfat dry milk, 50 mM Tris-HCl pH 7.4, 0.9% NaCl, 0.2% sodium azide) and was gently agitated for approximately 16 hr at room temperature. The filter was washed for 1 hr with 5 changes of TSA (50 mM Tris-HCl pH 7.4, 0.9% NaCl, 0.2% sodium azide). The blot was placed in 15 ml of 0.5X BLOTTO solution containing $1\times10^7$ cpm of the $^{125}I$-protein A and gently agitated for 2 hr at room temperature. The filter was washed for 2 hr with a minimum of 7 changes of TSA, rinsed once with deionized $H_2O$ and air dried. The blot was covered with Saran wrap and autoradiographed.

4. Amino Acid Analysis.

Amino acid compositions are determine by the PTC derivatization procedure of Henrickson and Meredith (1984). Protein samples were hydrolysed with 5.7 N constant boiling HCl at 108° C. for 24 hours in vacuo. After reaction with PITC, amino acid derivatives were detected at 254 nm by HPLC reverse phase chromatography using a Hewlett Packard 1090 or Waters 600E system and a Supelco C18 column (4.6 mm×25 cm) with a linear gradient of 0–50% acetonitrile in 0.1 M $NH_4OAc$ pH 6.78 as a mobile base. Henrickson, R. L. and Meredith, S.C. (1984) Amino Analysis by Reverse Phase High Performance Liquid Chromatography., *Anal. Biochem.* 137:65–74.

5. Amino Acid Sequence Analysis.

The N-terminal amino acid sequence was determined by automated Edman degradation using an Applied Biosystems Model 470A gas phase protein sequenator. The PTH amino acid derivatives were analyzed by reverse phase HPLC using a Hewlett Packard 1090 or Waters 100E system and an Altex C18 column (2 mm×25 cm) with a complex gradient buffer system.

6. Peptide Synthesis.

Synthetic peptides were prepared by solid phase synthesis on an Applied Biosystems Model 430A Peptide Synthesizer using the standard symmetric anhydride chemistry as provided by the manufacturer. The coupling yield at each step was determined by the quantitative ninhydrin procedure of Sarin et al., (1981). The synthetic peptide was cleaved from the solid support and amino acid blocking groups were removed using anhydrous HF (Stewart and Young, 1984). Crude peptides were desalted by chromatography over Sephadex G-50. Sarin, V. K., Kent, S. B. H., Tam, J. P. and Merrifield, R. B. (1981). *Anal. Biochem.* 237:927–936. Stewart, J. M. and Young, J. D. (1984). Solid Phase Peptide Synthesis, Pierce Chemical Company, Rockford, Ill. pp 85–89.

Synthetic DNA Methods

1. In vitro DNA synthesis.

The N,N-diisopropylphosphoramidites, controlled-pore glass columns and all synthesis reagents were obtained from Applied Biosystems, Foster City, Calif.

Synthetic oligonucleotides were prepared by the phosphite triester method with an Applied Biosystems Model 380A or 381A DNA synthesizer using a 10-fold excess of protected phosphoramidites and 1 $\mu$mole of nucleotide bound to the synthesis support column. The chemistries used for synthesis are the standard protocols recommended for use with the synthesizer and have been described (Matteucci et al., *J. Amer. Chem. Soc.*, 103:3185–3319 (1981)). Deprotection and cleavage of the oligomers from the solid support were performed according to standard procedures as described by McBride et al., *Tetrahedron Letters*, 24:245–248 (1983). The repetitive yield of the synthesis as measured by the optical density of the removed protecting group as recommended by Applied Biosystems (1984) was greater than 97.5%.

The crude oligonucleotide mixture was purified by preparative gel electrophoresis as described by the Applied Biosystems protocols of Nov. 9, 1984 (User Bulletin No. 13). The acrylamide gel concentration varied from 10 to 20% depending upon the length of the oligomer. The purified oligomer was identified by UV shadowing, excised from the gel and extracted by the crush and soak procedure (Smith, *Methods in Enzymology*, 65:371–379 (1980)).

2. Sequencing of DNA.

DNA sequences were determined by the following methods. Fragments containing the region of interest were cloned into the multiple cloning site of M13mp18 or M13mp19 (Maniatis et al., 1982, and Norrander et al., 1983). Single-stranded DNA was prepared and sequenced by the primer extension method (Sanger et al., 1977 and Biggin et al., 1983) using $^{35}$S-deoxyadenosine 5'-(alpha-thio)-triphosphate (New England Nuclear) as label. In some cases, reverse transcriptase (Molecular Genetics) was used to extend the primer, using the dideoxy:deoxynucleosidetriphosphate ratios utilized by Zagursky et al. (*Gene Anal. Tech.* (1985) 2:89–94). Deoxyadenosine triphosphate labeled with either $^{32}$P or $^{35}$S was used in these reactions. Compression artifacts which appeared in some G-C rich sequences were overcome by eliminating deoxyguanosine triphosphate from the G reaction, and using deoxyinosine triphosphate (P-L Biochemicals) at a final concentration of 37.5 $\mu$M instead. In the other mixes, the concentration of dideoxyGTP in the G reaction was 0.5 mM. All sequences were run on 6 or 8% polyacrylamide gels containing 8 M urea (Sanger et al., 1978). Primers used for sequencing were purchased from P-L Biochemicals. Storage and analysis of data utilized software from both DNAstar and International Biotechnologies, Inc, for IBM personal computers and DNA Strider, DNA Inspector IIe or DNAid for Apple Macintosh personal computers.

Dideoxy DNA sequencing of double stranded plasmid DNA.

Plasmid DNA was prepared as described previously (Preparation of plasmid DNA from *E. coli*, Small scale, Maniatis et al.). Primers were synthesized using a DNA synthesizer as described previously, and were annealed to the plasmid DNA following the procedure described above for M13 sequencing. The sequencing reactions were done using Sequenase (United States Biochemicals) and the conditions were as recommended by the supplier. All sequences were run on polyacrylamide gels as described above.

Fermentation Conditions

A wide variety of fermentors can be utilized, including, for example, a 15 liter Chemap, a 15 liter Braun, or a 15 liter MBR, all with a working volume of 10 liters, or a 2 liter MBR with a working volume of 1 liter. The culture conditions are: temperature=30° C, pH=6.8; NaOH 2.5M or NH$_4$OH (30% v/v) is used for pH regulation. The headspace pressure is below 0.3 bar. The dissolved oxygen is regulated at 50%. The air flow varies from 0.5 L/min to 20 L/min. The agitation rate varies between 200 to 1500 rpm.

The fermentor is inoculated with a 10% (v/v) inoculum grown in medium A for 15 hours at 30° C. under agitation.

Medium B, C or D is the fermentor medium. The starting volume in the case of a 10 liter fermentation, is no less than 3 liters, and in the case of a 1 liter fermentation, is no less than 0.5 liters.

If the fermentor starting volume is less than the final volume desired, then when the carbon source concentration reaches 1%, a concentrated solution (5x) of medium B, C or D, respectively, is added to the fermentor in order to keep the carbon source concentration approximately at 1%. When the culture reaches an OD$_{600}$ of 60.0, the temperature is increased to 42° C. for at least 10 min and not more than 30 min, then lowered to 39° C. or 40° C. for 2.5 hours. The cells are then harvested by centrifugation and frozen at either −20° or −70° C. until processed.

TABLE 1

| Constituent | g/L |
| --- | --- |
| Medium A: LB Medium | |
| NaCl | 10 |
| tryptone | 10 |
| yeast extract | 5 |
| kanamycin or ampicillin | 5 × 10$^{-3}$ |
| Medium B | |
| NH$_4$Cl | 4.5 |
| KH$_2$PO$_4$ O | 0.76 |
| MgSO$_4$ 7H$_2$O | 0.18 |
| K$_2$SO$_4$ | 0.09 |
| CaCl$_2$. | 24 × 10$^{-3}$ |
| FeSO$_4$ 7H$_2$O | 7.6 × 10$^{-3}$ |
| Trace Elements | 0.5 ml |
| casamino acids | 25 |
| yeast extract | 5 |
| glucose or glycerol | 20 |
| kanamycin or ampicillin | 5 × 10$^{-3}$ |
| Medium D | |
| (NH$_4$)SO$_4$ | 5.6 |
| K$_2$HPO$_4$ | 6.7 |
| MgSO$_4$.7H$_2$O | 7.8 |
| NaH$_2$PO$_4$.H$_2$O | 3.8 |
| EDTA | 0.98 |
| Trace Elements | 1 ml |
| yeast extract or NZ Amine | 50 |
| glucose or glycerol | 20 |
| kanamycin or ampicillin | 5 × 10$^{-3}$ |

EXAMPLE 2

Assembly and Expression of the SLPIII Gene

1. Summary of the scheme for assembling the SLPIII gene.

SLPIII closely resembles the silk fibroin molecule because it includes the amino acid tyrosine at regular intervals (about 60 residues). The SLPIII gene was assembled from smaller parts. First, three doublestranded sections of DNA of about 60 bp in length were chemically synthesized. Each section was cloned by insertion into bacteriophage M13 and the DNA sequence was verified. These sections were then removed from the vector and linked together in a specific order. This linkage of about 180 bp is named the SLPIII "monomer". "Monomers" were then linked in a specific order to yield dimers, trimers, tetramers, etc., of SLPIII. The multimers were then cloned either directly into plasmid expression vectors to detect the SLPIII protein or initially into an adapter plasmid. Insertion of the SLPIII DNA into the adapter allows for further gene manipulation and is further described later. The assembly scheme is pictured as follows:

Synthesis of double-stranded DNA sections—

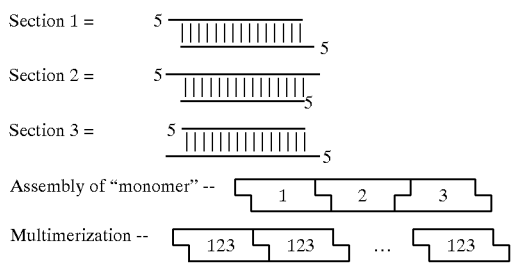

The DNA and corresponding amino acid sequences of the three sections of the SLPIII gene are shown in the following Table 1.

TABLE 1

```
GGT GCC GGC AGC GGT GCA GGA GCC GGT TCT GGA GCT
CCA CGG CCG TCG CCA CGT CCT CGG CCA AGA CCT CGA
 G   A   G   S   G   A   G   A   G   S   G   A

GGC GCG GGC TCT GGC GCG GGC GCA G            (SEQ ID
                                              NO:22)
CCG CGC CCG AGA CCG CGC CCG CGT CCT AG       (SEQ ID
                                              NO:23)
 G   A   G   S   G   A   G   A   G   S       (SEQ ID
                                              NO:24)

GA TCC GGC GCA GGC GCT GGT TCT GGC GCA GGG GCA
   G CCG CGT CCG CCA AGA CCG CCG CGT CCC CGT
   G   S   G   A   G   A   G   S   G   A   G   A

GGC TCT GGC GCA GGA GCG GGG TCT GGA GCT GCA (SEQ ID
                                             NO:25)
CCG AGA CCG CGT CCT CGC CCC AGA CCT CG      (SEQ ID
                                             NO:26)
 G   S   G   A   G   A   G   S   G   A   A (SEQ ID
                                             NO:27)

GGC TAT GGA GCT GGC GCT GGC TCA GGT GCT
 A CGT CCG ATA CCT CGA CCG CGA CCG AGT CCA CGA
    A   G   Y   G   A   G   A   G   S   G   A

GGA GCA GGA AGC GGA GCG GGT GCC A           (SEQ ID
                                             NO:28)
CCT CGT CCT TCG CCT CGC CCA CGG TTC GA      (SEQ ID
                                             NO:29)
 G   A   G   S   G   A   G   A             (SEQ ID
                                             NO:30)
```

The double-stranded DNA sequence is shown in the 5' to 3' direction. The amino acids (g=glycine, a=alanine, s=serine, y=tyrosine) coded by the sequence are shown immediately below each section.

The above six single-strands were synthesized. After synthesis, the strands of DNA were purified and the homologous strands were annealed. About L μl (0.5 μg) of each strand was mixed with 2 μl of 10X AA (10XAA defined in Example 1, section 8), buffer and 16 μl of sterilized deionized $H_2O$ in a 1.5 ml polypropylene Eppendorf tube. The tube was placed in a boiling water bath (500 ml in a 1 liter beaker) for 10 min and then the beaker was removed from the hot plate and allowed to cool on the bench to room temperature. This required about 1–2 hr.

Each of the three double-stranded sections was cloned separately into M13mp18. Section 1 was ligated between the SmaI and BamHI restriction sites of the multiple-cloning site. Section 2 was ligated between the BamHI and PstI sites. And section 3 was inserted between the PstI and HindIII sites. The respective clones are: M13mp18.1, M13mp18.2, M13mp18.3. The DNA sequence was determined for each cloned section. One representative of each section that had the correct DNA sequence was recovered and became the material for the next step: assembly of the "monomer".

2. Assembly of the "monomer" of SLPIII.

The DNA sections 2 and 3 were isolated by digestion of the M13 clones with restriction enzymes: for section 2, M13mp18.2 was digested with BamHI and PstI; for section 3, M13mp18.3 was digested with PstI and HindIII. The two sections were purified and mixed together in equal molar amounts with M13mp18.1 that had been first digested with BamHI and HindIII. $T_4$ DNA ligase was added to link the homologous overlapping ends in the order 1-2-3. Due to the hybridization specificity of the cohesive ends, the three sections are efficiently linked in only this order. The DNA sequence of the cloned "monomer" in the assembly named M13mp18.1.2.3 was determined to be correct and as shown in Table 1 above.

3. Multimerization of the "monomer" of SLPIII.

In order to prepare large amounts of the "monomer" structural gene we first subcloned the "monomer" into the plasmid vector pUC12. M13mp18.1.2.3 was digested with EcoRI and HindIII restriction enzymes. The SLPIII "monomer" was gel purified and ligated into pUC12 digested with EcoRI and HindIII. The resulting plasmid DNA was prepared, the "monomer" was released from the vector by digestion with BanI REN and the fragment was gel purified.

To create multimers, "monomer" DNA with BanI ends were linked by ligation. The nonpalindromic terminal BanI recognition sequence allows linkage only in a head-to-tail order. The extent of multimerization is monitored by gel electrophoresis and staining the DNA with ethidium bromide. Multimers of more than 20 units were obtained by this method.

4. Cloning of the multimers of SLPIII. Plasmid pCQV2 (Queen et al., J. Appl. Mol. Gen., 2:1–10 (1983)) was digested with EcoRI and BamHI restriction endonucleases and a fragment of about 900 bp was purified. This DNA fragment contains the bacteriophage lambda cI-857 repressor gene, the closely linked rightward promoter, $P_R$, and the beginning of the cro gene. Plasmid pSY335 (described as pJF751 in Ferrari et al., J. Bacteriology, 161:556–562 (1985)) was digested with EcoRI and BamHI restriction enzymes and subsequently ligated to the DNA fragment of approximately 900 bp of pCQV2. The plasmid obtained from this construction, pSY751, expresses the β-galactosidase gene at 37° C. and 42° C., but not at 30° C.

In this approach the SLPIII gene is first cloned into an "adapter" sequence in an intermediate plasmid and then subcloned to the expression systems. The adapter sequence has the following useful features: a unique central BanI REN site, three unique REN sites to either side of BanI, information coding for protein cleavage at either methionine, aspartate-proline or arginine amino acids and small size. The BanI site is the point of insertion for the SLPIII multimers with BanI ends.

The adapter was synthesized with the Applied Biosystems 380A Synthesizer, cloned in M13mp18 and the DNA sequence verified. The adapter was then subcloned into a specially-constructed plasmid vector that lacked BanI REN sites. The recipient plasmid was made as follows. Plasmid pJH101 (Ferrari et al., 1983) was partially digested with AhaIII restriction enzyme and religated. Transformants of *E. coli* HB101 were selected on medium containing chloramphenicol (12.5 mg/ml). After restriction analysis of several isolates one plasmid was chosen, pSY325. This plasmid contains only the chloramphenicol-resistance gene and the replication origin (from pBR322) of pJH101. After digestion to completion with XhoII, pSY325 was ligated with the gel-purified adapter. The result was the adapter-plasmid, pSY937, and its new REN sites were verified.

The SLPIII multimers were cloned into the BanI site of pSY937. Positive clones were identified by colony hybridization and with the lower strand of section 1 of SLPIII as the DNA probe for hybridization (probe sequence shown in Table 1). Positive clones were characterized by gel electrophoresis for the size of the inserted multimer. Finally, the SLPIII sequences were subcloned using the REN site in the flanking adapter regions to specific locations of expression plasmids.

The SLPIII protein had the following amino acid composition:

```
SLPIII      1178 AA           MW 83,000
(fm) DPVVLQRRDWENPGVTQLNRLAAHPPFASDPM
     GAGS(GAGAGS)_6 GAAGY
     [(GAGAGS)_9 GAAGY]_18
     GAGAGSGAGAGSGAGAMDPGRYQLSAGRYHYQLVWCQK
     (SEQ ID NO:31)

(fm) intends the initiation codon
```

SLPIII Expression Vector

Plasmid DNA pSY1086 is a pSY937 derivative containing 19 repeats of SLPIII (3.5 kb). This plasmid DNA was digested with NruI and PvuII and the fragments separated by agarose gel electrophoresis. The purified SLPIII multimer was then cloned in plasmid pSY751 digested with PvuII REN. Several clones were analyzed and one (pSY1008) was chosen to be used in expression experiments and SLPIII purification.

The ampicillin drug resistance gene of pSY1008 was substituted with the kanamycin marker from pSY1010 (produced by digestion of pSY633 with DraI and SspI and insertion of Kan$^R$ obtained by HincII digestion of pUC4K) and the subsequent plasmid was called pSY1186. By removing the SLPIII portion of plasmid pSY1186 with BanI, a new plasmid, pSY1262, was generated. This plasmid contains a unique BanI site which allows for the direct ligation of fragments containing BanI ends obtained by polymerization of monomers. This plasmid has been used to generate plasmids containing inserts for the following proteins: SELP1, 2, 3, and SLP4.

Production and Purification of SLPIII

Cell Culture. *E. coli* are cultured in one of the following media:

| Medium C | |
|---|---|
| Constituent | g/l |
| yeast extract | 20 |
| casamino acids | 20 |
| peptone | 20 |
| gelatin peptone | 20 |
| KH$_2$PO$_4$ | 2 |
| K$_2$HPO$_4$ | 2 |
| Na$_2$HPO$_4$ 7H$_2$O | 2 |
| glucose or glycerol | 2 |
| kanamycin or ampicillin | 0.1 |

An overnight culture (500 ml–1 L) which had been grown at 30° C. was used to inoculate 375 L of media contained in a 500 L fermentor. Fermentor conditions include a tachometer reading of 100 rpm, vessel back pressure of 5 psi and an air flow of 170 l/min in order to maintain dissolved O$_2$ at greater than 50%.

Glucose (1 gm/l) and ampicillin (0.05 g/l) were added to the fermentation when the culture reached an OD$_{650}$ of 1.0 and again at 2.0. When the culture reached an OD$_{650}$ of 2.0 the temperature was increased to 42° C. for 10 min and then lowered to 38° C. for 2 hours. The culture was then chilled to 10° C. and cells were harvested by centrifugation in a continuous centrifuge and frozen at –70° C. until processed. Yields from two separate fermentations were 7.3 kg and 5.2 kg wet weight of cells.

It should be noted that other media can be used and, with different plasmids, various selection conditions can be imposed (i.e., substitution of kanamycin selection for ampicillin). These conditions have been used in laboratory scale fermentations (10 L volumes).

Cell Lysis.

Method 1.

Cells are thawed and suspended to a concentration of 1 kg wet weight/6 1 in 50 mM Tris-HCl pH 7.0, 1 mM EDTA and broken by 2 passages through an APV Gaulin cell disrupter at 8000 psi. During this lysis procedure the cells are kept cold with an ice bath. The cell lysate is then centrifuged at 26,000xg with a continuous centrifuge, such as the TZ-28 rotor in a Sorvall RC5B refrigerated centrifuge operated at 4° C. Under these conditions greater than 90% of the SLPIII produced can be found in the pellet. The supernate does contain some product which can be recovered by NH$_4$SO$_4$ precipitation as described below. The pellet is extracted with LiBr as described below.

Method 2.

Frozen cells are thawed and resuspended to a concentration of 1 kg wet weight/6 1 in 50 mM Tris-HCl pH 7.0, 10 mM EDTA, and 5 mM PMSF to inhibit protease activity. Cells are stirred in this buffer at room temperature for 0.5 to 2 hours, then lysozyme is added to a concentration of 1 g/l and incubation is continued for 20 min. β-Mercaptoethanol is then added to 70 mM and the detergent NP40 is then added to a final concentration of 1% for 20 min while continuously stirring the cell suspension. The MgCl$_2$ is added to 50 mM followed by DNAse at a concentration of 1 mg/l and incubation is continued at room temperature for 20 min. The cell lysate is then centrifuged as in method 1 at 26,000xg in a continuous centrifuge and the supernatant is collected and passed through the continuous centrifuge a second time at 26,000 xg. The supernate resulting from this second centrifugation contains <5% of the total SLPIII, but what is there can be recovered with $NH_4SO_4$ as described below. The pellets resulting from the 1st and 2nd 26,000 xg centrifugations are combined and extracted with LiBr as described below.

Method 3.

For this method, a strain of E. coli is used that contains a second plasmid which encodes the T7 phage lysozyme. This plasmid is compatible with the plasmid encoding the SLPIII gene and the drug resistance determinant. The strain is grown in the same medium and under the same conditions as in the first two methods. However, due to the production of the T7 lysozyme inside the cells, their cell wall is weakened and they can be easily lysed at the completion of the fermentation by the addition of EDTA to >100 mM and NP40 to a concentration of from 0.5 to 1.0% v/v. Lysis can also be achieved by the addition of chloroform (20 ml per liter) of fermentation broth instead of NP40. Alternatively, cells may be collected by centrifugation prior to lysis, resuspended to 1 kg wet weight/6 1 in Tris-EDTA as described in the first two methods and then lysed by the addition of NP40 or chloroform. Following cell lysis by either method, the lysate is centrifuged in a continuous rotor at 26,000 xg as described in the first two methods. As with those methods, LiBr extraction of the pellet and $NH_4SU_4$ precipitation of the supernate are used to recover the product.

Purification of SLPIII

The pellet obtained by centrifugation of the cell lysate at 26,000 xg as described above is extracted with an equal volume of 9M LiBr. The salt solution is added and the pellet is evenly suspended by stirring at room temperature (RT). The mixture is stirred for 1 hour at RT after an even suspension is obtained. The mixture is then centrifuged at 26000 xg in a continuous rotor at 4° C. or at RT to generate a pellet and a supernatant fraction. The supernate is saved and the pellet is re-extracted with another equal volume of 9 M LiBr as above. After mixing for 1 hour, the mixture is centrifuged at 26,000 xg and the supernate from this centrifugation is combined with the supernate from the first LiBr extraction and allowed to stand at 4° C. overnight. Approximately 90% of the SI-PIII contained in the cell lysate 26,000 xg pellet is extracted by LiBr using this procedure.

After the LiBr extract stands overnight at 4° C. a precipitate forms, which is removed by centrifugation at 26,000 xg and is discarded. The supernate is then placed in dialysis bags and dialyzed against several changes of $dH_2O$ for 2 days. As the LiBr is removed by dialysis the SLPIII product precipitates in the dialysis bags. The precipitate is collected by centrifugation and washed 2 to 3 times with $dH_2O$. The final washed product is centrifuged and dried by lyophilization.

For the recovery of SLPIII from the 26,000xg supernatant fractions, $NH_4SO_4$ precipitation is used. Solid $NH_4SO_4$ is slowly added to the sample which is maintained at 4° C., until 38% saturation is achieved (231 g/l). The mixture is then stirred at 4° C. for 2 to 3 hours. The precipitate is recovered by centrifugation in a continuous flow centrifuge and washed 4 to 5 times with an equal volume of distilled $H_2O$ or with 0.5% SDS in $H_2O$. After each wash, the precipitate is recovered by continuous centrifugation. The pellet becomes increasingly white with successive washes as contaminating protein is removed. SLPIII is recovered as a washed pellet and can be dried by lyophilization.

Trypsin Treatment Step of SLPIII

SLPIII was suspended in 50 mM Tris-HCl, pH 8.0, 0.1 M NaCl buffer, and was placed in a 37° C. water bath, and TPCK treated trypsin solution was mixed into the suspension. The final trypsin concentration was 0.1%. After 3 hours, the solution was centrifuged at 16,000xg for 15 min., the pellet was washed with a half equal volume of 0.5% SDS in $H_2O$ first, then with distilled water. After each wash the pellet was recovered by centrifugation. The final product was resuspended in water and kept at 4° C. for further analysis.

With the trypsin treatment, SLPIII was purified to 99.4% purity.

Physical Measurements of SLPIII

Physical measurements of the purified silklike proteins have been compared with those of Bombyx mori silk in order to establish that the repetitive amino acid polymers produced microbiologically accurately mimic the properties of naturally occurring polymers. Physical measurements were performed to confirm the model of anti-parallel chain pleated sheet conformation for the crystalline regions of Bombyx mori silk fibroin (Marsh, Corey and Pauling, Biochem. Biophys. Acta (1955) 16; Pauling and Corey, Proc. Natl. Acad. Sci. USA (1953) 39:247). Preliminary analysis of x-ray diffraction patterns obtained from SLP films are consistent with those described by Fraser, MacRai, and Steward (1966) (Table 2). Circular Dichroic (CD) and Fourier transform infrared (FTIR) spectroscopic analysis of SLPIII are consistent with a high degree of extended β and β-turn conformations. Comparisons of the spectra obtained from SLPIII with that of naturally occurring silk fibroin in various solvents (Isuka and Young, Proc. Natl. Acad. Sci. USA (1966) 55:1175) indicate that SLPIII in solution consists of a mixture of the random and highly ordered structures seen in silk fibroins.

This data demonstrates that SLPIII contains extended β strands that are capable of packing into highly crystalline domains. The data also reveals the presence of distinct β-turn (reverse turn) conformations. A computer analysis of the amino acid sequence of SLPIII using an algorithm for secondary structure prediction developed by Chou and Fasman (1974), infra, indicates that the AGYG sequence has a β-turn propensity.

TABLE 2

| Material | a (A) | b (A) | c (A) |
| --- | --- | --- | --- |
| $(AG)_n$ | 9.42 | 6.95 | 8.87 |
| $(AGAGSG)_n$ | 9.39 | 6.85 | 9.05 |
| CTP fraction | 9.38 | 6.87 | 9.13 |
| Native fibroin | 9.40 | 6.97 | 9.20 |
| SLPIII | 9.38 | 6.94 | 8.97 |

Referenced in Fraser et al., J. Mol. Biol. (1966) 19:580.

EXAMPLE 3

FCB-SLPIII Construction

Design

The SLPIII polymer (see above and also application Ser. No. 114,618, filed Oct. 29, 1987, a PCT/US/87/02822) was chosen because of its predicted structure, allowing for fabrication of useful products; having good structural properties for use in a wide variety of applications; having β-turn structures between interactive strands; and allowing for substitution of the turn sequences with other sequences. The fibronectin cell-binding domain, amino acids 1405–1512, has a strong turn propensity, with the tripeptide RGD providing for cell attachment, predicted to be present within a hydrophilic loop between adjacent β-strands. A 10 amino acid sequence spanning this proposed loop structure (referred to as fibronectin cell-binding or FCB sequence) was chosen to constitute the functional block of amino acids to be inserted within the SLPIII backbone. The insertion site within the SLPIII backbone was chosen to correspond with the amino-acid sequence GAAGY which is also predicted to provide a turn structure (Chou and Fassman (1974) *Biochemistry* 13:222–244). The design allows for conservation of the FCB structure while causing minimal disruption of the SLPIII $(GAGAGS)_9$ β-strand crystal-packing domains.

DNA Synthesis and Gene Construction

The SLPIII gene monomer contains a PstI restriction endonuclease site within the sequence encoding the proposed turn structure, GAAGY. This site was used to insert the synthetic DNA encoding the 10 amino acids of the FCB sequence. Two complementary DNA strands comprising the FCB site, 36 bases in length, were synthesized consisting of the sequence shown below:

```
                                       (SEQ ID NO:32)
  5'-GTGACTGGCCGTGGTGATAGCCCGGCTAGCGCTGCA-3'

(SEQ ID NO:33)
3'-ACGTCACTGACCGGCACCACTATCGGGCCGATCGCG-5'
```

These oligonucleotides were purified according to the procedures described in Example 1, and be cloned into the PstI site of pSY1304. pSY1304 contains a single monomer gene fragment of SLPIII. pSY1304 DNA was digested with PstI and ligated with a mixture of the FCB oligonucleotides. The ligation reaction products were transformed into *E. coli* cells. Colonies containing the plasmid were selected on bacterial culture plates containing the antibiotic chloramphenicol. Individual colonies were grown and plasmid DNA purified and analyzed for the presence of the FCB oligonucleotide sequence by restriction digestion with NheI. Plasmids containing this restriction site were subjected to DNA sequencing and two candidates were shown to be correct. The partial nucleotide sequence of one of these, pSY1325, and the encoded amino-acid sequence is shown as follows:

TABLE 3

```
    1                 15                   30
Ban I
1
GGT GCC GGC AGC GGT GCA GGA GCC GGT TCT GGA GCT GGC
    A   G   S   G   A   G   A   G   S   G   A   G
                    5                   10

45                  60                   75
                          Bam HI
                          1
GCG GGC TCT GGC GCG GGC GCA GGA TCC GGC GCA GGC GCT
A   G   S   G   A   G   A   G   S   G   A   G   A
      15                  20                   25

90                  105
GGT TCT GGC GCA GGG GCA GGC TCT GGC GCA GGA GCG GGG
G   S   G   A   G   A   G   S   G   A   G   A   G
               30                   35

120                  135                  150
             Pst I
             1
TCT GGA GCT GCA GTG ACT GGC CGT GGT GAT AGC CCG GCT
S   G   A   A   V   T   G   R   G   D   S   P   A
```

TABLE 3-continued

```
   40                    45                    50

165                   180
        Pst I
        1
AGC GCT GCA GGC TAT GGA GCT GGC GCT GGC TCA GGT GCT
S   A   A   G   Y   G   A   G   A   G   S   G   A
           55                    60

195                  210
                     Ban I
                     1
 GGA GCA GGA AGC GGA GCG GGT GCC (SEQ ID NO:34)
 G   A   G   S   G   A   G (SEQ ID NO:35)
65                    70
```

The FCB-SLP monomer gene fragment was purified from pSY1325 by digestion with BanI, agarose-gel electrophoresis, and NACS purification (Example 1, No. 11). The monomer gene fragment was self-ligated and cloned into pSY937 which had been digested with BanI. The products of this ligation were transformed into *E. coli* and selected for growth on chloramphenicol. Plasmid DNA from individual colonies was analyzed for inserts containing multiple FCB-SLP monomer fragments by digestion with NruI and EcoRV and electrophoresis on agarose gels. One clone was identified containing two inserts, one of approximately 2.1 kb and the other of 2.8 kb. Both inserts were cloned individually and transferred to the expression vector pSY751. Plasmid pSY1325 was digested with NruI and PvuII and the 2.1 and 2.8 kb insert bands were purified. These DNA fragments were ligated with pSY751 that had been digested with PvuII. The products of this reaction were transformed into *E. coli* and selected for growth on the antibiotic ampicillin. Plasmid DNA from individual colonies was analyzed by restriction digestion for the presence of the FCB-SLP polymer gene. Two clones were identified, pSY1520 and 1521, containing the 2.1 and the 2.8 kb inserts, respectively.

PSY1521 FCB-SLP Protein 980 AA MW 72,700
MDPVVLQRRDWENPGVTQLNRLAAHPPFASDPM
GAGS$(GAGAGS)_6$GAAVTGRGDSPASAAGY
$[(GAGAGS)_9$GAAVTGRGDSPSAAGY$]_{13}$
GAGAGSGAGAGSGAGAMDPGRYQLSAGRYHYQLVWCQK (SEQ ID NO:36)

Product Purification

*E. coli* cells containing pSY1520 and pSY1521 were grown at 30° C. in LB medium containing 50 μg/ml ampicillin to an $OD_{600}$ of 0.7. Production of the FCB-SLP polymer proteins were induced by increasing the culture temperature to 42° C. for 1.5 hrs. The cells were harvested by centrifugation and lysed in sample buffer containing sodium dodecylsulfate (SDS) and β-mercaptoethanol by heating at 100° C. for 5 min. Samples of these lysates corresponding to $5\times10^8$ cells were applied to an 8% polyacrylamide gel containing SDS, electrophoresed, and transferred to nitrocellulose filters by electroblotting. The filters were incubated either with anti-SLP or anti-FCB peptide antibody. Specific immunoreactivity with the anti-SLP antibody was observed for a protein band of approximately 75 kDal in lysates of pSY1520, 95 kDal in lysates of pSY1521, and 120 kDal in lysates of the SLPIII clone pSY1186. Reactivity with the anti-FCB antibody was observed only for the two FCB-SLP polymer bands.

*E. coli* containing pSY1521 was fermented at the 1 L level using the batch process conditions described in Example 1, except as follows: Medium C was employed, the fermentor was a 2L MBR with a working volume of 1L. The starting and final volume were the same, i.e. no medium was added. 25 g of wet-weight cells were harvested by centrifugation and disrupted by French pressing at 15,000 psi. The cell lysate was centrifuged at 16,000xg for 20 min, yielding a pellet fraction containing >90% of the FCB-SLP protein as determined immunologically. The pellet was washed several times with 50 mM Tris-HCl (pH 8.0), 150 mM NaCl, 1 mM EDTA and then extracted with 5 M LiBr. The supernatant phase of this extraction was dialyzed against deionized water resulting in the formation of a precipitate which was collected by centrifugation. The precipitate was re-extracted with 3 M LiBr and the dissolved proteins were selectively precipitated by 4-fold dilution with distilled water. The remaining supernatant was dialyzed against 10 mM Tris (pH-7.5), 1 mM EDTA, 1 mM PMSF. The precipitated protein was collected by centrifugation, resuspended in deionized water, and analyzed by amino acid composition. The composition of this semi-purified fraction showed it to be approximately 30% FCB-SLP as determined by compositional content of the amino acids present in this polymer. The ratio of these amino acids correlated closely with that predicted by the DNA sequence of the FCB-SLP polymer gene.

Assay of Biological Activity

In order to determine whether the FCB-SLP polymer protein exhibited cell attachment activity, semi-purified protein was immobilized on nitrocellulose filters and incubated with mammalian tissue-culture cells. Lysate proteins from *E. coli* cells containing pSY1520, pSY1521, or pSY1186 (the SLPIII-encoding plasmid) were electrophoresed on SDS-PAGE and transferred to nitrocellulose filters by electroblotting. These filters were tested for their ability to promote cell attachment using a modification of the procedure of Hayman et al. (1982) supra. The filters were washed in PBS (10 mM Na phosphate pH 7.4, 150 mM NaCl) several times with gentle agitation, and soaked in PBS containing 5% condensed milk for 1 hr. The filters were then either incubated with 5% condensed milk in PBS containing anti-SLP or anti-FCB serum (1:100 dilution of serum) or 5% condensed milk in PBS alone for 2 hr at 37° C. The filters were washed twice with PBS and incubated with cells. The cells were prepared by resuspension of subconfluent monolayers in 0.1% trypsin solution. The cells were incubated in DME medium containing 10% fetal calf serum at 0° C. for 30 min. The cells were centrifuged (except for H9 lymphocytes which were allowed to settle), washed in PBS, and finally resuspended in DME medium without serum at a density of $2.5 \times 10^6$ cells/ml. The filters were overlayed with the cell suspensions in flat plastic dishes and incubated at 37° C. in a $CO_2$ incubator for 1 hr. The filters were washed twice in PBS to remove unbound cells and fixed in 3% formaldehyde. The filters were stained with Amido black in 45% methanol, 10% acetic acid, 45% water for 3 min and destained in 90% methanol, 2% acetic, 8% water.

By visual inspection, the filter incubated with Vero cells (African green monkey kidney epithelial cells) contained heavily stained regions. These regions corresponded to the positions of the FCB-SLP protein bands as determined by reactivity to parallel filters with anti-SLP and anti-FCB antibody. Microscopic inspection of these same areas of the filters showed that the heavy staining was due to the attachment of cells. No cells above background were bound to any other area of the filters including other *E. coli* lysate protein bands. Cells were not attached to the filter at the region corresponding to the SLPIII protein band. As expected, when incubated with H9 lymphocytes, no specific binding of cells to the filter was observed.

In order to determine the effect of protein concentration and various pretreatments of filters and cells with specific antibodies on cell attachment, a dot-blot cell-binding assay was developed. The assay was performed as described above except that semipurified FCB-SLP and SLPIII protein of known concentration was applied directly to nitrocellulose filter dots using a Schleicher and Schuell dot-blot manifold. Each sample was applied such that the first dot in a series contained 10 μg of protein and subsequent dots contained serial two-fold dilutions of this sample. Both the 75 kDal and the 95 kDal FCB-SLP proteins from pSY1520 and 1521, respectively, promoted Vero cell attachment at low concentration. The minimum amount of the 75 kDal FCB-SLP protein required to promote cell attachment was 0.05 $\mu g/cm^2$. For the 95 kDal FCB-SLP protein, the minimum was 0.2 $\mu g/cm^2$. Few cells were attached to the SLPIII-containing dots even at 12.5 $\mu g/cm^2$. Cell attachment to the FCB-SLP protein was inhibited by preincubation of the filter with anti-FCB or anti-SLP antibody. Cell attachment was inhibited but not abolished by preincubation of the cells with FCB peptide at a concentration of 300 μg/ml.

The introduction of the 10 amino acids of FCB into the SLPIII monomer sequence creates a protein polymer whose purification and solubility characteristics are not appreciably different from those of the SLPIII protein polymer, while gaining the additional property of the ability to promote cell attachment. The subject protein polymers may be formulated, either singly or in combination, with other compounds or protein polymers, synthetic or natural polymers, into fibers and films that promote cell attachment. The biological activity of FCB-SLP is chemically resistant to denaturation. Cell attachment occurs to the FCB-SLP proteins after treatment with high concentrations of detergent at 100° C., as well as with chaotropic denaturants. This stability facilitates the sterilization methods used in the preparation of bioactive materials. Solid-support cell-attachment matrices for enhancing the growth and differentiation of cells and tissue culture is a direct application of such materials. The subject polymers may be easily deposited onto other materials or substrates to provide for a cell-binding surface. Cell-attachment polymers in various forms, e.g., fibers, membranes, films, etc. may be used in bioreactors to suspend production cells within gently mixing liquid growth medium, increasing exposure to nutrients while decreasing cell damage to vigorous agitation. The subject material may be made into or coated on woven fabrics, films or membranes and used as wound-dressings that promote enhanced healing due to the attachment of cells involved in the healing process. In addition, the subject proteins may be formulated into or deposited onto the walls of prosthetic devices intended for in vivo replacement of blood vessels, bone joints, tendons, ligaments, or the like, in order to promote in vitro and/or in vivo colonization of the device, thus improving its functional properties. In addition, the subject proteins may find application in the eye, as implants, carriers, coatings or the like.

SLP3-Cys (SLP-C)

Design of a chemically active cross-linkable polymer.

Many amino acids contained within a protein chain can be chemically modified using specific organic and inorganic reagents. Some of these amino acids include lysine (K), arginine (R), glutamate (E), aspartate (D), cysteine (C), serine (S), threonine (T), histidine (H), and tyrosine (Y). In order to create a protein polymer upon which specific reactions could be performed for the purpose of adding additional molecules to the chain at specific locations or to link chains of the same or different polymers together, or to link chains to a suitable surface, SLP-C was designed. The 59 amino acid silk-like monomer of SLP3 was modified to include the amino acid sequence GAGCGDPGKGCCVA. Features of the inclusion sequence are: 1. the GAGC and GCCV tetrapeptides conform with the β-strand structure of the flanking silk-like amino acids and contain cysteines whose sulfhydryls are reactive under oxidation and can be covalently crosslinked, 2. the DPGK does not conform with the β-strand structure therefore forcing an unaligned structure within the silk-like strands. This latter sequence further has the advantage of providing two additional chemically modifiable residues, aspartate and lysine, and contains the dipeptide DP which is susceptible to specific chemical peptide cleavage.

Polymer Construction

Two oligonucleotide strands were synthesized and purified as described in Example 1.

```
        PstI         SmaI
1) 5'-GGAGCAGGTTGTGGCGATCCCGGGAAAGGA        (SEQ
                    TGCTGTGTAGCTGGTGCA-3'    ID
                                             NO:37)

2) 3'-ACGTCCTCGTCCAACACCGCTAGGGCCCTT         (SEQ
                    TCCTACGACACATCGACC-5'    ID
                                             NO:38)
```

The two oligonucleotide strands were annealed and ligated with the DNA of plasmid pSY1304 (SLP3 monomer in pSY937) which had been digested with PstI REN.

The product of this ligation reaction was transformed into E. coli strain HB101. Plasmid DNA from transformants was purified and digested with BanI; clones containing inserts of the correct size were digested with PstI and EcoV RENs for the determination of orientation. Plasmid DNA from correct clones was sequenced. Plasmid pPT0103 (shown in Table 4) contained the desired SLP-C monomer sequence, oligonucleotides (1) and (2) are shown below in bold and underlined.

purified fragment was ligated with plasmid pSY1262 which had been digested with REN BanI. The product of this ligation reaction was transformed into E. coli strain HB101. Transformants were selected for resistance to kanamycin. Plasmid DNA from individual transformants was purified and analyzed for increase in size due to SLP-C multiple DNA insertion. Several clones were obtained ranging in size from approximately 1.0 kbp to 5.4 kbp. Six clones (pPT0105 to pPT0110) were chosen to be used for expression of SLP-C.

Expression An overnight culture which had been grown at 30° C. was used to inoculate 50 ml of LB media contained in a 250 ml flask. Kanamycin was added at a final concentration of 50 μg per ml and the culture was incubated with agitation (200 rpm) at 300C. When the culture reached an $OD_{600}$ of 0.8, 40 ml were transferred to a new flask prewarmed at 42° C. and incubated at the same temperature for approximately 2 hours. The cultures (30° C. and 42° C.) were chilled on ice and $OD_{600}$ was taken. Cells were collected by centrifugation, divided in 1.0 $OD_{600}$ aliquot and used to perform dot blot and western analysis using SLP antibodies (see Example 1). For purification and amino acid analysis, larger cultures were used.

Analysis

E. coli strain HB101 containing plasmid pPT0105 was grown at 30° C. to an $OD_{600}$ of 0.7 and then shifted to 42° C, after the addition of 40 μCi per ml of $^{35}$S-Cysteine, for 2.0 hours. The proteins produced by these cells were analyzed

TABLE 4

```
    G   A   G   S   G   A   G   A   G   S   G   A   G   A   G   S   G
5'-GGTGCCGGCAGCGGTGCAGGAGCCGGTTCTGGAGCTGGCGCGGGCTCTGGC
3'-CCACGGCCGTCGCCACGTCCTCGGCCAAGACCTCGACCGCGCCCGAGACCG

A   G   A   G   S   G   A   G   A   G   S   G   A   G   A   G   S   G
GCGGGCGCAGGATCCGGCGCAGGCGCTGGTTCTGGCGCAGGGGCAGGCTCTGGC
CGCCCGCGTCCTAGGCCGCGTCCGCGACCAAGACCGCGTCCCCGTCCGAGACCG

A   G   A   G   S   G   A   A   G   A   G   C   G   D   P   G   K   G
GCAGGAGCGGGGTCTGGAGCTGCAGGAGCAGGTTGTGGCGATCCCGGGAAAGGA
CGTCCTCGCCCCAGACCTCGACGTCCTCGTCCAACACCGCTAGGGCCCTTTCCT

C   C   V   A   G   A   G   Y   G   A   G   A   G   S   G   A   G   A
TGCTGTGTAGCTGGTGCAGGCTATGGAGCTGGCGCTGGCTCAGGTGCTGGAGCA
ACGACACATCGACCACGTCCGATACCTCGACCGCGACCGAGTCCACGACCTCGT

G   S   G   A                                          (SEQ ID NO:39)
GGAAGCGGAGCG-3'                                        (SEQ ID NO:40)
CCTTCGCCTCGC-5'
```

Plasmid DNA from pPT0103 was digested with BanI REN and the digestion fragments were separated by agarose gel electrophoresis. The SLP-C gene fragment, 225 bp, was excised and purified by NACS column (see Example 1. The by SDS-PAGE for detection of $^{35}$S-Cysteine and reactivity to SLP antibodies (see Example 1). In both analyses a strong reactive band was observed with an apparent molecular weight of approximately 150 kDal.

```
PPT0105    SLP-C Protein    1333AA    MW 97,000        (SEQ ID NO:41)
MDPVVLQRRDWENPGVTQLNRLAAHPPFASDPMGAGS(GAGAGS)_6

[GAA(GAGCGDPGKGCC)VAGAGY(GAGAGS)_9]_{16}

GAAGAGCGDPGKGCCVAGAGY(GAGAGS)2GAGAMDPGRYQLSAGRYHYQLVWCQK
```

SLP3-Laminin Cell Binding (SLP-L)

Design of a biologically active polymer for attachment of nerve cells.

The amino acid sequence of human laminin B1, a protein component of some extracellular basement membranes upon which cells attach and proliferate, contains a pentapeptide, YIGSR, which has been implicated in providing a receptor attachment site for nerve cells. Two silk-like polymers, one containing a 12 and the other a 14 amino acid sequence each including the pentapeptide were designed. In the first polymer designated SLP-L1, the 59 amino acid monomer of SLP3 was interrupted near its tyrosine residue with the inclusion of the sequence YCEPGYIGSRCD. In SLP-L2 the inclusion sequence was LCVSEPGYIGSRCD. Since they do not conform to β-strand structure, both sequences when embedded within the β-strand structure of the silk-like strands should form unaligned loops. SLP-L1 and SLP-L2 are designed to provide a synthetic substrate for the attachment of nerve cells both in culture and in vivo. The formulation of these polymers into nerve conduits for the regeneration of injured nerves is one possible application.

Construction of SLP-L1.

Two oligonucleotide strands were synthesized and purified as described in the Example 1.

```
        PstI        SmaI
i)   5'-     GTATGTGAACCCGGGTATATCGGTAGCCGTTGCGATGCA-3'   (SEQ ID NO:42)

ii)  3'-ACGTCATACACTTGGGCCCATATAGCCATCGGCAACGCT -5'       (SEQ ID NO:43)
```

These oligonucleotide strands were annealed and ligated with plasmid pSY1304 (see WO 88/03533, page 65) which had been digested with PstI REN.

The product of this ligation reaction was transformed into *E. coli* strain HB101. Plasmid DNA from transformants was purified and digested with BanI; clones containing inserts of the correct size were digested with PstI and EcoRV RENs to determine the correct orientation. Plasmid DNA from correct clones was sequenced. Plasmid pTO120 (shown in Table 5) contained the desired SLP-L1 monomer sequence, oligonucleotides (i) and (ii) are shown below in bold and underlined.

had been digested with REN BanI. The product of this ligation reaction was transformed into *E. coli* strain HB101. Transformants were selected for resistance to kanamycin. Plasmid DNA from individual transformants was purified and analyzed for increase in size due to SLP-L1 multiple DNA insertion. Several clones were obtained ranging in size from 1 kbp to 4 kbp. One clone pPT0123, with an insert of approximately 2.4 kbp was chosen for expression and protein analysis.

Construction of SLP-L2

An additional two oligonucleotide strands were synthesized as described in Example 2.

```
iii) 5'-              CTGTGTGTTAGC  -3' (SEQ ID NO:46)

iv)  3'- ACGTGACACACAATCGCTTGGG  -5' (SEQ ID NO:47)
```

These oligonucleotide strands were annealed and ligated with plasmid pPTO126 (this plasmid was constructed from pPT 0125, see construction of CLP monomer in which the SLP-L1 monomer had been transferred) which had been digested with PstI and SmaI RENs. Plasmid DNA from transformant colonies resistant to chloramphenicol was purified. One plasmid, pPT 0121, (see Table 6) which was not digestible with REN PstI, was sequenced and proven to be the desired SLP-L2 monomer gene fragment. The oligonucleotide strands (iii) and (iv) are shown below in bold and underlined.

Expression of SLP-Polymers.

An overnight culture which had been grown at 30° C. was used to inoculate 50 ml of LB media contained in a 250 ml flask. Kanamycin was added at a final concentration of 50 μg per ml and the culture was incubated with agitation (200 rpm) at 30° C. When the culture reached an OD$_{600}$ of 0.8, 40 ml were transferred to a new flask prewarmed at 42° C. and incubated at the same temperature for approximately 2 hours. The cultures (30° C. and 42° C.) were chilled on ice

TABLE 5

```
    G   A   G   S   G   A   G   A   G   S   G   A   G   A   G   S   G
5'-GGTGCCGGCAGCGGTGCAGGAGCCGGTTCTGGAGCTGGCGCGGGCTCTGGC
3'-CCACGGCCGTCGCCACGTCCTCGGCCAAGACCTCGACCGCGCCCGAGACCG

A   G   A   G   S   G   A   G   A   G   S   G   A   G   A   G   S   G
GCGGGCGCAGGATCCGGCGCAGGCGCTGGTTCTGGCGCAGGGGCAGGCTCTGGC
CGCCCGCGTCCTAGGCCGCGTCCGCGACCAAGACCGCGTCCCCG-CCGAGACCG

A   G   A   G   S   G   A   A   V   C   E   P   G   Y   I   G   S   R
GCAGGAGCGGGGTCTGGAGCTGCAGTATGTGAACCCGGGTATATCGGTAGCCGT
CGTCCTCGCCCCAGACCTCGACGTCATACACTTGGGCCCATATAGCCATCGGCA

C   D   A   G   Y   G   A   G   A   G   S   G   A   G   A   G   S   G   A       (SEQ ID NO:44)
TGCGATGCAGGCTATGGAGCTGGCGCTGGCTCAGGTGCTGGAGCAGGAAGCGGAGCG-3'   (SEQ ID NO:45)
ACGCTACGTCCGATACCTCGACCGCGACCGAGTCCACGACCTCGTCCTTCGCCTCGC-5'
```

Plasmid DNA from pPT0120 was digested with BanI REN and the digestion fragments were separated by agarose gel electrophoresis. The SLP-L1 gene fragment, 216 bp, was excised and purified by NACS column (see Example 1). The purified fragment was ligated with plasmid pSY1262 which and OD$_{600}$ was taken. Cells were collected by centrifugation, divided in 1.0 OD$_{600}$ aliquot and used to perform dot blot and western analysis using SLP antibodies (see Example 1). For purification and amino acid analysis larger cultures were used.

```
pPT0123      SLP-L1 Protein      777 AA     M 60,300
MDPVVLQRRDWENPGVTQLNRAAAHPPFASDPMGAGS(GAGAGS)₆
[GAAVCEPGYIGSRCDAGY(GAGAGS)₉]₉
GAAVCEPGYIGSRCDAGY(GAGAGS)₂GAGAMDPGRYQLSAGRYHYQLVWCQKA       (SEQ ID NO:48)

pPT0150      SLP-L2 Protein      649AA      MW 51,000
MDPVVLQRRDWENPGVTQLNRLLLHPPFASDPMGAGS(GAGAGS)₆
[GAALCVSEPGYIGSRCDAGY(GAGAGS)₉]₇
GAALCVSEPGYIGSRCDAGY(GAGAGS)₂GAGAMDPGRYQLSAGRYHYQLVWCQKA     (SEQ ID NO:49)
```

*E. coli* strain HB101 containing plasmid pPTO123 or pPTO150 were grown as described above. The proteins produced by these cells were analyzed by SDS-PAGE for detection of reactivity to SLP antibodies (see Example 1). In both analyses a strong reactive band was observed of an apparent molecular weight of 90 kD and 68 kD respectively.

CLP AND CLP-CB

The design of a collagen-like polymer with thermoreversible gelation character.

Chemically hydrolyzed natural collagen can be denatured and renatured by heating and cooling to produce gelatin which is used in photographic and medical applications, among other applications. The chain property of collagen responsible for this phenomenon is its ability to spontaneously form interchain aggregates having a conformation designated as a triple helix. The helices are stabilized by weak interactions between chains arising from the close proximity of the peptide backbone at locations every third residue occupied by glycine and kinks provided by proline and hydroxyproline at the two positions between glycines. The geometry of the three kinked chains allows for hydrogen bonding within the triple helix. The structure is loose and is readily accessible to the interaction with water, small organic and inorganic molecules, other proteins, and cells. Although collagen consists of many different amino acid sequences one of the more structurally stable segments exists at the amino and terminal ends of the processed collagen chains. These ends consist almost exclusively of the repeating tripeptide sequence GPP (the second P is often hydroxylated). The collagen-like polymer CLP was designed predominantly of repeating GPP tripeptides (8 within each monomer segment). Other tripeptides were included in order to decrease the overall repetitiveness of the gene and to allow the use of additional codons which could be used to better manipulate the DNA. These were GAP (twice), GPA, GPV, and GSP. All of these triplets occur in natural collagen although never in the sequence and context used in CLP. The properties of CLP were designed to yield a protein polymer that would undergo thermoreversible gelation at high temperatures, as well as being nonimmunogenic. The high stability of the helices should create high tensile strength in fibers or membranes formulated from CLP. These chain properties should allow the creation of hydrogel colloids in aqueous solutions which when applied to hard substrates should act as soft coatings. Because of the simple sequence of CLP, its optical absorbance should be minimal in all wavelengths down to 220 nm.

The design of a soft coating material with cell attachment function.

The versatile formulation properties of collagen-like polymers makes them ideal as biomaterials used in implantable devices. Either as a coating on the surface of prostheses or as a structural component of the device itself, CLP could promote tissue integration by providing improved blood and cellular interaction. The latter function is mediated in natural collagen by a specific amino acid sequence which acts as a ligand for a cellular receptor. In order to create a CLP polymer with cell attachment activity, the sequence GLPG-PKGDRGDAGPKGADGSP (SEQ ID NO:50) was included within the CLP monomer sequence. In contrast to the hydrophobic GPP collagen-like flanking sequences, this block of 21 highly charged hydrophilic amino acids should form a destabilized flexible helical region accessible for interaction with cells. Promotion of epithelialization of the surface of an implanted device will improve the compatibility and rejection characteristics increasing its lifetime and safety. The subject compositions may find use as wound dressings, allowing for neovascularization, eye applications, matrices for artificial organs and the like.

Construction of CLP monomer.

The CLP (Collagen-Like Protein) synthetic gene was assembled from smaller parts. First, three double-stranded sections of DNA ranging from 40 to 60 bp in length were chemically synthesized.

```
        EcoRI   BanI
A 1)
AATTCGGTGCCCCTGGTCCGCCTGGTC-
CGCCTGGTCCACCGGGTCCTCCGG
   2)
      GCCACGGGGACCAGGCGGACCAGGCG-
GACCAGGTGGCCCAGGAGGCC

BanII (Asp718)
GGGCTC                                              (SEQ ID NO:51)
CCCGAGCATG                                          (SEQ ID NO:52)

BanII                             SmaI
B 3)      CCGGGTCCTCCAGGACCGCCAGGTCCGCCTGGTCCCCC    (SEQ ID NO:53)
  4) CCGAGGCCCAGGAGGTCCTGGCGGTCCAGGCGGACCAGGGGG     (SEQ ID NO:54)

SmaI                     BanI   ↓
C 5) GGGTCCTGCAGGTCCAGTAGGTAGCCCCGGTGCC
  6) CCCAGGACGTCCAGGTCATCCATCGGGGCCACGG

FspI      EcoRV SalI
ATGTGTGCGCATCGATC                                   (SEQ ID NO:55)
TACACACGCGTAGCTATAGAGCT                             (SEQ ID NO:56)
```

Sections A and C (the sequence of section C after the arrow is not coding for CLP but is a modification of the multiple cloning site of the acceptor plasmid) were cloned separately into plasmid pUC19 that had been digested with the appropriate REN. The DNA sequence was verified and two plasmids were selected, pPTO111 and pPT0112, carrying the correct sequence. Section B was ligated into pPTO111 that had been digested with BanII and SraI RENs. Plasmid pPT0113 was sequenced and found correct.

Plasmids pPT0112 and pPT0113 were digested with the appropriate RENs to release section C and Sections A+B respectively. After purification these DNA fragments were ligated into pSY937 previously digested with BanI and EcoRV RENs. The product of the ligation reaction was transformed into *E. coli* strain HB101. Plasmid DNA from transformants was purified and digested with BanI; clones containing inserts of the correct size were sequenced. Plasmid pPT0116 contained the desired sequence shown for section A+B+C (see Table 7). This plasmid was digested with BanI REN, and the digestion mixture was diluted and ligated with T4 DNA Ligase. *E. coli* HB 101 competent cells were transformed and screened for loss of the CLP insert; one plasmid, pPT 0125, was selected to be used as acceptor vector for subsequent constructions.

TABLE 7

```
      G  A  P  G  P  P  G  P  P  G  P  P  G  P  P  G  A
5"-GGTGCCCCTGGTCCGCCTGGTCCGCCTGGTCCACCGGGTCCTCCGGGGCT
3"-CCACGGGGACCAGGCGGACCAGGCGGACCAGGTGGCCCAGGAGGCCCCGCA
   |_____A_____|

P  G  P  P  G  P  P  G  P  P  G  P  P  G  P  A  G  P
CCGGGTCCTCCAGGACCGCCAGGTCCGCCTGGTCCCCCGGGTCCTGCAGGTCCA
GGCCCAGGAGGTCCTGGCGGTCCAGGCGGACCAGGGGGCCCAGGACGTCCAGGT
____|  |_____B_____| |____G_____

V  G  S  P  G  A                                    (SEQ ID NO:57)
GTAGGTAGCCCCGGTGCC-3"                               (SEQ ID NO:58)
CATCCATCGGGGCCACGG-5"
____C_____|
```

Construction of CLP-CB monomer.

Two oligonucleotide strands were synthesized as described in Example 1.

```
       AvaI                PvuI
i)  CCGGGACTGCCAGGCCCGAAAGGCGATCGTGGCGACGCCGGTCCTAAAGGC
ii)     GGCCCTGACGGTCCGGGCTTTCCGCTAGCACCGCTGCGGCCAGGATTTCCG

AvaI
GCAGATGGCAGC                                              (SEQ ID NO:59)
CGTCTACCGTCGGGCC                                          (SEQ ID NO: 60)
```

The two oligonucleotide strands were annealed and ligated with the DNA of plasmid pPTO116 (CLP monomer in pSY937) which had been digested with AvaI REN.

The products of this ligation reaction were transformed into E. coli strain HB101. Plasmid DNA from transformants was purified and digested with BanI; clones containing inserts of the correct size were digested with PstI and BqlI RENs for the determination of orientation. Plasmid DNA from correct clones was sequenced. Plasmid pPTO117 (shown in Table 8) contained the desired CLP-CB monomer sequence, oligonucleotides (i) and (ii) are shown below in bold and underlined.

ligation reaction was transformed into E. coli strain HB101. Transformants were selected for resistance to kanamycin. Plasmid DNA from individual transformants was purified and analyzed for increased size due to CLP multiple DNA insertion. Several clones were obtained ranging in size from 0.5 kbp to 0.9 kbp. One clone pPTO190, with an insert of approximately 3.5 kbp was chosen for expression and protein analysis.

CLP-CB

Plasmid DNA from pPTO117 was digested with BanI REN and the digestion fragments were separated by agarose gel electrophoresis. The CLP-CB gene fragment, 180 bp, was excised and purified by NACS column (see Example 1). The purified fragment was ligated with plasmid pSY1262 which had been digested with REN BanI. The product of this

TABLE 8

```
  G   A   P   G   P   P   G   P   P   G   P   P   G   P   P   G   A
5'-GGTGCCCCTGGTCCGCCTGGTCCGCCTGGTCCACCGGGTCCTCCGGGGCT
3'-CCACGGGGACCAGGCGGACCAGGCGGACCAGGTGGCCCAGGAGGCCCCGCA

P   G   P   P   G   P   P   G   P   P   G   P   P   G   L   P   G   P
CCGGGTCCTCCAGGACCGCCAGGTCCGCCTGGTCCCCCGGGACTGCCAGGCCCG
GGCCCAGGAGGTCCTGGCGGTCCAGGCGGACCAGGGGGGCCTGACGGTCCGGGC

K   G   D   R   G   D   A   G   P   R   G   A   D   G   S   P
AAAGGCGATCGTGGCGACGCCGGTCCTAAAGGCGCAGATGGCAGCCCG
TTTCCGCTAGCACCGCTGCGGCCAGGATTTCCGCGTCTACCGTCGGGC

G   P   A   G   P   V   G   S   P   G   A
GGTCCTGCAGGTCCAGTAGGTAGCCCCGGTGCC-3'                      (SEQ ID NO:61)
CCAGGACGTCCAGGTCATCCATCGGGGCCACGG-5'                      (SEQ ID NO:62)
```

CLP and CLP-CB Polymer Construction.

CLP

Plasmid DNA from pPTO116 was digested with BanI REN and the digestion fragments were separated by agarose gel electrophoresis. The CLP gene fragment, 117 bp, was excised and purified by NACS column (see Example 1). The purified fragment was ligated with plasmid pSY1262 which had been digested with REN BanI. The product of this ligation reaction was transformed into E. coli strain HB101. Transformants were selected for resistance to kanamycin. Plasmid DNA from individual transformants was purified and analyzed for increased size due to CLP-CB multiple DNA insertion. Several clones were obtained ranging in size from 0.5 kbp to 3.5 kbp. One clone pPTO129, with an insert of approximately 1.1 kbp was chosen for expression and protein analysis.

TABLE 6

```
   G   A   G   S   G   A   G   A   G   S   G   A   G   A   G   S   G
5'-GGTGCCGGCAGCGGTGCAGGAGCCGGTTCTGGAGCTGGCGCGGGCTCTGGC
3'-CCACGGCCGTCGCCACGTCCTCGGCCAAGACCTCGACCGCGCCCGAGACCG

A   G   A   G   S   G   A   G   A   G   S   G   A   G   A   G   S   G
GCGGGCGCAGGATCCGGCGCAGGCGCTGGTTCTGGCGCAGGGGCAGGCTCTGGC
CGCCCGCGTCCTAGGCCGCGTCCGCGACCAAGACCGCGTCCCCGTCCGAGACCG

A   G   A   G   S   G   A   A   L   C   V   S   E   P   G   Y   I   G
GCAGGAGCGGGGTCTGGAGCTGCACTGTGTGTTAGCGAACCCGGGTATATCGGT
CGTCCTCGCCCCAGACCTCGACGTGACACACAATCGCTTGGGCCCATATAGCCA

S   R   C   D   A   G   Y   G   A   G   A   G   S   G   A   G   A   G
AGCCGTTGCGATGCAGGCTATGGAGCTGGCGCTGGCTCAGGTGCTGGAGCAGGA
```

TABLE 6-continued

| | |
|---|---|
| TCGGCAACGCTACGTCCGATACCTCGACCGCGACCGAGTCCACGACCTCGTCCT | |
| S G A | (SEQ ID NO:63) |
| AGCGGAGCG-3' | (SEQ ID NO:64) |
| TCGCCTCGC-5' | |

Plasmid DNA from pPTO121 was digested with BanI REN and the digestion fragments were separated by agarose gel electrophoresis. The SLP-L2 gene fragment, 222 bp, was excised and purified by NACS column (see Example 1). The purified fragment was ligated with plasmid pSY1262 which had been digested with REN BanI. the product of this ligation reaction was transformed into *E. coli* strain HB101. Transformants were selected for resistance to kanamycin. Plasmid DNA from individual transformants was purified and analyzed for increase in size due to SLP-L2 multiple DNA insertion. Several clones were obtained ranging in size from 1 kbp to 4 kbp. One clone pPTO150, with an insert of approximately 2.0 kbp was chosen for expression and protein analysis.

CLP and CLP-CB Expression

An overnight culture which had been grown at 30° C. was used to inoculate 50 ml of LB media contained in a 250 ml flask. Kanamycin was added at a final concentration of 50 μg per ml and the culture was incubated with agitation (200 rpm) at 30° C. When the culture reached an $OD_{600}$ of 0.8, 40 ml were transferred to a new flask prewarmed at 42° C. and incubated at the same temperature for approximately 2 hours. The cultures (30° C. and 42° C.) were chilled on ice and $OD_{600}$ was taken. Cells were collected by centrifugation divided in 1.0 $OD_{600}$ aliquot and used to perform dot blot and western analysis using CLP antisera (see Example 1). For purification and amino acid analysis larger cultures were used.

Analysis

*E. coli* strain HB101 containing plasmid pPTO190 or pPT 0129 were grown as described above. The proteins produced by these cells were analyzed by SDS-PAGE for detection of reactivity to CLP antibodies (see Example 1). In both analyses a strong reactive band was observed of an apparent molecular weight of 45 kD and 60 kD respectively.

```
pPT0190        CLP  Protein   331 AA    MW 29,000
MDPVVLQRRDWENPGVTQLNRLAAHPPFASDPM
{[GAP (GPP)4]2GPAGPVGSP}9
GAMCAHRYQLSAGRYHYQLVWCQK                        (SEQ ID NO:65)

pPT0129   CLP-CB    Protein   358 AA    MW 32,000
MDPVVLQRRDWENPGVTQLNRLAAHPPFASDPM
{[GAP (GPP)4]2 (GLPGPKGDRGDAGPKGADGSP)GPAGPVGSP}5
GAMCAHRYQLSAGRYHYQLVWCQK                        (SEQ ID NO:66)
```

Construction of KLP 1.2 monomer

The keratin-like polymer, KLP-1.2, was modified to include the 15 amino acid sequence GRGGS-FGGSSYGGGS (SEQ ID NO:67) (termed interactionsequence, IS) and designated KLP-1.3. Segments similar to this sequence occur at the amino and carboxyl terminal ends of the 59,000 molecular weight subunit of mouse epidermalkeratin (Steinert et. al., *Nature* 302, 794–800, 1983). They comprise terminal non-helical structures whose function is unknown. However, proteolytic digestion products of filamentous keratin lacking these terminal sequences also lack the ability to reform fiber structures. We propose that the IS sequence is a non-helical, possibly beta conformation, forming structure which interacts with adjacent helical segments to organize them into fibers. Depending on its dispersity and length, the IS sequence within KLP promotes the association of KLP helices into complex matrices or organizes the helical chains into globular macromolecular particles. The IS sequence can also be active in associating with existing keratin fibers and can also promote the specific non-covalent binding of KLP and other polymer compositions to the skin, hair, nails, etc.

Keratin-like proteins are designed to provide a matrix which can be converted to a hardened protein by cross-linking. The repeating 7—7 motif produces alpha-helices, with 4 turns of the helix, each turn stabilized by intramolecular hydrogen bonds. The placement of the charged amino acids produces charge complementarity between helices lying next to one another. Adjacent helices form coiled bundles of helices, which in turn aggregate into aligned fibers and meshed networks. The contact points can be chemically linked, if desired. Depending on the amount of cross-linkable amino acids, cysteines or acid/basic amino acids, e.g., D,E/K,R, various degrees of hardening can be obtained. At less than 3% by weight cysteine content, the polymer is soft and pliable, while with greater than 3%, the protein hardens as in scale and horn. Instead of cystine cross-links, amide cross-links can be obtained, using carbodiimides, for example.

The KLP (Keratin Like Protein) synthetic gene was assembled from smaller parts. First, four double-stranded sections of DNA ranging from 46 to 62 bp in length were chemically synthesized as described in Example 1.

```
              AvaI
  Ban I       XhoI                                  NsiI
        FokI      EcQ47III              HD III          SPHI
S A 1  GTGCCGGATGCTCGAGCGCTAAACTGAAATTGGCAGAAGCGAAGCTTATGCATG    (SEQ ID NO:68)
    2      GCCTACGAGCTCGCGATTTGACTTTAACCGTCTTCGCTTCGAATAC        (SEQ ID NO:69)

DdeI
     HdIII                         EspI    SacI   NsiI
S B 1  AGCTTGAGCTGGCAGAAGCTAAACTGAAGCTGGCGGAAGCTAAGCGAGCTCATGCA  (SEQ ID NO:70)
    2      ACTCGACCGTCTTCGATTTGACTTCGACCGCCTTCGATTCGCTCGAGT      (SEQ ID NO:71)

EspI                                             SacI
S C 1  AATTGCTAAGCTGGAGCTGGCAGAAGCTAAACTGAAGTTAGCGGAAGCTAAACTGGAGCT  (SEQ ID NO:72)
    2      CGATTCGACCTCGACCGTCTTCGATTTGACTTCAATCGCCTTCGATTTGACC      (SEQ ID NO:73)

SphI
     SacI                                   EaeI        NciI
S D 1   CGCGGAAGCCAAACTGAAGCTGGCGGAGGCTAAATTGGAACTGGCCGAGGCTAAAATGCATG  (SEQ ID NO:74)
    2   TCGAGCGCCTTCGGTTTGACTTCGACCGCCTCCGATTTAACCTTGACCGGCTCCGATTTTAC  (SEQ ID NO:75)
```

The assembly of the KLP 1.2 monomer required several steps. Sections A and B were cloned separately from sections C and D and then the monomer was assembled from the two separate clones.

3 repeats of the 14 amino acid motif (Bert: this was as Franco wrote it, you may want to replace with 6 repeats of the 7 amino acid motif). This plasmid was chosen for subsequent polymer constructions (See table 9).

TABLE 9

```
GCTAAACTGAAATTGGCAGAAGCGAAGCTTGAGCTGGCAGAAGCT
CGATTTGACTTTAACCGTCTTCGCTTCGAACTCGACCGTCGTTCGA
 A  K  L  K  L  A  E  A  K  L  E  L  A  E   A
                        1

AAACTGAAGTTAGCGGAAGCTAAACTGGAGCTCGCGGAAGCCAAACTGAAGCTGGCGGAGGCT
TTTGACTTCAATCGCCTTCGATTTGACCTCGAGCGCCTTCGGTTTGACTTCGACCGCCTCCGA    (SEQ ID NO:76)
 K  L  K  L  A  E  A  K  L  E  L  A  E  A  K  L  K  L  A  E  A
                2                                            3

AAATTGGAACTGGCCGAGGCTAAA
TTTAACCTTGACCGGCTCCGATTT                                            (SEQ ID NO:77)
 K  L  E  L  A  E (A  K)
```

Section D was cloned in plasmid pUC19 previously digested to completion with REN SacI and SphI. Five clones were selected to be sequenced. Plasmid pPTO119 was found to be correct and was chosen for the cloning of section C after it had been digested with the appropriate RENs. The DNA sequence was verified and one plasmid was selected, pPTO167, carrying the correct sequence of section C+D.

Plasmid pSY1568 was digested with BanI and SphI RENs and ligated with section A of KLP. Plasmid pPT0127 was found to be correct after DNA sequencing and was used for subsequent cloning of Section B. Plasmid pPT0127 digested with HindIII and NsiI RENs was ligated with section B synthesized DNA. The DNA sequence was verified and one plasmid was selected, pPT0128, carrying the correct sequence. Plasmid pPTO167 was digested with REN DdeI and the DNA band carrying the part of the vector and KLP section C+D was agarose purified. The purified DNA was digested to completion with REN NsiI and the agarose slice corresponding to the section C+D was ligated into plasmid pPT0128 previously digested with CelII and NsiI RENs. The product of the ligation reaction was transformed into *E. coli* strain HB101. Plasmid DNA from transformants was purified and digested with FokI; clones containing an insert of the correct size were sequenced. "XcmI REN; positive clones were sequenced for KLP 1.2 monomer. One clone, plasmid pPTO188, contained a KLP DNA sequence of only KLP 1.2 Polymer Construction Plasmid DNA from pPTO188 was digested with FokI REN and the digestion fragments were separated by agarose gel electrophoresis. The KLP 1.2 gene fragment, 126 bp, was excised and purified by NACS column (see Example 1). Plasmid pPTO188 backbone was also purified and ligated to itself. This ligatin product was used to transform competent cells of *E. coli* strain HB101. Plasmid DNA from individual transformants was analyzed for loss of the KLP gene fragment. One plasmid, pPTO189, was selected to be used as an acceptor for the multimerization of the KLP gene monomer. Plasmid pPTO189 was digested with FokI REN and subsequently treated with phosphatase (see Example 1). After agarose purification by NACS column (see Example 1) the plasmid was ligated with approximately 0.5 mg of KLP gene monomer DNA. The ligation mixture was used to transform competent cells of *E. coli* strain HB101. Several clones were obtained ranging in size from 0.25 kbp to 2.0 kbp. One clone, pPTO191, with an insert of approximately 2.0 kbp was chosen for further constructions. Plasmid pPTO191 was digested with BanI, PvuII and StuI RENS; StuI digestion was necessary because the KLP insert was co-migrating on the gel with the plasmid backbone. The KLP gene multimer was purified by NACS column (see Example 1). The purified fragment was ligated with plasmid pSY1262 which had been digested with RENs BanI and EcoRV.

The product of this ligation reaction was transformed into *E. coli* strain HB101. Transformants were selected for resistance to kanamycin. Plasmid DNA from individual transformants was purified and analyzed for increased size due to KLP multiple DNA insertion. Several clones were obtained ranging in size from 1 kbp to 4 kbp. One clone pPTOYYY, with an insert of approximately 3.0 kbp was chosen for expression and protein analysis.

Analysis

E. coli strain HB101 containing plasmid pPTO192 or PT0193 were grown at 30° C. to an $OD_{600}$ of 0.7 and then shifted to 42° C. for 2.0 hours. The proteins produced by these cells were analyzed by SDS-PAGE for detection of $^{14}C$ labeled protein. A strong reactive band was observed with an apparent molecular weight of approximately 62 kD and 80 kD, respectively.

KLP 1.3 Polymer Construction

Plasmid DNA containing the KLP 1.3 monomer sequence is digested with FokI REN and the digestion fragments are separated by agarose gel electrophoresis. The KLP 1.3 gene fragment, 171 bp, is excised and purified by NACS column (see Example 1). The purified fragment is ligated with plasmid pSY1262 which is digested with REN BanI. The product of this ligation reaction is transformed into E. coli strain HB101. Transformants are selected for resistance to kanamycin. Plasmid DNA from individual transformants is purified and analyzed for increase in size due to KLP 1.3 multiple DNA insertion. Several clones obtained and chosen for expression and protein analysis.

Analysis

E. coli strain HB101 containing plasmid pPTOTBD is grown at 30° C. to an $OD_{600}$ of 0.7 and then shifted to 420C,

```
pPTO192      KLP Protein      572AA      MW 61,800      (SEQ ID NO:78)
    MDPVVLQRRDWENPGVTQLNRLAAHPPFASDPMGAGCSS
    [(AKLKLAEAKLELAE)3]12
    AKMHAHPPGSISDQLSAGRYHYQLVWCQK pPTO193      KLP Protein      740AA      MW 79,900      (SEQ ID NO:79)
    MDPVVLQRRDWENPGVTQLNRLAAHPPFASDPMGAGCSS
    [(AKLKLAEAKLELAE)3]16
    AKMHAHPPGSISDQLSAGRYHYQLVWCQK
```

KLP 1.3

Construction of KLP1.3 Polymer:

Two oligonucleotide strands were synthesized and purified as described in Example 1.

after the addition of 40 µCi per ml of $^{14}C$-Leucine or Alanine, for 2.0 hours. The proteins produced by these cells are analyzed by SDS-PAGE for detection of $^{14}C$ labeled protein. A strong reactive band is observed.

```
5 A  GGCCGAGGGCCGTGGTGGCAGCTTCGGTGGATCCTCTTATGGTGGCGGTTCTGCTAAAATGCA    (SEQ ID NO:80)

B       CTCCCGGCACCACCGTCGAAGCCACCTAGGAGAATACCACCGCCAAGACGATTTT         (SEQ ID NO:81)
```

The two oligonucleotide strands were annealed and ligated with the DNA of plasmid pPTO188 which had been digested with EaeI and NsiI RENs.

The products of this ligation reaction are transformed into E. coli strain HB101. Plasmid DNA from transformants are purified and digested with FokI: clones containing inserts of the correct size are digested with the appropriate RENs and plasmid DNA from correct clones are sequenced. One plasmid (shown in Table 10) contains the desired KLP 1.3 monomer sequence, oligonucleotides (5A) and (5B) are shown below in bold and underlined.

KLP 1.3 Protein MDPVVLQRRDWENPGVTQLNR-LAAHPPFASDPMGAGCSS (AKLKLAEAKLELAE)$_3$ GRGGSFGGSSYGGGS]$_n$ AKMHAHPPGSISDQL-SAGRYHYQLVWCQK (SEQ ID NO:84)

Following the procedures described above, other polymers are prepared. These polymers influence cellular function by containing ligand sequences which interact with cell surface receptors. These polymers are prepared by inserting oligonucleotides encoding the nerve cell attachment promoting sequence from human laminin B1, YIGSR (SEQ ID NO:85), into the protein polymer sequence of ELP I at the

TABLE 10

```
GCTAAACTGAAATTGGCAGAAGCG
CGATTTGACTTTAACCGTCTTCGC
 A  K  L  K  L  A  E  A

AAGCTGGAGCTGGCAGAAGCTAAACTGAAGTTAGCGGAAGCTAAACTGGAGCTC
TTCGACCTCGACCGTCTTCGATTTGACTTCAATCGCCTTCGATTTGACCTCGAG
 K  L  E  L  A  E  A  K  L  K  L  A  E  A  K  L  E  L

GCGGAAGCCAAACTGAAGCTGGCGGAGGCTAAATTGGAACTGGCCGAG   GGCCGTGGTGGCAGCTTC
CGCCTTCGGTTTGACTTCGACCGCCTCCGATTTAACCTTGACCGGCTC   CCGGCACCACCGTCGAAG
 A  E  A  K  L  K  L  A  E  A  K  L  E  L  A  E     G  R  G  G  S  F

GGTGGATCCTCTTATGGTGGCGGTTCT    GCTAAA                                 (SEQ ID NO:82)
CCACCTAGGAGAATACCACCGCCAAGA    CGATTT                                 (SEQ ID NO:83)
 G  G  S  S  Y  G  G  G  S      A  K
```

SmaI site. Additionally, a polymer is prepared by inserting oligonucleotides encoding the T cell receptor binding sequences from human MHC class I HLA-A2, PEYDGETRKVKAHSQTHRVDTLRY (SEQ ID NO:86) (residues 57–84) and TRKWAAHVEQLRAYEGTVEWRY (SEQ ID NO:87) (residues 143–171), into the SLPIII polymer in alternating fashion at the gene location containing the PstI site.

These polymers exhibit activities of chemical reactivity and cross-linking with themselves or with other polymers or materials. These polymers are prepared by inserting oligonucleotides encoding the sequences DPGK (SEQ ID NO:88), NPGC (SEQ ID NO.89), or RPGE (SEQ ID NO:90) into the PstI site of the synthetic polymer gene, SLPIII. Other examples of chemically reactive polymers are prepared by inserting oligonucleotides encoding the sequences GAGD (SEQ ID NO:91), GAGC (SEQ ID NO:92), or GAGK (SEQ ID NO:93) into the BanII site of the synthetic polymer gene, SLPIV, or by inserting oligonucleotides encoding the sequences GEGVP (SEQ ID NO:94), GCGVP (SEQ ID NO:95), or GKGVP (SEQ ID NO:96) into the Smal site of the synthetic polymer gene ELP I. The synthetic polymers SLPIV and ELP I are described in the previously cited PCT application.

Additional compositions are prepared according to the above procedures. These compositions include:

| | | |
|---|---|---|
| HOMOPOLYMERS | | |
| SLP 5 | $[(GAGAGQ)_6]_n$ | (SEQ ID NO:97) |
| SLP 6 | $[(GAGAGS)_9GAAGYGAGY]_n$ | (SEQ ID NO:98) |
| FUNCTIONAL POLYMERS | | |
| SLP-V1 | $[(GAGAGC)_9$ $^G$AAARPSLTKRQRFRHRNRKGYRSORGHSR GRNQNSRRPSAAGY$]_n$ | (SEQ ID NO:99) |
| SLP-V2 | (GAGAGS)9GAAARPSLTKXQRFRHRNRKGYRSQRGHSR RPSAGY$]_n$ | (SEQ ID NO:100) |
| SLP-F-L1 | $[(GAGAGS)_9$GM VTGRGDSPASAAVCEPGYIGSRCDAGY$]_n$ | (SEQ ID NO:101) |
| SLP-F-L2 | $[(GAGAGS)_9$GAAVTGRGDSPASAALCVSEPGYIGSRCDAGY$]_n$ | (SEQ ID NO:102) |
| SELP2-SLPF | $[(GAGAGS)_5(GVGVP)_8(GAGAGS)_6$GAAVTGRGDSPAS AAGY$]_n$ | (SEQ ID NO:103) |
| SELP3-SLPF | $[(GAGAGS)_8(GVGVP)_8(GAGAGS)_9$GAAVTGRGDSPAS AAGY$]_n$ | (SEQ ID NO:104) |
| SLPC-SLPF | $[(GAGAGS)_9$GAAGAGCGDPGKGCCVAGAGY$(GAGAGS)_9$GAA VTGRGDSPASAAGY$]_n$ | (SEQ ID NO:105) |
| FUNCTIONAL POLYMERS (CLP) | | |
| CLP-F | $\{[GAP(GPP)_4]_2$GPA(VTGRGDSPASAA)GPVGSP$\}_n$ | (SEQ ID NO:106) |
| CLP-L1 | $\{[GAP(GPP_4)]_2$GPA(VCEPGYIGSRCDA)GPVGSP$\}_n$ | (SEQ ID NO:107) |
| CLP-L2 | $\{[GAP(GPP)_4]_2$GPA(LCVSEPGYIGSRCDA)GPVGSP$\}_n$ | (SEQ ID NO:108) |
| CLP-V1 | $\{[GAP(GPP)_4]_2$ GPAARPSLTKKQRFRHRNRKGYRSQRGHSRGRNQNSRRPSGP VGSP$\}_n$ | (SEQ ID NO:109) |
| CLP-V2 | $\{[GAP(GPP)^4]_2$ GPAARPSLTKKQRFRHRNRKGYRSQRGHSRG RNQNSRRPSGPVGSP$\}_n$ | (SEQ ID NO:110) |
| CLP/CB-F | $\{[GAP(GPP)_4]_2$(GLPGPKGDRGDAGPKGADGSPGPA)(VTG RGDSPASAA)GPVGSP}n | (SEQ ID NO:111) |
| CLP/CB-L1 | $\{[GAP(GPP)_4]_2$(GLPGPKGDRGDAGPKGDGSPGPA) (VCEPGYIGSRCDA)GPVGSP}n | (SEQ ID NO:112) |
| CLP/CB-L2 | $\{[GAP(GPP)_4]_2$(GLPGPKGDRGDAGPKGADGSPGPA) (LCVSEPGYIGSRCDA)GPVGSP$\}_n$ | (SEQ ID NO:113) |
| CLP/CB-F-L1 | $\{[GAP(GPP)_4]_2$(GLPGPKGDRGDAGPKGADGSPGPA) (VTGRGDSPASAA)(VCEPGYIGSRCDA)GPVGSP$\}_n$ | (SEQ ID NO:114) |
| CLP/CB-F-L2 | $\{[GAP(GPP)_4]_2$(GLPGPKGDRGDAGPKGADGSPGPA) (VTGRGDSPASAA)(LCVSEPGYIGSRCDA)GPVGSP$\}_n$ | (SEQ ID NO:115) |

```
FUNCTIONAL POLYMERS (ADHESIVE)                              -continued

ALP 1      [(YKAKPSYPPT)₃]ₙ                                 (SEQ ID NO:116)

SLP-ALP    [(GAGAGS)₉GAAV(TYKAKPSYPP)₃ₘTAGY]ₙ  m ≧ 1        (SEQ ID NO:117)

CLP-ALP    {[GAP(GPP)₄]₂(TYKAKPSYPP)₃ₘGPACPVGSP}ₙ  m ≧ 1    (SEQ ID NO:118)
```

It is evident from the above results that a powerful capability is provided for producing polymers having good structural properties, as well as novel capabilities, where specific amino-acid sequences may be made readily available to the environment, while providing for structural or non-structural capabilities such as fiber, film, and membrane formation, emulsions, coatings, etc. Thus the polymer is comprised of strands which interact to provide for structural characteristics, such as article formation with good mechanical, e.g., tensile properties, while at the same time providing for amino acid sequences which may be used in a wide variety of biological and chemical applications. The subject compositions may be used for binding a wide variety of specific binding materials, as catalytic substances, where the amino acid sequence may specifically chelate a wide variety of elements, as purification media, as composites, laminates, adhesives, combined with inorganic or organic materials, such as carbon fibers, nylon fibers, nitrocellulose, etc., as flask coatings for the growth of cells, as affinity columns, supports for biological materials, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A recombinantly produced proteinaceous polymer composition comprising a proteinaceous polymer of at least about 15 kDal that comprises strands of repeating units of a natural protein capable of assembling into aligned structures to be formable into articles, wherein at least one of said strands comprises a tandem repeat of said repeating units, with at least two strands joined by an intervening oligopeptide other than said repeating units and wherein said composition is substantially homogeneous.

2. A recombinantly produced polymer composition according to claim 1, wherein said repeating units are from about 3 to 30 amino acids, said strands are from about 25 to 150 amino acids, and said intervening oligopeptide is between each of said strands and is from about 4 to 50 amino acids.

3. A recombinantly produced polymer composition according to claim 1, wherein said repeating unit is a repeating unit of fibroin, elastin, keratin, or collagen or combinations of said repeating units.

4. A recombinantly produced polymer composition according to claim 1, wherein said intervening oligopeptide comprises the amino acid sequence RGD, DP, EP, DPGKGXY (SEQ ID NO:12), wherein at least one of X and Y is C, EPGYIGSRCDAGY (SEQ ID NO:13), PKGDRGDAGPK (SEQ ID NO:14), or AVTGRGDSPAS (SEQ ID NO:15), where conservative substitutions may be made at other than the functional site.

5. A recombinantly produced polymer composition according to claim 1, wherein said polymer is a block copolymer comprising two different repeating units.

6. A recombinantly produced proteinaceous polymer composition comprising a proteinaceous polymer of at least about 15 kDal which comprises strands of repeating units having the sequence GAGAGS (SEQ ID NO: 119), VPGVG (SEQ ID NO:2), or at least one of GPP and GAP and capable of assembling into aligned structures to be formable into articles, wherein at least one of said strands comprises a tandem repeat of said repeating units, with at least two strands joined by an intervening oligopeptide other than said repeating units and wherein said composition is substantially homogeneous.

7. A recombinantly produced proteinaceous polymer composition according to claim 1, wherein said polymer is from about 30 kDal to about 250 kDal.

8. A recombinantly produced proteinaceous polymer composition according to claim 6, wherein said polymer is from about 30 kDal to about 250 kDal.

9. A recombinantly produced proteinaceous polymer composition according to claim 1, wherein each of said strands comprises a tandem repeat of said repeating units.

10. A recombinantly produced proteinaceous polymer composition according to claim 1, wherein said intervening sequence is characterized by a biological or chemical function.

11. A recombinantly produced proteinaceous polymer composition according to claim 1, wherein said intervening sequence has at least one chemically active amino acid or a naturally occurring sequence having binding specificity for a protein receptor.

12. A recombinantly produced proteinaceous polymer composition according to claim 6, wherein each of said strands comprises a tandem repeat of said repeating units.

13. A recombinantly produced proteinaceous polymer composition according to claim 6, wherein said intervening sequence is characterized by a biological or chemical function.

14. A recombinantly produced proteinaceous polymer composition according to claim 6, wherein said intervening sequence has at least one chemically active amino acid or a naturally occurring sequence having binding specificity for a protein receptor.

* * * * *

UNITED STATES PATENT AND TRADEMARK OFFICE
CERTIFICATE OF CORRECTION

PATENT NO. : 6,184,348 B1
DATED : February 6, 2001
INVENTOR(S) : Franco A. Ferrari and Joseph Cappello It is certified that error appears in the above-identified patent and that said Letters Patent is hereby corrected as shown below:

<u>Title page,</u>
Item [60], Related U.S. Application Data, "07/114,618, filed on Oct. 29, 1997" should read -- 07/114,618, filed on Oct. 29, 1987 --
Item [56], References Cited, OTHER PUBLICATIONS, "Sandberg et al." "Elastin Structure, Biosynthesis and Relation to Disease Sates" should read -- Elastin Structure, Biosynthesis and Relation to Disease States --

<u>Column 1,</u>
Line 32, "in vitro." should read -- in vitro --

<u>Coumn 5,</u>
Line 4, "$[A^2)_n2(B^2)_p23q^2$" should read -- $[A^2)_n2(B^2)_p2]_q2$" --
Line 55, "$K_k'[(D)_n(E)_{pq}L_1$'" should read -- $K_k'[(D)_n(E)_p]_qL_1'$ --

<u>Column 7,</u>
Line 14, "same of different" should read -- same or different --

<u>Column 8,</u>
Line 16, "mote" should read -- more --

<u>Column 14,</u>
Line 4, "($^{32}$P]" should read -- [$^{32}$P] --
Line 56, "MM" should read -- mM --

<u>Column 15,</u>
Line 48, "and (SEQ ID NO:21) the sequence" should read -- and the sequence --
Line 49, "(GAP[GPP]$_4$)$_2$ (the repeat" should read -- (GAP[GPP]$_4$)$_2$ (SEQ ID NO:21) (the repeat --

<u>Column 24,</u>
Line 62, "1987, a PCT/US/87/02822)" should read -- 1987, PCT/US/87/02822) --

<u>Column 26,</u>
Line 41, "PSY1521" should read -- pSY1521 --

<u>Column 27,</u>
Line 16, "(pH-7.5)" should read -- (pH 7.5) --

UNITED STATES PATENT AND TRADEMARK OFFICE
CERTIFICATE OF CORRECTION

PATENT NO. : 6,184,348 B1
DATED : February 6, 2001
INVENTOR(S) : Franco A. Ferrari and Joseph Cappello It is certified that error appears in the above-identified patent and that said Letters Patent is hereby corrected as shown below:

Columns 29-30,
Line 62, SEQ ID NO:41, "PPT0105" should read -- pPT0105
-- Line 67, "GAAGAGCGDPGKGCCVAGAGY (GAGAGS) 2GAGAMDPGRYQLSAGRYHYQLVWCQK"

should read -- GAAGAGCGDPGKGCCVAGAGY (GAGAGS) $_2$GAGAMDPGRYQLSAGRYHYQLVWCQK --

Column 30,
Line 12, "(blank)" should read -- Expression --
Line 13, "Expression An overnight" should read -- An overnight --
Line 17, "300C." should read -- 30°C. --

Column 31,
Table 5, Line 7 "CGCCCGCGTCCTAGGCCGCGTCCGCGACCAAGACCGCGTCCCCG-CCGAGACCG"
should read -- CGCCCGCGTCCTAGGCCGCGTCCGCGACCAAGACC GCGTCCCCGTCCGAGACCG --

Column 32,
Line 15, "iii) 5'    CTGTGTGTTAGC -3'" should read -- iii) 5'    CTGTGTGTTAGCGAACCC -3' --

Column 33,
Line 2, "MDPVVLQRRDWENPGVTQLNRAA A HPPFASDPMGAGS (GAGAGS) $_6$" should read -- MDPVVLQRRDWENPGVTQLNRLAA HPPFASDPMGAGS (GAGAGS) $_6$ --
Line 4, "GAAVCEPGYIGSRCDAGY (GAGAGS) $_2$ GAGAMDPGRYQLSAGRYHYQLVWCQKA" should read -- GAAVCEPGYIGSRCDAGY (GAGAGS) $_2$ GAGAMDPGRYQLSAGRYHYQLVWCQK-
Line 7, "MDPVVLQRRDWENPGVTQLNRLL L HPPFASDPMGAGS (GAGAGS) $_6$" should read -- MDPVVLQRRDWENPGVTQLNRLAA HPPFASDP MGAGS (GAGAGS) $_6$ --
Line 9, "GAALCVSEPGYIGSRCDAGY (GAGAGS) $_2$ GAGAMDPGRYQLSAGRYHYQLVWCQKA" should read -- GAALCVSEPGYIGSRCDAGY (GAGAGS) $_2$ GAGAMDPGRYQLSAGRYHYQLVWCQK Column 35,
Line 29, "SraI" should read -- SmaI --

Columns 35-36,
Please remove Table 7
Please insert Corrected Table 7

```
           G  A  P  G  P  P  G  P  P  G  P  P  G  P  P  G  A
       5'- GGTGCCCCTGGTCCGCCTGGTCCGCCTGGTCCACCGGGTCCTCCGGGGCT
       3'- CCACGGGGACCAGGCGGACCAGGCGGACCAGGTGGCCCAGGAGGCCCCGCA
          |_____A_____|

P  G  P  P  G  P  P  G  P  P  G  P  A  G  P
       CCGGGTCCTCCAGGACCGCCAGGTCCGCCTGGTCCCCCGGGTCCTGCAGGTCCA
       GGCCCAGGAGGTCCTGGCGGTCCAGGCGGACCAGGGGGCCCAGGACGTCCAGGT
       |_____B_____|  |_____C_____|

V  G  S  P  G  A
       GTAGGTAGCCCCGGTGCC  -3'
       CATCCATCGGGGCCACGG  -5'
       |_____C_____|
```
--

Page 2 of 4

UNITED STATES PATENT AND TRADEMARK OFFICE
CERTIFICATE OF CORRECTION

PATENT NO.    : 6,184,348 B1
DATED         : February 6, 2001
INVENTOR(S)   : Franco A. Ferrari and Joseph Cappello It is certified that error appears in the above-identified patent and that said Letters Patent is hereby corrected as shown below:

<u>Columns 37-38,</u>
Lines 55-67, please move Table 6 to its correct location at Column 32, between lines 35 (underlined.) and 36 (Expression of SLP-Polymers.)

<u>Column 40,</u>
Line 10, "epidermalkeratin" should read -- epidermal keratin --

<u>Column 42,</u>
Line 19 please delete "(Bert: this was as"
Line 20 please delete "Franco wrote it, you may want to replace with 6 repeats of"
Line 21, please delete "the 7 amino acid motif)."

<u>Column 44,</u>
Line 16, "420C" should read -- 42°C --

Line 39, "LAAHPPFASDPMGAGCSS (AKLKLAEAKLELAE)$_3$" should read
--LAAHPPFASDPMGAGCSS [ (AKLKLAEAKLELAE)$_3$--

Line 46, "nerve celi" should read -- nerve cell --

<u>Columns 45-46,</u>
SEQ. ID NO: 99 line 1,    "[(GAGAGC)$_9$$^G$AAARPSLTKRQRFRHRNRKGYRSORGHSR"
should read   --[(GAGAGS)$_9$GAAARPSLTKRQRFRHRNRKGYRSQRGHSR--

SEQ. ID NO: 100 line 1,    "(GAGAGS)9GAAARPSLTKXQRFRHRNRKGYRSQRGHSR"
should read   --[(GAGAGS)$_9$GAAARPSLTKKQRFRHRNRKGYRSQRGHSR--

SEQ. ID NO: 111 line 2,   "RGDSPASAA) GPVGSP}n"  should read   --RGDSPASAA) GPVGSP}$_n$--

UNITED STATES PATENT AND TRADEMARK OFFICE
CERTIFICATE OF CORRECTION

PATENT NO. : 6,184,348 B1
DATED : February 6, 2001
INVENTOR(S) : Franco A. Ferrari and Joseph Cappello It is certified that error appears in the above-identified patent and that said Letters Patent is hereby corrected as shown below:

<u>Columns 45-46 cont'd,</u>
SEQ.ID NO: 112, line 2, "(VCEPGYIGSRCDA) GPVGSP}n" should read
-- (VCEPGYIGSRCDA) GPVGSP}$_n$ --

Signed and Sealed this

Ninth Day of September, 2003

JAMES E. ROGAN
*Director of the United States Patent and Trademark Office*

```
                              SEQUENCE LISTING (1) GENERAL INFORMATION:

(iii) NUMBER OF SEQUENCES: 119

(2) INFORMATION FOR SEQ ID NO:1:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:1:

Val Pro Gly Gly
1

(2) INFORMATION FOR SEQ ID NO:2:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:2:

Val Pro Gly Val Gly
1               5

(2) INFORMATION FOR SEQ ID NO:3:

(i) SEQUENCE CHARACTERISTICS:
         (A) LENGTH: 6 amino acids
         (B) TYPE: amino acid
         (C) STRANDEDNESS: single
         (D) TOPOLOGY: linear
```

(ii) MOLECULE TYPE: peptide (xi) SEQUENCE DESCRIPTION: SEQ ID NO:3:

Ala Pro Gly Val Gly Val
1               5

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ala Lys Leu Lys Leu Ala Glu
1               5

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ala Lys Leu Glu Leu Ala Glu
1               5

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Ala Lys Pro Pro Ser Thr Tyr Xaa Pro Pro Pro Ser Thr Tyr Xaa Lys
1               5                   10                  15

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Ser Gly Ala Gly Ala Gly
1               5

(2) INFORMATION FOR SEQ ID NO:8:

(i) SEQUENCE CHARACTERISTICS:
        (A) LENGTH: 59 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:8:

Gly Ala Gly Ala Gly Ser Gly Ala Gly Ala Gly Ser Gly Ala Gly Ala
 1               5                  10                  15

Gly Ser Gly Ala Gly Ala Gly Ser Gly Ala Gly Ala Gly Ser Gly Ala
             20                  25                  30

Gly Ala Gly Ser Gly Ala Gly Ala Gly Ser Gly Ala Gly Ala Gly Ser
         35                  40                  45

Gly Ala Gly Ala Gly Ser Gly Ala Ala Gly Tyr
         50                  55

(2) INFORMATION FOR SEQ ID NO:9:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Lys Leu Xaa Leu Ala Glu Ala
 1               5

(2) INFORMATION FOR SEQ ID NO:10:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

His Cys Cys His
 1

(2) INFORMATION FOR SEQ ID NO:11:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Cys His His Cys
 1

(2) INFORMATION FOR SEQ ID NO:12:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

```
Asp Pro Gly Lys Gly Xaa Tyr
1               5
```

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Glu Pro Gly Tyr Ile Gly Ser Arg Cys Asp Ala Gly Tyr
1               5                   10
```

(2) INFORMATION FOR SEQ ID NO:14:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Pro Lys Gly Asp Arg Gly Asp Ala Gly Pro Lys
1               5                   10
```

(2) INFORMATION FOR SEQ ID NO:15:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Ala Val Thr Gly Arg Gly Asp Ser Pro Ala Ser
1               5                   10
```

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Gly Arg Gly Gly Ser Phe Gly Gly Ser Ser Tyr Gly Gly Gly Ser
1               5                   10                  15
```

(2) INFORMATION FOR SEQ ID NO:17:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Gly Ala Gly Cys Gly Asp Pro Gly Lys Gly Cys Cys Val Ala
1               5                  10
```

(2) INFORMATION FOR SEQ ID NO:18:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Val Cys Asp Arg Gly Tyr Ile Gly Ser Arg Cys Asp
1               5                  10
```

(2) INFORMATION FOR SEQ ID NO:19:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Pro Lys Gly Asp Arg Ala Asp Ala Gly Pro Lys
1               5                  10
```

(2) INFORMATION FOR SEQ ID NO:20:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Tyr Thr Ile Thr Val Tyr Ala Val Thr Gly Arg Gly Asp Ser Pro Ala
1               5                  10                  15
Ser Ser Lys Pro Ile Ser Ile Asn Tyr Cys
                20                  25
```

(2) INFORMATION FOR SEQ ID NO:21:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Gly Ala Pro Gly Pro Pro Gly Pro Pro Gly Pro Pro Gly Pro Pro Gly
1               5                  10                  15
Ala Pro Gly Pro Pro Gly Pro Pro Gly Pro Pro Gly Pro Pro
                20                  25                  30
```

(2) INFORMATION FOR SEQ ID NO:22:

(i) SEQUENCE CHARACTERISTICS:
        (A) LENGTH: 61 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

GGTGCCGGCA GCGGTGCAGG AGCCGGTTCT GGAGCTGGCG CGGGCTCTGG CGCGGGCGCA    60

G    61

(2) INFORMATION FOR SEQ ID NO:23:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GATCCTGCGC CGCGCCAGA GCCCGCGCCA GCTCCAGAAC CGGCTCCTGC ACCGCTGCCG    60

GCACC    65

(2) INFORMATION FOR SEQ ID NO:24:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Gly Ala Gly Ser Gly Ala Gly Ala Gly Ser Gly Ala Gly Ala Gly Ser
1               5                   10                  15

Gly Ala Gly Ala Gly Ser
            20

(2) INFORMATION FOR SEQ ID NO:25:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

GATCCGGCGC AGGCGCTGGT TCTGGCGCAG GGCAGGCTC TGGCGCAGGA GCGGGGTCTG    60

GAGCTGCA    68

(2) INFORMATION FOR SEQ ID NO:26:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

GCTCCAGACC CCGCTCCTGC GCCAGAGCCT GCCCCTGCGC CAGAACCAGC GCCTGCGCCG    60

(2) INFORMATION FOR SEQ ID NO:27:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Gly Ser Gly Ala Gly Ala Gly Ser Gly Ala Gly Ala Gly Ser Gly Ala
1               5                   10                  15

Gly Ala Gly Ser Gly Ala Ala
            20

(2) INFORMATION FOR SEQ ID NO:28:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GGCTATGGAG CTGGCGCTGG CTCAGGTGCT GGAGCAGGAA GCGGAGCGGG TGCCA         55

(2) INFORMATION FOR SEQ ID NO:29:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

AGCTTGGCAC CCGCTCCGCT TCCTGCTCCA GCACCTGAGC CAGCGCCAGC GCCAGCTCCA         60

TAGCCTGCA         69

(2) INFORMATION FOR SEQ ID NO:30:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Ala Gly Tyr Gly Ala Gly Ala Gly Ser Gly Ala Gly Ala Gly Ser Gly
1               5                   10                  15

Ala Gly Ala (2) INFORMATION FOR SEQ ID NO:31:

(i) SEQUENCE CHARACTERISTICS:
        (A) LENGTH: 1177 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

```
Asp Pro Val Val Leu Gln Arg Arg Asp Trp Glu Asn Pro Gly Val Thr
1               5                   10                  15

Gln Leu Asn Arg Leu Ala Ala His Pro Pro Phe Ala Ser Asp Pro Met
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Ala Gly Tyr Gly Ala Gly
65                  70                  75                  80

Ala Gly Ser Gly Ala Gly Ala Gly Ser Gly Ala Gly Ala Gly Ser Gly
            85                  90                  95

Ala Gly Ala Gly Ser Gly Ala Gly Ala Gly Ser Gly Ala Gly Ala Gly
            100                 105                 110

Ser Gly Ala Gly Ala Gly Ser Gly Ala Gly Ala Gly Ser Gly Ala Gly
        115                 120                 125

Ala Gly Ser Gly Ala Ala Gly Tyr Gly Ala Gly Ala Gly Ser Gly Ala
    130                 135                 140

Gly Ala Gly Ser Gly Ala Gly Ala Gly Ser Gly Ala Gly Ala Gly Ser
145                 150                 155                 160

Gly Ala Gly Ala Gly Ser Gly Ala Gly Ala Gly Ser Gly Ala Gly Ala
            165                 170                 175

Gly Ser Gly Ala Gly Ala Gly Ser Gly Ala Gly Ala Gly Ser Gly Ala
            180                 185                 190

Ala Gly Tyr Gly Ala Gly Ala Gly Ser Gly Ala Gly Ala Gly Ser Gly
        195                 200                 205

Ala Gly Ala Gly Ser Gly Ala Gly Ala Gly Ser Gly Ala Gly Ala Gly
    210                 215                 220

Ser Gly Ala Gly Ala Gly Ser Gly Ala Gly Ala Gly Ser Gly Ala Gly
225                 230                 235                 240

Ala Gly Ser Gly Ala Gly Ala Gly Ser Gly Ala Ala Gly Tyr Gly Ala
            245                 250                 255

Gly Ala Gly Ser Gly Ala Gly Ala Gly Ser Gly Ala Gly Ala Gly Ser
            260                 265                 270

Gly Ala Gly Ala Gly Ser Gly Ala Gly Ala Gly Ser Gly Ala Gly Ala
        275                 280                 285

Gly Ser Gly Ala Gly Ala Gly Ser Gly Ala Gly Ala Gly Ser Gly Ala
    290                 295                 300

Gly Ala Gly Ser Gly Ala Ala Gly Tyr Gly Ala Gly Ala Gly Ser Gly
305                 310                 315                 320

Ala Gly Ala Gly Ser Gly Ala Gly Ala Gly Ser Gly Ala Gly Ala Gly
            325                 330                 335

Ser Gly Ala Gly Ala Gly Ser Gly Ala Gly Ala Gly Ser Gly Ala Gly
            340                 345                 350

Ala Gly Ser Gly Ala Gly Ala Gly Ser Gly Ala Gly Ala Gly Ser Gly
        355                 360                 365

Ala Ala Gly Tyr Gly Ala Gly Ala Gly Ser Gly Ala Gly Ala Gly Ser
    370                 375                 380

Gly Ala Gly Ala Gly Ser Gly Ala Gly Ala Gly Ser Gly Ala Gly Ala
385                 390                 395                 400
```

-continued

```
Gly Ser Gly Ala Gly Ala Gly Ser Gly Ala Gly Ala
        405                 410                 415
Gly Ala Gly Ser Gly Ala Gly Ala Gly Ser Gly Ala Ala Gly Tyr Gly
        420                 425                 430
Ala Gly Ala Gly Ser Gly Ala Gly Ala Gly Ser Gly Ala Gly Ala Gly
        435                 440                 445
Ser Gly Ala Gly Ala Gly Ser Gly Ala Gly Ala Gly Ser Gly Ala Gly
        450                 455                 460
Ala Gly Ser Gly Ala Gly Ala Gly Ser Gly Ala Gly Ala Gly Ser Gly
465                 470                 475                 480
Ala Gly Ala Gly Ser Gly Ala Ala Gly Tyr Gly Ala Gly Ala Gly Ser
                485                 490                 495
Gly Ala Gly Ala Gly Ser Gly Ala Gly Ala Gly Ser Gly Ala Gly Ala
        500                 505                 510
Gly Ser Gly Ala Gly Ala Gly Ser Gly Ala Gly Ala Gly Ser Gly Ala
        515                 520                 525
Gly Ala Gly Ser Gly Ala Gly Ala Gly Ser Gly Ala Gly Ala Gly Ser
        530                 535                 540
Gly Ala Ala Gly Tyr Gly Ala Gly Ala Gly Ser Gly Ala Gly Ala Gly
545                 550                 555                 560
Ser Gly Ala Gly Ala Gly Ser Gly Ala Gly Ala Gly Ser Gly Ala Gly
                565                 570                 575
Ala Gly Ser Gly Ala Gly Ala Gly Ser Gly Ala Gly Ala Gly Ser Gly
        580                 585                 590
Ala Gly Ala Gly Ser Gly Ala Gly Ala Gly Ser Gly Ala Ala Gly Tyr
        595                 600                 605
Gly Ala Gly Ala Gly Ser Gly Ala Gly Ala Gly Ser Gly Ala Gly Ala
        610                 615                 620
Gly Ser Gly Ala Gly Ala Gly Ser Gly Ala Gly Ala Gly Ser Gly Ala
625                 630                 635                 640
Gly Ala Gly Ser Gly Ala Gly Ala Gly Ser Gly Ala Gly Ala Gly Ser
                645                 650                 655
Gly Ala Gly Ala Gly Ser Gly Ala Ala Gly Tyr Gly Ala Gly Ala Gly
        660                 665                 670
Ser Gly Ala Gly Ala Gly Ser Gly Ala Gly Ala Gly Ser Gly Ala Gly
        675                 680                 685
Ala Gly Ser Gly Ala Gly Ala Gly Ser Gly Ala Gly Ala Gly Ser Gly
        690                 695                 700
Ala Gly Ala Gly Ser Gly Ala Gly Ala Gly Ser Gly Ala Gly Ala Gly
705                 710                 715                 720
Ser Gly Ala Ala Gly Tyr Gly Ala Gly Ala Gly Ser Gly Ala Gly Ala
                725                 730                 735
Gly Ser Gly Ala Gly Ala Gly Ser Gly Ala Gly Ala Gly Ser Gly Ala
        740                 745                 750
Gly Ala Gly Ser Gly Ala Gly Ala Gly Ser Gly Ala Gly Ala Gly Ser
        755                 760                 765
Gly Ala Gly Ala Gly Ser Gly Ala Gly Ala Gly Ser Gly Ala Ala Gly
        770                 775                 780
Tyr Gly Ala Gly Ala Gly Ser Gly Ala Gly Ala Gly Ser Gly Ala Gly
785                 790                 795                 800
Ala Gly Ser Gly Ala Gly Ala Gly Ser Gly Ala Gly Ala Gly Ser Gly
                805                 810                 815
Ala Gly Ala Gly Ser Gly Ala Gly Ala Gly Ser Gly Ala Gly Ala Gly
```

```
                        820                 825                 830
Ser Gly Ala Gly Ala Gly Ser Gly Ala Ala Gly Tyr Gly Ala Gly Ala
                835                 840                 845
Gly Ser Gly Ala Gly Ala Gly Ser Gly Ala Gly Ala Gly Ser Gly Ala
850                 855                 860
Gly Ala Gly Ser Gly Ala Gly Ala Gly Ser Gly Ala Gly Ala Gly Ser
865                 870                 875                 880
Gly Ala Gly Ala Gly Ser Gly Ala Gly Ala Gly Ser Gly Ala Gly Ala
                885                 890                 895
Gly Ser Gly Ala Ala Gly Tyr Gly Ala Gly Ala Gly Ser Gly Ala Gly
                900                 905                 910
Ala Gly Ser Gly Ala Gly Ala Gly Ser Gly Ala Gly Ala Gly Ser Gly
            915                 920                 925
Ala Gly Ala Gly Ser Gly Ala Gly Ala Gly Ser Gly Ala Gly Ala Gly
            930                 935                 940
Ser Gly Ala Gly Ala Gly Ser Gly Ala Gly Ala Gly Ser Gly Ala Ala
945                 950                 955                 960
Gly Tyr Gly Ala Gly Ala Gly Ser Gly Ala Gly Ala Gly Ser Gly Ala
                965                 970                 975
Gly Ala Gly Ser Gly Ala Gly Ala Gly Ser Gly Ala Gly Ala Gly Ser
                980                 985                 990
Gly Ala Gly Ala Gly Ser Gly Ala Gly Ala Gly Ser Gly Ala Gly Ala
                995                 1000                1005
Gly Ser Gly Ala Gly Ala Gly Ser Gly Ala Ala Gly Tyr Gly Ala Gly
            1010                1015                1020
Ala Gly Ser Gly Ala Gly Ala Gly Ser Gly Ala Gly Ala Gly Ser Gly
1025                1030                1035                1040
Ala Gly Ala Gly Ser Gly Ala Gly Ala Gly Ser Gly Ala Gly Ala Gly
                1045                1050                1055
Ser Gly Ala Gly Ala Gly Ser Gly Ala Gly Ala Gly Ser Gly Ala Gly
                1060                1065                1070
Ala Gly Ser Gly Ala Ala Gly Tyr Gly Ala Gly Ala Gly Ser Gly Ala
            1075                1080                1085
Gly Ala Gly Ser Gly Ala Gly Ala Gly Ser Gly Ala Gly Ala Gly Ser
1090                1095                1100
Gly Ala Gly Ala Gly Ser Gly Ala Gly Ala Gly Ser Gly Ala Gly Ala
1105                1110                1115                1120
Gly Ser Gly Ala Gly Ala Gly Ser Gly Ala Gly Ala Gly Ser Gly Ala
                1125                1130                1135
Ala Gly Tyr Gly Ala Gly Ala Gly Ser Gly Ala Gly Ala Gly Ser Gly
            1140                1145                1150
Ala Gly Ala Met Asp Pro Gly Arg Tyr Gln Leu Ser Ala Gly Arg Tyr
            1155                1160                1165
His Tyr Gln Leu Val Trp Cys Gln Lys
            1170                1175

(2) INFORMATION FOR SEQ ID NO:32:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:32:

GTGACTGGCC GTGGTGATAG CCCGGCTAGC GCTGCA                                36

(2) INFORMATION FOR SEQ ID NO:33:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

GCGCTAGCCG GGCTATCACC ACGGCCAGTC ACTGCA                                36

(2) INFORMATION FOR SEQ ID NO:34:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

GGTGCCGGCA GCGGTGCAGG AGCCGGTTCT GGAGCTGGCG CGGGCTCTGG CGCGGGCGCA      60

GGATCCGGCG CAGGCGCTGG TTCTGGCGCA GGGGCAGGCT CTGGCGCAGG AGCGGGGTCT     120

GGAGCTGCAG TGACTGGCCG TGGTGATAGC CCGGCTAGCG CTGCAGGCTA TGGAGCTGGC     180

GCTGGCTCAG GTGCTGGAGC AGGAAGCGGA GCGGGTGCC                            219

(2) INFORMATION FOR SEQ ID NO:35:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

Gly Ala Gly Ser Gly Ala Gly Ala Gly Ser Gly Ala Gly Ala Gly Ser
1               5                   10                  15

Gly Ala Gly Ala Gly Ser Gly Ala Gly Ala Gly Ser Gly Ala Gly Ala
            20                  25                  30

Gly Ser Gly Ala Gly Ala Gly Ser Gly Ala Ala Val Thr Gly Arg Gly
        35                  40                  45

Asp Ser Pro Ala Ser Ala Ala Gly Tyr Gly Ala Gly Ala Gly Ser Gly
    50                  55                  60

Ala Gly Ala Gly Ser Gly Ala Gly
65                  70

(2) INFORMATION FOR SEQ ID NO:36:

(i) SEQUENCE CHARACTERISTICS:
        (A) LENGTH: 1038 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
                20                  25                  30

Met Gly Ala Gly Ser Gly Ala Gly Ala Gly Ser Gly Ala Gly Ala Gly
            35                  40                  45

Ser Gly Ala Gly Ala Gly Ser Gly Ala Gly Ala Gly Ser Gly Ala Gly
        50                  55                  60

Ala Gly Ser Gly Ala Gly Ala Gly Ser Gly Ala Ala Val Thr Gly Arg
65                  70                  75                  80

Gly Asp Ser Pro Ala Ser Ala Ala Gly Tyr Gly Ala Gly Ala Gly Ser
                85                  90                  95

Gly Ala Gly Ala Gly Ser Gly Ala Gly Ala Gly Ser Gly Ala Gly Ala
            100                 105                 110

Gly Ser Gly Ala Gly Ala Gly Ser Gly Ala Gly Ala Gly Ser Gly Ala
        115                 120                 125

Gly Ala Gly Ser Gly Ala Gly Ala Gly Ser Gly Ala Gly Ala Gly Ser
    130                 135                 140

Gly Ala Ala Val Thr Gly Arg Gly Asp Ser Pro Ser Ala Ala Gly Tyr
145                 150                 155                 160

Gly Ala Gly Ala Gly Ser Gly Ala Gly Ala Gly Ser Gly Ala Gly Ala
            165                 170                 175

Gly Ser Gly Ala Gly Ala Gly Ser Gly Ala Gly Ala Gly Ser Gly Ala
        180                 185                 190

Gly Ala Gly Ser Gly Ala Gly Ala Gly Ser Gly Ala Gly Ala Gly Ser
    195                 200                 205

Gly Ala Gly Ala Gly Ser Gly Ala Ala Val Thr Gly Arg Gly Asp Ser
210                 215                 220

Pro Ser Ala Ala Gly Tyr Gly Ala Gly Ala Gly Ser Gly Ala Gly Ala
225                 230                 235                 240

Gly Ser Gly Ala Gly Ala Gly Ser Gly Ala Gly Ala Gly Ser Gly Ala
            245                 250                 255

Gly Ala Gly Ser Gly Ala Gly Ala Gly Ser Gly Ala Gly Ala Gly Ser
        260                 265                 270

Gly Ala Gly Ala Gly Ser Gly Ala Gly Ala Gly Ser Gly Ala Ala Val
    275                 280                 285

Thr Gly Arg Gly Asp Ser Pro Ser Ala Ala Gly Tyr Gly Ala Gly Ala
290                 295                 300

Gly Ser Gly Ala Gly Ala Gly Ser Gly Ala Gly Ala Gly Ser Gly Ala
305                 310                 315                 320

Gly Ala Gly Ser Gly Ala Gly Ala Gly Ser Gly Ala Gly Ala Gly Ser
            325                 330                 335

Gly Ala Gly Ala Gly Ser Gly Ala Gly Ala Gly Ser Gly Ala Gly Ala
        340                 345                 350

Gly Ser Gly Ala Ala Val Thr Gly Arg Gly Asp Ser Pro Ser Ala Ala
    355                 360                 365

Gly Tyr Gly Ala Gly Ala Gly Ser Gly Ala Gly Ala Gly Ser Gly Ala
370                 375                 380

Gly Ala Gly Ser Gly Ala Gly Ala Gly Ser Gly Ala Gly Ala Gly Ser
385                 390                 395                 400

Gly Ala Gly Ala Gly Ser Gly Ala Gly Ala Gly Ser Gly Ala Gly Ala
            405                 410                 415
```

```
Gly Ser Gly Ala Gly Ala Gly Ser Gly Ala Ala Val Thr Gly Arg Gly
                420                 425                 430

Asp Ser Pro Ser Ala Ala Gly Tyr Gly Ala Gly Ala Gly Ser Gly Ala
            435                 440                 445

Gly Ala Gly Ser Gly Ala Gly Ala Gly Ser Gly Ala Gly Ala Gly Ser
        450                 455                 460

Gly Ala Gly Ala Gly Ser Gly Ala Gly Ala Gly Ser Gly Ala Gly Ala
465                 470                 475                 480

Gly Ser Gly Ala Gly Ala Gly Ser Gly Ala Gly Ala Gly Ser Gly Ala
                485                 490                 495

Ala Val Thr Gly Arg Gly Asp Ser Pro Ser Ala Ala Gly Tyr Gly Ala
            500                 505                 510

Gly Ala Gly Ser Gly Ala Gly Ala Gly Ser Gly Ala Gly Ala Gly Ser
        515                 520                 525

Gly Ala Gly Ala Gly Ser Gly Ala Gly Ala Gly Ser Gly Ala Gly Ala
        530                 535                 540

Gly Ser Gly Ala Gly Ala Gly Ser Gly Ala Gly Ala Gly Ser Gly Ala
545                 550                 555                 560

Gly Ala Gly Ser Gly Ala Ala Val Thr Gly Arg Gly Asp Ser Pro Ser
                565                 570                 575

Ala Ala Gly Tyr Gly Ala Gly Ala Gly Ser Gly Ala Gly Ala Gly Ser
            580                 585                 590

Gly Ala Gly Ala Gly Ser Gly Ala Gly Ala Gly Ser Gly Ala Gly Ala
        595                 600                 605

Gly Ser Gly Ala Gly Ala Gly Ser Gly Ala Gly Ala Gly Ser Gly Ala
        610                 615                 620

Gly Ala Gly Ser Gly Ala Gly Ala Gly Ser Gly Ala Ala Val Thr Gly
625                 630                 635                 640

Arg Gly Asp Ser Pro Ser Ala Ala Gly Tyr Gly Ala Gly Ala Gly Ser
                645                 650                 655

Gly Ala Gly Ala Gly Ser Gly Ala Gly Ala Gly Ser Gly Ala Gly Ala
        660                 665                 670

Gly Ser Gly Ala Gly Ala Gly Ser Gly Ala Gly Ala Gly Ser Gly Ala
        675                 680                 685

Gly Ala Gly Ser Gly Ala Gly Ala Gly Ser Gly Ala Gly Ala Gly Ser
        690                 695                 700

Gly Ala Ala Val Thr Gly Arg Gly Asp Ser Pro Ser Ala Ala Gly Tyr
705                 710                 715                 720

Gly Ala Gly Ala Gly Ser Gly Ala Gly Ala Gly Ser Gly Ala Gly Ala
                725                 730                 735

Gly Ser Gly Ala Gly Ala Gly Ser Gly Ala Gly Ala Gly Ser Gly Ala
            740                 745                 750

Gly Ala Gly Ser Gly Ala Gly Ala Gly Ser Gly Ala Gly Ala Gly Ser
        755                 760                 765

Gly Ala Gly Ala Gly Ser Gly Ala Ala Val Thr Gly Arg Gly Asp Ser
        770                 775                 780

Pro Ser Ala Ala Gly Tyr Gly Ala Gly Ala Gly Ser Gly Ala Gly Ala
785                 790                 795                 800

Gly Ser Gly Ala Gly Ala Gly Ser Gly Ala Gly Ala Gly Ser Gly Ala
            805                 810                 815

Gly Ala Gly Ser Gly Ala Gly Ala Gly Ser Gly Ala Gly Ala Gly Ser
        820                 825                 830
```

Gly Ala Gly Ala Gly Ser Gly Ala Gly Ala Gly Ser Gly Ala Ala Val
                835                 840                 845

Thr Gly Arg Gly Asp Ser Pro Ser Ala Ala Gly Tyr Gly Ala Gly Ala
            850                 855                 860

Gly Ser Gly Ala Gly Ala Gly Ser Gly Ala Gly Ala Gly Ser Gly Ala
865                 870                 875                 880

Gly Ala Gly Ser Gly Ala Gly Ser Gly Ala Gly Ala Gly Ser
                885                 890                 895

Gly Ala Gly Ala Gly Ser Gly Ala Gly Ala Gly Ser Gly Ala Gly Ala
                900                 905                 910

Gly Ser Gly Ala Ala Val Thr Gly Arg Gly Asp Ser Pro Ser Ala Ala
                915                 920                 925

Gly Tyr Gly Ala Gly Ala Gly Ser Gly Ala Gly Ala Gly Ser Gly Ala
            930                 935                 940

Gly Ala Gly Ser Gly Ala Gly Ser Gly Ala Gly Ala Gly Ser
945                 950                 955                 960

Gly Ala Gly Ala Gly Ser Gly Ala Gly Ala Gly Ser Gly Ala Gly Ala
                965                 970                 975

Gly Ser Gly Ala Gly Ala Gly Ser Gly Ala Ala Val Thr Gly Arg Gly
                980                 985                 990

Asp Ser Pro Ser Ala Ala Gly Tyr Gly Ala Gly Ala Gly Ser Gly Ala
            995                 1000                1005

Gly Ala Gly Ser Gly Ala Gly Ala Met Asp Pro Gly Arg Tyr Gln Leu
        1010                1015                1020

Ser Ala Gly Arg Tyr His Tyr Gln Leu Trp Val Cys Gln Lys
1025                1030                1035

(2) INFORMATION FOR SEQ ID NO:37:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

GGAGCAGGTT GTGGCGATCC CGGGAAAGGA TGCTGTGTAG CTGGTGCA                48

(2) INFORMATION FOR SEQ ID NO:38:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CCAGCTACAC AGCATCCTTT CCCGGGATCG CCACAACCTG CTCCTGCA                48

(2) INFORMATION FOR SEQ ID NO:39:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

Gly Ala Gly Ser Gly Ala Gly Ala Gly Ser Gly Ala Gly Ala Gly Ser
1               5                  10                  15

Gly Ala Gly Ala Gly Ser Gly Ala Gly Ala Gly Ser Gly Ala Gly Ala
            20                  25                  30

Gly Ser Gly Ala Gly Ala Gly Ser Gly Ala Ala Gly Ala Gly Cys Gly
        35                  40                  45

Asp Pro Gly Lys Gly Cys Cys Val Ala Gly Ala Val Tyr Gly Ala Gly
    50                  55                  60

Ala Gly Ser Gly Ala Gly Ala Gly Ser Gly Ala
65                  70                  75

(2) INFORMATION FOR SEQ ID NO:40:

(i) SEQUENCE CHARACTERISTICS:
        (A) LENGTH: 225 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:40:

```
GGTGCCGGCA GCGGTGCAGG AGCCGGTTCT GGAGCTGGCG CGGGCTCTGG CGCGGGCGCA      60

GGATCCGGCG CAGGCGCTGG TTCTGGCGCA GGGGCAGGCT CTGGCGCAGG AGCGGGGTCT     120

GGAGCTGCAG GAGCAGGTTG TGGCGATCCC GGGAAAGGAT GCTGTGTAGC TGGTGCAGGC     180

TATGGAGCTG GCGCTGGCTC AGGTGCTGGA GCAGGAAGCG GAGCG                    225
```

(2) INFORMATION FOR SEQ ID NO:41:

(i) SEQUENCE CHARACTERISTICS:
        (A) LENGTH: 1332 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

Met Asp Pro Val Val Leu Gln Arg Arg Asp Trp Glu Asn Pro Gly Val
1               5                  10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
        35                  40                  45

Ser Gly Ala Gly Ala Gly Ser Gly Ala Gly Ala Gly Ser Gly Ala Gly
    50                  55                  60

Ala Gly Ser Gly Ala Gly Ala Gly Ser Gly Ala Ala Gly Ala Gly Cys
65                  70                  75                  80

Gly Asp Pro Gly Lys Gly Cys Cys Val Ala Gly Ala Gly Tyr Gly Ala
            85                  90                  95

Gly Ala Gly Ser Gly Ala Gly Ala Gly Ser Gly Ala Gly Ala Gly Ser
            100                 105                 110

Gly Ala Gly Ala Gly Ser Gly Ala Gly Ala Gly Ser Gly Ala Gly Ala
        115                 120                 125

Gly Ser Gly Ala Gly Ala Gly Ser Gly Ala Gly Ala Gly Ser Gly Ala
    130                 135                 140

-continued

```
Gly Ala Gly Ser Gly Ala Ala Gly Ala Gly Cys Gly Asp Pro Gly Lys
145                 150                 155                 160

Gly Cys Cys Val Ala Gly Ala Gly Tyr Gly Ala Gly Ala Gly Ser Gly
                165                 170                 175

Ala Gly Ala Gly Ser Gly Ala Gly Ala Gly Ser Gly Ala Gly Ala Gly
            180                 185                 190

Ser Gly Ala Gly Ala Gly Ser Gly Ala Gly Ala Gly Ser Gly Ala Gly
        195                 200                 205

Ala Gly Ser Gly Ala Gly Ala Gly Ser Gly Ala Gly Ala Gly Ser Gly
    210                 215                 220

Ala Ala Gly Ala Gly Cys Gly Asp Pro Gly Lys Gly Cys Cys Val Ala
225                 230                 235                 240

Gly Ala Gly Tyr Gly Ala Gly Ala Gly Ser Gly Ala Gly Ala Gly Ser
                245                 250                 255

Gly Ala Gly Ala Gly Ser Gly Ala Gly Ala Gly Ser Gly Ala Gly Ala
            260                 265                 270

Gly Ser Gly Ala Gly Ala Gly Ser Gly Ala Gly Ala Gly Ser Gly Ala
        275                 280                 285

Gly Ala Gly Ser Gly Ala Gly Ala Ser Gly Ala Ala Gly Ala Gly
    290                 295                 300

Cys Gly Asp Pro Gly Lys Gly Cys Cys Val Ala Gly Ala Gly Tyr Gly
305                 310                 315                 320

Ala Gly Ala Gly Ser Gly Ala Gly Ala Gly Ser Gly Ala Gly Ala Gly
                325                 330                 335

Ser Gly Ala Gly Ala Gly Ser Gly Ala Gly Ala Gly Ser Gly Ala Gly
            340                 345                 350

Ala Gly Ser Gly Ala Gly Ala Gly Ser Gly Ala Gly Ala Gly Ser Gly
        355                 360                 365

Ala Gly Ala Gly Ser Gly Ala Ala Gly Ala Gly Cys Gly Asp Pro Gly
    370                 375                 380

Lys Gly Cys Cys Val Ala Gly Ala Gly Tyr Gly Ala Gly Ala Gly Ser
385                 390                 395                 400

Gly Ala Gly Ala Gly Ser Gly Ala Gly Ala Gly Ser Gly Ala Gly Ala
                405                 410                 415

Gly Ser Gly Ala Gly Ala Gly Ser Gly Ala Gly Ala Gly Ser Gly Ala
            420                 425                 430

Gly Ala Gly Ser Gly Ala Gly Ala Gly Ser Gly Ala Gly Ala Gly Ser
        435                 440                 445

Gly Ala Ala Gly Ala Gly Cys Gly Asp Pro Gly Lys Gly Cys Cys Val
    450                 455                 460

Ala Gly Ala Gly Tyr Gly Ala Gly Ala Gly Ser Gly Ala Gly Ala Gly
465                 470                 475                 480

Ser Gly Ala Gly Ala Gly Ser Gly Ala Gly Ala Gly Ser Gly Ala Gly
                485                 490                 495

Ala Gly Ser Gly Ala Gly Ala Gly Ser Gly Ala Gly Ala Gly Ser Gly
            500                 505                 510

Ala Gly Ala Gly Ser Gly Ala Gly Ala Gly Ser Gly Ala Ala Gly Ala
        515                 520                 525

Gly Cys Gly Asp Pro Gly Lys Gly Cys Cys Val Ala Gly Ala Gly Tyr
    530                 535                 540

Gly Ala Gly Ala Gly Ser Gly Ala Gly Ala Gly Ser Gly Ala Gly Ala
545                 550                 555                 560

Gly Ser Gly Ala Gly Ala Gly Ser Gly Ala Gly Ala Gly Ser Gly Ala
```

```
                    565                 570                 575
Gly Ala Gly Ser Gly Ala Gly Ala Gly Ser Gly Ala Gly Ala Gly Ser
                580                 585                 590
Gly Ala Gly Ala Gly Ser Gly Ala Ala Gly Ala Gly Cys Gly Asp Pro
                595                 600                 605
Gly Lys Gly Cys Cys Val Ala Gly Ala Gly Tyr Gly Ala Gly Ala Gly
        610                 615                 620
Ser Gly Ala Gly Ala Gly Ser Gly Ala Gly Ala Gly Ser Gly Ala Gly
625                 630                 635                 640
Ala Gly Ser Gly Ala Gly Ala Gly Ser Gly Ala Gly Ala Gly Ser Gly
                645                 650                 655
Ala Gly Ala Gly Ser Gly Ala Gly Ala Gly Ser Gly Ala Gly Ala Gly
                660                 665                 670
Ser Gly Ala Ala Gly Ala Gly Cys Gly Asp Pro Gly Lys Gly Cys Cys
        675                 680                 685
Val Ala Gly Ala Gly Tyr Gly Ala Gly Ala Gly Ser Gly Ala Gly Ala
        690                 695                 700
Gly Ser Gly Ala Gly Ala Gly Ser Gly Ala Gly Ala Gly Ser Gly Ala
705                 710                 715                 720
Gly Ala Gly Ser Gly Ala Gly Ala Gly Ser Gly Ala Gly Ala Gly Ser
                725                 730                 735
Gly Ala Gly Ala Gly Ser Gly Ala Gly Ala Gly Ser Gly Ala Ala Gly
                740                 745                 750
Ala Gly Cys Gly Asp Pro Gly Lys Gly Cys Cys Val Ala Gly Ala Gly
                755                 760                 765
Tyr Gly Ala Gly Ala Gly Ser Gly Ala Gly Ala Gly Ser Gly Ala Gly
        770                 775                 780
Ala Gly Ser Gly Ala Gly Ala Gly Ser Gly Ala Gly Ala Gly Ser Gly
785                 790                 795                 800
Ala Gly Ala Gly Ser Gly Ala Gly Ala Gly Ser Gly Ala Gly Ala Gly
                805                 810                 815
Ser Gly Ala Gly Ala Gly Ser Gly Ala Ala Gly Ala Gly Cys Gly Asp
                820                 825                 830
Pro Gly Lys Gly Cys Cys Val Ala Gly Ala Gly Tyr Gly Ala Gly Ala
                835                 840                 845
Gly Ser Gly Ala Gly Ala Gly Ser Gly Ala Gly Ala Gly Ser Gly Ala
850                 855                 860
Gly Ala Gly Ser Gly Ala Gly Ala Gly Ser Gly Ala Gly Ala Gly Ser
865                 870                 875                 880
Gly Ala Gly Ala Gly Ser Gly Ala Gly Ala Gly Ser Gly Ala Gly Ala
                885                 890                 895
Gly Ser Gly Ala Ala Gly Ala Gly Cys Gly Asp Pro Gly Lys Gly Cys
                900                 905                 910
Cys Val Ala Gly Ala Gly Tyr Gly Ala Gly Ala Gly Ser Gly Ala Gly
        915                 920                 925
Ala Gly Ser Gly Ala Gly Ala Gly Ser Gly Ala Gly Ala Gly Ser Gly
        930                 935                 940
Ala Gly Ala Gly Ser Gly Ala Gly Ala Gly Ser Gly Ala Gly Ala Gly
945                 950                 955                 960
Ser Gly Ala Gly Ala Gly Ser Gly Ala Gly Ala Gly Ser Gly Ala Ala
                965                 970                 975
Gly Ala Gly Cys Gly Asp Pro Gly Lys Gly Cys Cys Val Ala Gly Ala
                980                 985                 990
```

```
Gly Tyr Gly Ala Gly Ala Gly Ser Gly Ala Gly Ala Gly Ser Gly Ala
        995                 1000                1005
Gly Ala Gly Ser Gly Ala Gly Ala Gly Ser Gly Ala Gly Ala Gly Ser
    1010                1015                1020
Gly Ala Gly Ala Gly Ser Gly Ala Gly Ala Gly Ser Gly Ala Gly Ala
1025                1030                1035                1040
Gly Ser Gly Ala Gly Ala Gly Ser Gly Ala Ala Gly Ala Gly Cys Gly
            1045                1050                1055
Asp Pro Gly Lys Gly Cys Cys Val Ala Gly Ala Gly Tyr Gly Ala Gly
            1060                1065                1070
Ala Gly Ser Gly Ala Gly Ala Gly Ser Gly Ala Gly Ala Gly Ser Gly
        1075                1080                1085
Ala Gly Ala Gly Ser Gly Ala Gly Ala Gly Ser Gly Ala Gly Ala Gly
        1090                1095                1100
Ser Gly Ala Gly Ala Gly Ser Gly Ala Gly Ala Gly Ser Gly Ala Gly
1105                1110                1115                1120
Ala Gly Ser Gly Ala Ala Gly Ala Gly Cys Gly Asp Pro Gly Lys Gly
            1125                1130                1135
Cys Cys Val Ala Gly Ala Gly Tyr Gly Ala Gly Ala Gly Ser Gly Ala
            1140                1145                1150
Gly Ala Gly Ser Gly Ala Gly Ala Gly Ser Gly Ala Gly Ala Gly Ser
        1155                1160                1165
Gly Ala Gly Ala Gly Ser Gly Ala Gly Ala Gly Ser Gly Ala Gly Ala
        1170                1175                1180
Gly Ser Gly Ala Gly Ala Gly Ser Gly Ala Gly Ala Gly Ser Gly Ala
1185                1190                1195                1200
Ala Gly Ala Gly Cys Gly Asp Pro Gly Lys Gly Cys Cys Val Ala Gly
            1205                1210                1215
Ala Gly Tyr Gly Ala Gly Ala Gly Ser Gly Ala Gly Ala Gly Ser Gly
            1220                1225                1230
Ala Gly Ala Gly Ser Gly Ala Gly Ala Gly Ser Gly Ala Gly Ala Gly
        1235                1240                1245
Ser Gly Ala Gly Ala Gly Ser Gly Ala Gly Ala Gly Ser Gly Ala Gly
    1250                1255                1260
Ala Gly Ser Gly Ala Gly Ala Gly Ser Gly Ala Ala Gly Ala Gly Cys
1265                1270                1275                1280
Gly Asp Pro Gly Lys Gly Cys Cys Val Ala Gly Ala Gly Tyr Gly Ala
            1285                1290                1295
Gly Ala Gly Ser Gly Ala Gly Ala Gly Ser Gly Ala Gly Ala Met Asp
            1300                1305                1310
Pro Gly Arg Tyr Gln Leu Ser Ala Gly Arg Tyr His Tyr Gln Leu Val
        1315                1320                1325
Trp Cys Gln Lys
    1330

(2) INFORMATION FOR SEQ ID NO:42:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:
```

GTATGTGAAC CCGGGTATAT CGGTAGCCGT TGCGATGCA        39

(2) INFORMATION FOR SEQ ID NO:43:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

TCGCAACGGC TACCGATATA CCCGGGTTCA CATACTGCA        39

(2) INFORMATION FOR SEQ ID NO:44:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

Gly Ala Gly Ser Gly Ala Gly Ala Gly Ser Gly Ala Gly Ala Gly Ser
1               5                  10                  15

Gly Ala Gly Ala Gly Ser Gly Ala Gly Ala Gly Ser Gly Ala Gly Ala
            20                  25                  30

Gly Ser Gly Ala Gly Ala Gly Ser Gly Ala Ala Val Cys Glu Pro Gly
        35                  40                  45

Tyr Ile Gly Ser Arg Cys Asp Ala Gly Tyr Gly Ala Gly Ala Gly Ser
    50                  55                  60

Gly Ala Gly Ala Gly Ser Gly Ala
65                  70

(2) INFORMATION FOR SEQ ID NO:45:

(i) SEQUENCE CHARACTERISTICS:
        (A) LENGTH: 216 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:45:

GGTGCCGGCA GCGGTGCAGG AGCCGGTTCT GGAGCTGGCG CGGGCTCTGG CGCGGGCGCA        60

GGATCCGGCG CAGGCGCTGG TTCTGGCGCA GGGGCAGGCT CTGGCGCAGG AGCGGGGTCT       120

GGAGCTGCAG TATGTGAACC CGGGTATATC GGTAGCCGTT GCGATGCAGG CTATGGAGCT       180

GGCGCTGGCT CAGGTGCTGG AGCAGGAAGC GGAGCG                                 216

(2) INFORMATION FOR SEQ ID NO:46:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:46:

-continued

CTGTGTGTTA GCGAACCC                                                    18

(2) INFORMATION FOR SEQ ID NO:47:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

GGGTTCGCTA ACACACAGTG CA                                               22

(2) INFORMATION FOR SEQ ID NO:48:

(i) SEQUENCE CHARACTERISTICS:
        (A) LENGTH: 784 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
        35                  40                  45

Ser Gly Ala Gly Ala Gly Ser Gly Ala Gly Ala Gly Ser Gly Ala Gly
    50                  55                  60

Ala Gly Ser Gly Ala Gly Ala Gly Ser Gly Ala Ala Val Cys Glu Pro
65                  70                  75                  80

Gly Tyr Ile Gly Ser Arg Cys Asp Ala Gly Tyr Gly Ala Gly Ala Gly
                85                  90                  95

Ser Gly Ala Gly Ala Gly Ser Gly Ala Gly Ala Gly Ser Gly Ala Gly
            100                 105                 110

Ala Gly Ser Gly Ala Gly Ala Gly Ser Gly Ala Gly Ala Gly Ser Gly
        115                 120                 125

Ala Gly Ala Gly Ser Gly Ala Gly Ala Gly Ser Gly Ala Gly Ala Gly
    130                 135                 140

Ser Gly Ala Ala Val Cys Glu Pro Gly Tyr Ile Gly Ser Arg Cys Asp
145                 150                 155                 160

Ala Gly Tyr Gly Ala Gly Ala Gly Ser Gly Ala Gly Ala Gly Ser Gly
                165                 170                 175

Ala Gly Ala Gly Ser Gly Ala Gly Ala Gly Ser Gly Ala Gly Ala Gly
            180                 185                 190

Ser Gly Ala Gly Ala Gly Ser Gly Ala Gly Ala Gly Ser Gly Ala Gly
        195                 200                 205

Ala Gly Ser Gly Ala Gly Ala Gly Ser Gly Ala Ala Val Cys Glu Pro
    210                 215                 220

Gly Tyr Ile Gly Ser Arg Cys Asp Ala Gly Tyr Gly Ala Gly Ala Gly
225                 230                 235                 240

Ser Gly Ala Gly Ala Gly Ser Gly Ala Gly Ala Gly Ser Gly Ala Gly
                245                 250                 255
```

-continued

```
Ala Gly Ser Gly Ala Gly Ala Gly Ser Gly Ala Gly Ala Gly Ser Gly
            260                 265                 270

Ala Gly Ala Gly Ser Gly Ala Gly Ala Gly Ser Gly Ala Gly Ala Gly
        275                 280                 285

Ser Gly Ala Ala Val Cys Glu Pro Gly Tyr Ile Gly Ser Arg Cys Asp
    290                 295                 300

Ala Gly Tyr Gly Ala Gly Ala Gly Ser Gly Ala Gly Ala Gly Ser Gly
305                 310                 315                 320

Ala Gly Ala Gly Ser Gly Ala Gly Ala Gly Ser Gly Ala Gly Ala Gly
                325                 330                 335

Ser Gly Ala Gly Ala Gly Ser Gly Ala Gly Ala Gly Ser Gly Ala Gly
            340                 345                 350

Ala Gly Ser Gly Ala Gly Ala Gly Ser Gly Ala Ala Val Cys Glu Pro
        355                 360                 365

Gly Tyr Ile Gly Ser Arg Cys Asp Ala Gly Tyr Gly Ala Gly Ala Gly
    370                 375                 380

Ser Gly Ala Gly Ala Gly Ser Gly Ala Gly Ala Gly Ser Gly Ala Gly
385                 390                 395                 400

Ala Gly Ser Gly Ala Gly Ala Gly Ser Gly Ala Gly Ala Gly Ser Gly
                405                 410                 415

Ala Gly Ala Gly Ser Gly Ala Gly Ala Gly Ser Gly Ala Gly Ala Gly
            420                 425                 430

Ser Gly Ala Ala Val Cys Glu Pro Gly Tyr Ile Gly Ser Arg Cys Asp
        435                 440                 445

Ala Gly Tyr Gly Ala Gly Ala Gly Ser Gly Ala Gly Ala Gly Ser Gly
    450                 455                 460

Ala Gly Ala Gly Ser Gly Ala Gly Ala Gly Ser Gly Ala Gly Ala Gly
465                 470                 475                 480

Ser Gly Ala Gly Ala Gly Ser Gly Ala Gly Ala Gly Ser Gly Ala Gly
                485                 490                 495

Ala Gly Ser Gly Ala Gly Ala Gly Ser Gly Ala Ala Val Cys Glu Pro
            500                 505                 510

Gly Tyr Ile Gly Ser Arg Cys Asp Ala Gly Tyr Gly Ala Gly Ala Gly
        515                 520                 525

Ser Gly Ala Gly Ala Gly Ser Gly Ala Gly Ala Gly Ser Gly Ala Gly
    530                 535                 540

Ala Gly Ser Gly Ala Gly Ala Gly Ser Gly Ala Gly Ala Gly Ser Gly
545                 550                 555                 560

Ala Gly Ala Gly Ser Gly Ala Gly Ala Gly Ser Gly Ala Gly Ala Gly
                565                 570                 575

Ser Gly Ala Ala Val Cys Glu Pro Gly Tyr Ile Gly Ser Arg Cys Asp
            580                 585                 590

Ala Gly Tyr Gly Ala Gly Ala Gly Ser Gly Ala Gly Ala Gly Ser Gly
        595                 600                 605

Ala Gly Ala Gly Ser Gly Ala Gly Ala Gly Ser Gly Ala Gly Ala Gly
    610                 615                 620

Ser Gly Ala Gly Ala Gly Ser Gly Ala Gly Ala Gly Ser Gly Ala Gly
625                 630                 635                 640

Ala Gly Ser Gly Ala Gly Ala Gly Ser Gly Ala Ala Val Cys Glu Pro
                645                 650                 655

Gly Tyr Ile Gly Ser Arg Cys Asp Ala Gly Tyr Gly Ala Gly Ala Gly
            660                 665                 670

Ser Gly Ala Gly Ala Gly Ser Gly Ala Gly Ala Gly Ser Gly Ala Gly
```

```
            675                 680                 685
Ala Gly Ser Gly Ala Gly Ala Gly Ser Gly Ala Gly Gly
            690                 695                 700

Ala Gly Ala Gly Ser Gly Ala Gly Ala Gly Ser Gly Ala Gly Ala Gly
705                 710                 715                 720

Ser Gly Ala Ala Val Cys Glu Pro Gly Tyr Ile Gly Ser Arg Cys Asp
                725                 730                 735

Ala Gly Tyr Gly Ala Gly Ala Gly Ser Gly Ala Gly Ala Gly Ser Gly
                740                 745                 750

Ala Gly Ala Met Asp Pro Gly Arg Tyr Gln Leu Ser Ala Gly Arg Tyr
                755                 760                 765

Gln Leu Ser Ala Gly Arg Tyr His Tyr Gln Leu Val Trp Cys Gln Lys
770                 775                 780
```

(2) INFORMATION FOR SEQ ID NO:49:

(i) SEQUENCE CHARACTERISTICS:
        (A) LENGTH: 649 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
            35                  40                  45

Ser Gly Ala Gly Ala Gly Ser Gly Ala Gly Ala Gly Ser Gly Ala Gly
            50                  55                  60

Ala Gly Ser Gly Ala Gly Ala Gly Ser Gly Ala Ala Leu Cys Val Ser
65                  70                  75                  80

Glu Pro Gly Tyr Ile Gly Ser Arg Cys Asp Ala Gly Tyr Gly Ala Gly
                85                  90                  95

Ala Gly Ser Gly Ala Gly Ala Gly Ser Gly Ala Gly Ala Gly Ser Gly
                100                 105                 110

Ala Gly Ala Gly Ser Gly Ala Gly Ala Gly Ser Gly Ala Gly Ala Gly
                115                 120                 125

Ser Gly Ala Gly Ala Gly Ser Gly Ala Gly Ala Gly Ser Gly Ala Gly
                130                 135                 140

Ala Gly Ser Gly Ala Ala Leu Cys Val Ser Glu Pro Gly Tyr Ile Gly
145                 150                 155                 160

Ser Arg Cys Asp Ala Gly Tyr Gly Ala Gly Ala Gly Ser Gly Ala Gly
                165                 170                 175

Ala Gly Ser Gly Ala Gly Ala Gly Ser Gly Ala Gly Ala Gly Ser Gly
                180                 185                 190

Ala Gly Ala Gly Ser Gly Ala Gly Ala Gly Ser Gly Ala Gly Ala Gly
                195                 200                 205

Ser Gly Ala Gly Ala Gly Ser Gly Ala Gly Ala Gly Ser Gly Ala Ala
                210                 215                 220

Leu Cys Val Ser Glu Pro Gly Tyr Ile Gly Ser Arg Cys Asp Ala Gly
225                 230                 235                 240

Tyr Gly Ala Gly Ala Gly Ser Gly Ala Gly Ala Gly Ser Gly Ala Gly
```

```
                          245                 250                 255
Ala Gly Ser Gly Ala Gly Ala Gly Ser Gly Ala Gly Ala Gly Ser Gly
                260                 265                 270
Ala Gly Ala Gly Ser Gly Ala Gly Ser Gly Ala Gly Ala Gly
                275                 280                 285
Ser Gly Ala Gly Ala Gly Ser Gly Ala Ala Leu Cys Val Ser Glu Pro
                290                 295                 300
Gly Tyr Ile Gly Ser Arg Cys Asp Ala Gly Tyr Gly Ala Gly Ala Gly
305                 310                 315                 320
Ser Gly Ala Gly Ala Gly Ser Gly Ala Gly Ser Gly Ala Gly
                325                 330                 335
Ala Gly Ser Gly Ala Gly Ala Gly Ser Gly Ala Gly Ala Gly Ser Gly
                340                 345                 350
Ala Gly Ala Gly Ser Gly Ala Gly Ala Gly Ser Gly Ala Gly Ala Gly
                355                 360                 365
Ser Gly Ala Ala Leu Cys Val Ser Glu Pro Gly Tyr Ile Gly Ser Arg
                370                 375                 380
Cys Asp Ala Gly Tyr Gly Ala Gly Ala Gly Ser Gly Ala Gly Ala Gly
385                 390                 395                 400
Ser Gly Ala Gly Ala Gly Ser Gly Ala Gly Ala Gly Ser Gly Ala Gly
                405                 410                 415
Ala Gly Ser Gly Ala Gly Ala Gly Ser Gly Ala Gly Ala Gly Ser Gly
                420                 425                 430
Ala Gly Ala Gly Ser Gly Ala Gly Ala Gly Ser Gly Ala Ala Leu Cys
                435                 440                 445
Val Ser Glu Pro Gly Tyr Ile Gly Ser Arg Cys Asp Ala Gly Tyr Gly
                450                 455                 460
Ala Gly Ala Gly Ser Gly Ala Gly Ala Gly Ser Gly Ala Gly Ala Gly
465                 470                 475                 480
Ser Gly Ala Gly Ala Gly Ser Gly Ala Gly Ala Gly Ser Gly Ala Gly
                485                 490                 495
Ala Gly Ser Gly Ala Gly Ala Gly Ser Gly Ala Gly Ala Gly Ser Gly
                500                 505                 510
Ala Gly Ala Gly Ser Gly Ala Ala Leu Cys Val Ser Glu Pro Gly Tyr
                515                 520                 525
Ile Gly Ser Arg Cys Asp Ala Gly Tyr Gly Ala Gly Ala Gly Ser Gly
                530                 535                 540
Ala Gly Ala Gly Ser Gly Ala Gly Ala Gly Ser Gly Ala Gly Ala Gly
545                 550                 555                 560
Ser Gly Ala Gly Ala Gly Ser Gly Ala Gly Ala Gly Ser Gly Ala Gly
                565                 570                 575
Ala Gly Ser Gly Ala Gly Ala Gly Ser Gly Ala Gly Ala Gly Ser Gly
                580                 585                 590
Ala Ala Leu Cys Val Ser Glu Pro Gly Tyr Ile Gly Ser Arg Cys Asp
                595                 600                 605
Ala Gly Tyr Gly Ala Gly Ala Gly Ser Gly Ala Gly Ala Gly Ser Gly
                610                 615                 620
Ala Gly Ala Met Asp Pro Gly Arg Tyr Gln Leu Ser Ala Gly Arg Tyr
625                 630                 635                 640
His Tyr Gln Leu Val Trp Cys Gln Lys
                645

(2) INFORMATION FOR SEQ ID NO:50:
```

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:50:

Gly Leu Pro Gly Pro Lys Gly Asp Arg Gly Asp Ala Gly Pro Lys Gly
1               5                  10                  15

Ala Asp Gly Ser Pro
            20

(2) INFORMATION FOR SEQ ID NO:51:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:51:

AATTCGGTGC CCCTGGTCCG CCTGGTCCGC CTGGTCCACC GGGTCCTCCG GGGGCTC             57

(2) INFORMATION FOR SEQ ID NO:52:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:52:

AATTCGGTGC CCCTGGTCCG CCTGGTCCGC CTGGTCCACC GGGTCCTCCG GGGGCTC             57

(2) INFORMATION FOR SEQ ID NO:53:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:53:

CCGGGTCCTC CAGGACCGCC AGGTCCGCCT GGTCCCCC                                  38

(2) INFORMATION FOR SEQ ID NO:54:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:54:

GGGTCCTGCA GGTCCAGTAG GTAGCCCCCG GTGCCATGTG TGCGCATCGA TATC                54

(2) INFORMATION FOR SEQ ID NO:55:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

GGGTCCTGCA GGTCCAGTAG GTAGCCCCCG GTGCCATGTG TGCGCATCGA TATC        54

(2) INFORMATION FOR SEQ ID NO:56:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

TCGAGATATC GATGCGCACA CAT        23

(2) INFORMATION FOR SEQ ID NO:57:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Pro
            20                  25                  30

Ala Gly Pro Val Gly Ser Pro Gly Ala
        35                  40

(2) INFORMATION FOR SEQ ID NO:58:

(i) SEQUENCE CHARACTERISTICS:
        (A) LENGTH: 123 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:58:

GGTGCCCCTG GTCCGCCTGG TCCGCCTGGT CCACCGGGTC CTCCGGGGGC TCCGGGTCCT        60

CCAGGACCGC CAGGTCCGCC TGGTCCCCCG GGTCCTGCAG GTCCAGTAGG TAGCCCCGGT       120

GCC                                                                    123

(2) INFORMATION FOR SEQ ID NO:59:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

CCGGGACTGC CAGGCCCGAA AGGCGATCGT GGCGACGCCG GTCCTAAAGG CGCAGATGGC        60

AGC        63

(2) INFORMATION FOR SEQ ID NO:60:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

CCGGGCTGCC ATCTGCGCCT TTAGGACCGG CGTCGCCACG ATCGCCTTTC GGGCCTGGCA        60

GTCCCGG        67

(2) INFORMATION FOR SEQ ID NO:61:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

```
Gly Ala Pro Gly Pro Pro Gly Pro Pro Gly Pro Pro Gly Pro Pro Gly
1               5                  10                  15

Ala Pro Gly Pro Pro Gly Pro Pro Gly Pro Pro Gly Pro Pro Gly Leu
            20                  25                  30

Pro Gly Pro Lys Gly Asp Arg Gly Asp Ala Gly Pro Arg Gly Ala Asp
        35                  40                  45

Gly Ser Pro Gly Pro Ala Gly Pro Val Gly Ser Pro Gly Ala
    50                  55                  60
```

(2) INFORMATION FOR SEQ ID NO:62:

(i) SEQUENCE CHARACTERISTICS:
        (A) LENGTH: 186 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:62:

GGTGCCCCTG GTCCGCCTGG TCCGCCTGGT CCACCGGGTC CTCCGGGGGC TCCGGGTCCT        60

CCAGGACCGC CAGGTCCGCC TGGTCCCCCG GGACTGCCAG GCCCGAAAGG CGATCGTGGC       120

GACGCCGGTC CTAAAGGCGC AGATGGCAGC CCGGGTCCTG CAGGTCCAGT AGGTAGCCCC       180

GGTGCC       186

(2) INFORMATION FOR SEQ ID NO:63:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

```
Gly Ala Gly Ser Gly Ala Gly Ala Gly Ser Gly Ala Gly Ala Gly Ser
1               5                   10                  15

Gly Ala Gly Ala Gly Ser Gly Ala Gly Ala Gly Ser Gly Ala Gly Ala
                20                  25                  30

Gly Ser Gly Ala Gly Ala Gly Ser Gly Ala Ala Leu Cys Val Ser Glu
            35                  40                  45

Pro Gly Tyr Ile Gly Ser Arg Cys Asp Ala Gly Tyr Gly Ala Gly Ala
        50                  55                  60

Gly Ser Gly Ala Gly Ala Gly Ser Gly Ala
65                  70
```

(2) INFORMATION FOR SEQ ID NO:64:

(i) SEQUENCE CHARACTERISTICS:
        (A) LENGTH: 222 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:64:

```
GGTGCCGGCA GCGGTGCAGG AGCCGGTTCT GGAGCTGGCG CGGGCTCTGG CGCGGGCGCA      60

GGATCCGGCG CAGGCGCTGG TTCTGGCGCA GGGGCAGGCT CTGGCGCAGG AGCGGGGTCT     120

GGAGCTGCAC TGTGTGTTAG CGAACCCGGG TATATCGGTA GCCGTTGCGA TGCAGGCTAT     180

GGAGCTGGCG CTGGCTCAGG TGCTGGAGCA GGAAGCGGAG CG                        222
```

(2) INFORMATION FOR SEQ ID NO:65:

(i) SEQUENCE CHARACTERISTICS:
        (A) LENGTH: 408 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:65:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
                20                  25                  30

Met Gly Ala Pro Gly Pro Pro Gly Pro Pro Gly Pro Pro Gly Pro Pro
            35                  40                  45

Gly Ala Pro Gly Pro Pro Gly Pro Pro Gly Pro Pro Gly Pro Pro Gly
        50                  55                  60

Pro Ala Gly Pro Val Gly Ser Pro Gly Ala Pro Gly Pro Pro Gly Pro
65                  70                  75                  80

Pro Gly Pro Pro Gly Pro Pro Gly Ala Pro Gly Pro Pro Gly Pro Pro
                85                  90                  95

Gly Pro Pro Gly Pro Pro Gly Pro Ala Gly Pro Val Gly Ser Pro Gly
            100                 105                 110

Ala Pro Gly Pro Pro Gly Pro Pro Gly Pro Pro Gly Pro Pro Gly Ala
        115                 120                 125

Pro Gly Pro Pro Gly Pro Pro Gly Pro Pro Gly Pro Pro Gly Pro Ala
            130                 135                 140
```

```
Gly Pro Val Gly Ser Pro Gly Ala Pro Gly Pro Gly Pro Pro Gly
145                 150                 155                 160

Pro Pro Gly Pro Pro Gly Ala Pro Gly Pro Pro Gly Pro Pro Gly Pro
                165                 170                 175

Pro Gly Pro Pro Gly Pro Ala Gly Pro Val Gly Ser Pro Gly Ala Pro
            180                 185                 190

Gly Pro Pro Gly Pro Pro Gly Pro Pro Gly Pro Pro Gly Ala Pro Gly
        195                 200                 205

Pro Pro Gly Pro Pro Gly Pro Pro Gly Pro Pro Gly Pro Ala Gly Pro
    210                 215                 220

Val Gly Ser Pro Gly Ala Pro Gly Pro Pro Gly Pro Pro Gly Pro Pro
225                 230                 235                 240

Gly Pro Pro Gly Ala Pro Gly Pro Pro Gly Pro Pro Gly Pro Pro Gly
                245                 250                 255

Pro Pro Gly Pro Ala Gly Pro Val Gly Ser Pro Gly Ala Pro Gly Pro
            260                 265                 270

Pro Gly Pro Pro Gly Pro Pro Gly Pro Pro Gly Ala Pro Gly Pro Pro
        275                 280                 285

Gly Pro Pro Gly Pro Pro Gly Pro Pro Gly Pro Ala Gly Pro Val Gly
    290                 295                 300

Ser Pro Gly Ala Pro Gly Pro Pro Gly Pro Pro Gly Pro Pro Gly Pro
305                 310                 315                 320

Pro Gly Ala Pro Gly Pro Pro Gly Pro Pro Gly Pro Pro Gly Pro Pro
                325                 330                 335

Gly Pro Ala Gly Pro Val Gly Ser Pro Gly Ala Pro Gly Pro Pro Gly
            340                 345                 350

Pro Pro Gly Pro Pro Gly Pro Pro Gly Ala Pro Gly Pro Pro Gly Pro
        355                 360                 365

Pro Gly Pro Pro Gly Pro Pro Gly Pro Ala Gly Pro Val Gly Ser Pro
    370                 375                 380

Gly Ala Met Cys Ala His Arg Tyr Gln Leu Ser Ala Gly Arg Tyr His
385                 390                 395                 400

Tyr Gln Leu Val Trp Cys Gln Lys
                405

(2) INFORMATION FOR SEQ ID NO:66:

(i) SEQUENCE CHARACTERISTICS:
        (A) LENGTH: 357 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:66:

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
                20                  25                  30

Met Gly Ala Pro Gly Pro Pro Gly Pro Pro Gly Pro Pro Gly Pro Pro
            35                  40                  45

Gly Ala Pro Gly Pro Pro Gly Pro Pro Gly Pro Pro Gly Pro Pro Gly
        50                  55                  60

Leu Pro Gly Pro Lys Gly Asp Arg Gly Asp Ala Gly Pro Lys Gly Ala
65                  70                  75                  80
```

Asp Gly Ser Pro Gly Pro Ala Gly Pro Val Gly Ser Pro Gly Ala Pro
                85                  90                  95

Gly Pro Pro Gly Pro Pro Gly Pro Pro Gly Pro Pro Gly Ala Pro Gly
            100                 105                 110

Pro Pro Gly Pro Pro Gly Pro Pro Gly Pro Pro Gly Leu Pro Gly Pro
            115                 120                 125

Lys Gly Asp Arg Gly Asp Ala Gly Pro Lys Gly Ala Asp Gly Ser Pro
            130                 135                 140

Gly Pro Ala Gly Pro Val Gly Ser Pro Gly Ala Pro Gly Pro Pro Gly
145                 150                 155                 160

Pro Pro Gly Pro Pro Gly Pro Pro Gly Ala Pro Gly Pro Pro Gly Pro
            165                 170                 175

Pro Gly Pro Pro Gly Pro Pro Gly Leu Pro Gly Pro Lys Gly Asp Arg
            180                 185                 190

Gly Asp Ala Gly Pro Lys Gly Ala Asp Gly Ser Pro Gly Pro Ala Gly
            195                 200                 205

Pro Val Gly Ser Pro Gly Ala Pro Gly Pro Pro Gly Pro Pro Gly Pro
            210                 215                 220

Pro Gly Pro Pro Gly Ala Pro Gly Pro Pro Gly Pro Pro Gly Pro Pro
225                 230                 235                 240

Gly Pro Pro Gly Leu Pro Gly Pro Lys Gly Asp Arg Gly Asp Ala Gly
            245                 250                 255

Pro Lys Gly Ala Asp Gly Ser Pro Gly Pro Ala Gly Pro Val Gly Ser
            260                 265                 270

Pro Gly Ala Pro Gly Pro Pro Gly Pro Pro Gly Pro Pro Gly Pro Pro
            275                 280                 285

Gly Ala Pro Gly Pro Pro Gly Pro Pro Gly Pro Pro Gly Pro Pro Gly
290                 295                 300

Leu Pro Gly Pro Lys Gly Asp Arg Gly Asp Ala Gly Pro Lys Gly Ala
305                 310                 315                 320

Asp Gly Ser Pro Gly Pro Ala Gly Pro Val Gly Ser Pro Gly Ala Met
            325                 330                 335

Cys Ala His Arg Tyr Gln Leu Ser Ala Gly Arg Tyr His Tyr Gln Leu
            340                 345                 350

Val Trp Cys Gln Lys
            355

(2) INFORMATION FOR SEQ ID NO:67:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

Gly Arg Gly Gly Ser Phe Gly Gly Ser Ser Tyr Gly Gly Gly Ser
1               5                   10                  15

(2) INFORMATION FOR SEQ ID NO:68:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

GTGCCGGATG CTCGAGCGCT AAACTGAAAT TGGCAGAAGC GAAGCTTATG CATG           54

(2) INFORMATION FOR SEQ ID NO:69:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:69:

CATAAGCTTC GCTTCTGCCA ATTTCAGTTT AGCGCTCGAG CATCCG                   46

(2) INFORMATION FOR SEQ ID NO:70:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:70:

AGCTTGAGCT GGCAGAAGCT AAACTGAAGC TGGCGGAAGC TAAGCGAGCT CATGCA        56

(2) INFORMATION FOR SEQ ID NO:71:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:71:

TGAGCTCGCT TAGCTTCCGC CAGCTTCAGT TTAGCTTCTG CCAGCTCA                 48

(2) INFORMATION FOR SEQ ID NO:72:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:72:

AATTGCTAAG CTGGAGCTGG CAGAAGCTAA ACTGAAGTTA GCGGAAGCTA AACTGGAGCT    60

(2) INFORMATION FOR SEQ ID NO:73:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:73:

CCAGTTTAGC TTCCGCTAAC TTCAGTTTAG CTTCTGCCAG CTCCAGCTTA GC    52

(2) INFORMATION FOR SEQ ID NO:74:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:74:

CGCGGAAGCC AAACTGAAGC TGGCGGAGGC TAAATTGGAA CTGGCCGAGG CTAAATGCAT    60

G    61

(2) INFORMATION FOR SEQ ID NO:75:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:75:

CATTTTAGCC TCGGCCAGTT CCAATTTAGC CTCCGCCAGC TTCAGTTTGG CTTCCGCGAG    60

CT    62

(2) INFORMATION FOR SEQ ID NO:76:

(i) SEQUENCE CHARACTERISTICS:
        (A) LENGTH: 132 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:76:

GCTAAACTGA AATTGGCAGA AGCGAAGCTT GAGCTGGCAG AAGCTAAACT GAAGTTAGCG    60

GAAGCTAAAC TGGAGCTCGC GGAAGCCAAA CTGAAGCTGG CGGAGGCTAA ATTGGAACTG    120

GCCGAGGCTA AA    132

(2) INFORMATION FOR SEQ ID NO:77:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

Ala Lys Leu Lys Leu Ala Glu Ala Lys Leu Glu Leu Ala Glu Ala Lys
1               5                   10                  15

Leu Lys Leu Ala Glu Ala Lys Leu Glu Leu Ala Glu Ala Lys Leu Lys
                20                  25                  30

Leu Ala Glu Ala Lys Leu Glu Leu Ala Glu Ala Lys
            35                  40

(2) INFORMATION FOR SEQ ID NO:78:

(i) SEQUENCE CHARACTERISTICS:
        (A) LENGTH: 572 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:78:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
                20                  25                  30

Met Gly Ala Gly Cys Ser Ser Ala Lys Leu Lys Leu Ala Glu Ala Lys
            35                  40                  45

Leu Glu Leu Ala Glu Ala Lys Leu Lys Leu Ala Glu Ala Lys Leu Glu
50                  55                  60

Leu Ala Glu Ala Lys Leu Lys Leu Ala Glu Ala Lys Leu Glu Leu Ala
65                  70                  75                  80

Glu Ala Lys Leu Lys Leu Ala Glu Ala Lys Leu Glu Leu Ala Glu Ala
                85                  90                  95

Lys Leu Lys Leu Ala Glu Ala Lys Leu Glu Leu Ala Glu Ala Lys Leu
            100                 105                 110

Lys Leu Ala Glu Ala Lys Leu Glu Leu Ala Glu Ala Lys Leu Lys Leu
            115                 120                 125

Ala Glu Ala Lys Leu Glu Leu Ala Glu Ala Lys Leu Lys Leu Ala Glu
            130                 135                 140

Ala Lys Leu Glu Leu Ala Glu Ala Lys Leu Lys Leu Ala Glu Ala Lys
145                 150                 155                 160

Leu Glu Leu Ala Glu Ala Lys Leu Lys Leu Ala Glu Ala Lys Leu Glu
                165                 170                 175

Leu Ala Glu Ala Lys Leu Lys Leu Ala Glu Ala Lys Leu Glu Leu Ala
            180                 185                 190

Glu Ala Lys Leu Lys Leu Ala Glu Ala Lys Leu Glu Leu Ala Glu Ala
            195                 200                 205

Lys Leu Lys Leu Ala Glu Ala Lys Leu Glu Leu Ala Glu Ala Lys Leu
            210                 215                 220

Lys Leu Ala Glu Ala Lys Leu Glu Leu Ala Glu Ala Lys Leu Lys Leu
225                 230                 235                 240

Ala Glu Ala Lys Leu Glu Leu Ala Glu Ala Lys Leu Lys Leu Ala Glu
                245                 250                 255

Ala Lys Leu Glu Leu Ala Glu Ala Lys Leu Lys Leu Ala Glu Ala Lys
            260                 265                 270

Leu Glu Leu Ala Glu Ala Lys Leu Lys Leu Ala Glu Ala Lys Leu Glu
            275                 280                 285

Leu Ala Glu Ala Lys Leu Lys Leu Ala Glu Ala Lys Leu Glu Leu Ala
            290                 295                 300

Glu Ala Lys Leu Lys Leu Ala Glu Ala Lys Leu Glu Leu Ala Glu Ala
305                 310                 315                 320

Lys Leu Lys Leu Ala Glu Ala Lys Leu Glu Leu Ala Glu Ala Lys Leu
                325                 330                 335

Lys Leu Ala Glu Ala Lys Leu Glu Leu Ala Glu Ala Lys Leu Lys Leu
            340                 345                 350

Ala Glu Ala Lys Leu Glu Leu Ala Glu Ala Lys Leu Lys Leu Ala Glu
```

```
                    355                 360                 365
Ala Lys Leu Glu Leu Ala Glu Ala Lys Leu Lys Leu Ala Glu Ala Lys
                370                 375                 380

Leu Glu Leu Ala Glu Ala Lys Leu Lys Leu Ala Glu Ala Lys Leu Glu
385                 390                 395                 400

Leu Ala Glu Ala Lys Leu Lys Leu Ala Glu Ala Lys Leu Glu Leu Ala
                405                 410                 415

Glu Ala Lys Leu Lys Leu Ala Glu Ala Lys Leu Glu Leu Ala Glu Ala
                420                 425                 430

Lys Leu Lys Leu Ala Glu Ala Lys Leu Glu Leu Ala Glu Ala Lys Leu
                435                 440                 445

Lys Leu Ala Glu Ala Lys Leu Glu Leu Ala Glu Ala Lys Leu Lys Leu
                450                 455                 460

Ala Glu Ala Lys Leu Glu Leu Ala Glu Ala Lys Leu Lys Leu Ala Glu
465                 470                 475                 480

Ala Lys Leu Glu Leu Ala Glu Ala Lys Leu Lys Leu Ala Glu Ala Lys
                485                 490                 495

Leu Glu Leu Ala Glu Ala Lys Leu Lys Leu Ala Glu Ala Lys Leu Glu
                500                 505                 510

Leu Ala Glu Ala Lys Leu Lys Leu Ala Glu Ala Lys Leu Glu Leu Ala
                515                 520                 525

Glu Ala Lys Leu Lys Leu Ala Glu Ala Lys Leu Glu Leu Ala Glu Ala
                530                 535                 540

Lys Met His Ala His Pro Pro Gly Ser Ile Ser Asp Gln Leu Ser Ala
545                 550                 555                 560

Gly Arg Tyr His Tyr Gln Leu Val Trp Cys Gln Lys
                565                 570
```

(2) INFORMATION FOR SEQ ID NO:79:

(i) SEQUENCE CHARACTERISTICS:
        (A) LENGTH: 740 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:79:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
                20                  25                  30

Met Gly Ala Gly Cys Ser Ser Ala Leu Lys Leu Ala Glu Ala Lys
                35                  40                  45

Leu Glu Leu Ala Glu Ala Lys Lys Leu Ala Glu Ala Lys Leu Glu
                50                  55                  60

Leu Ala Glu Ala Lys Leu Lys Leu Ala Glu Ala Lys Leu Glu Leu Ala
65                  70                  75                  80

Glu Ala Lys Leu Lys Leu Ala Glu Ala Lys Leu Glu Leu Ala Glu Ala
                85                  90                  95

Lys Leu Lys Leu Ala Glu Ala Lys Leu Glu Leu Ala Glu Ala Lys Leu
                100                 105                 110

Lys Leu Ala Glu Ala Lys Leu Glu Leu Ala Glu Ala Lys Leu Lys Leu
                115                 120                 125

Ala Glu Ala Lys Leu Glu Leu Ala Glu Ala Lys Leu Lys Leu Ala Glu
```

-continued

```
            130                 135                 140
Ala Lys Leu Glu Leu Ala Glu Ala Lys Leu Ala Glu Ala Lys
145                 150                 155                 160
Leu Glu Leu Ala Glu Ala Lys Leu Lys Leu Ala Glu Ala Lys Leu Glu
                165                 170                 175
Leu Ala Glu Ala Lys Leu Lys Leu Ala Glu Ala Lys Leu Glu Leu Ala
            180                 185                 190
Glu Ala Lys Leu Lys Leu Ala Glu Ala Lys Leu Glu Leu Ala Glu Ala
                195                 200                 205
Lys Leu Lys Leu Ala Glu Ala Lys Leu Glu Leu Ala Glu Ala Lys Leu
            210                 215                 220
Lys Leu Ala Glu Ala Lys Leu Glu Leu Ala Glu Ala Lys Leu Lys Leu
225                 230                 235                 240
Ala Glu Ala Lys Leu Glu Leu Ala Glu Ala Lys Leu Lys Leu Ala Glu
                245                 250                 255
Ala Lys Leu Glu Leu Ala Glu Ala Lys Leu Lys Leu Ala Glu Ala Lys
            260                 265                 270
Leu Glu Leu Ala Glu Ala Lys Leu Lys Leu Ala Glu Ala Lys Leu Glu
            275                 280                 285
Leu Ala Glu Ala Lys Leu Lys Leu Ala Glu Ala Lys Leu Glu Leu Ala
            290                 295                 300
Glu Ala Lys Leu Lys Leu Ala Glu Ala Lys Leu Glu Leu Ala Glu Ala
305                 310                 315                 320
Lys Leu Lys Leu Ala Glu Ala Lys Leu Glu Leu Ala Glu Ala Lys Leu
                325                 330                 335
Lys Leu Ala Glu Ala Lys Leu Glu Leu Ala Glu Ala Lys Leu Lys Leu
            340                 345                 350
Ala Glu Ala Lys Leu Glu Leu Ala Glu Ala Lys Leu Lys Leu Ala Glu
            355                 360                 365
Ala Lys Leu Glu Leu Ala Glu Ala Lys Leu Lys Leu Ala Glu Ala Lys
            370                 375                 380
Leu Glu Leu Ala Glu Ala Lys Leu Lys Leu Ala Glu Ala Lys Leu Glu
385                 390                 395                 400
Leu Ala Glu Ala Lys Leu Lys Leu Ala Glu Ala Lys Leu Glu Leu Ala
                405                 410                 415
Glu Ala Lys Leu Lys Leu Ala Glu Ala Lys Leu Glu Leu Ala Glu Ala
            420                 425                 430
Lys Leu Lys Leu Ala Glu Ala Lys Leu Glu Leu Ala Glu Ala Lys Leu
            435                 440                 445
Lys Leu Ala Glu Ala Lys Leu Glu Leu Ala Glu Ala Lys Leu Lys Leu
            450                 455                 460
Ala Glu Ala Lys Leu Glu Leu Ala Glu Ala Lys Leu Lys Leu Ala Glu
465                 470                 475                 480
Ala Lys Leu Glu Leu Ala Glu Ala Lys Leu Lys Leu Ala Glu Ala Lys
            485                 490                 495
Leu Glu Leu Ala Glu Ala Lys Leu Lys Leu Ala Glu Ala Lys Leu Glu
            500                 505                 510
Leu Ala Glu Ala Lys Leu Lys Leu Ala Glu Ala Lys Leu Glu Leu Ala
            515                 520                 525
Glu Ala Lys Leu Lys Leu Ala Glu Ala Lys Leu Glu Leu Ala Glu Ala
            530                 535                 540
Lys Leu Lys Leu Ala Glu Ala Lys Leu Glu Leu Ala Glu Ala Lys Leu
545                 550                 555                 560
```

Lys Leu Ala Glu Ala Lys Leu Glu Leu Ala Glu Ala Lys Leu Lys Leu
                565                 570                 575

Ala Glu Ala Lys Leu Glu Leu Ala Glu Ala Lys Leu Lys Leu Ala Glu
            580                 585                 590

Ala Lys Leu Glu Leu Ala Glu Ala Lys Leu Lys Leu Ala Glu Ala Lys
        595                 600                 605

Leu Glu Leu Ala Glu Ala Lys Leu Lys Leu Ala Glu Ala Lys Leu Glu
    610                 615                 620

Leu Ala Glu Ala Lys Leu Lys Leu Ala Glu Ala Lys Leu Glu Leu Ala
625                 630                 635                 640

Glu Ala Lys Leu Lys Leu Ala Glu Ala Lys Leu Glu Leu Ala Glu Ala
                645                 650                 655

Lys Leu Lys Leu Ala Glu Ala Lys Leu Glu Leu Ala Glu Ala Lys Leu
            660                 665                 670

Lys Leu Ala Glu Ala Lys Leu Glu Leu Ala Glu Ala Lys Leu Lys Leu
        675                 680                 685

Ala Glu Ala Lys Leu Glu Leu Ala Glu Ala Lys Leu Lys Leu Ala Glu
    690                 695                 700

Ala Lys Leu Glu Leu Ala Glu Ala Lys Met His Ala His Pro Pro Gly
705                 710                 715                 720

Ser Ile Ser Asp Gln Leu Ser Ala Gly Arg Tyr His Tyr Gln Leu Val
                725                 730                 735

Trp Cys Gln Lys
            740

(2) INFORMATION FOR SEQ ID NO:80:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:80:

GGCCGAGGGC CGTGGTGGCA GCTTCGGTGG ATCCTCTTAT GGTGGCGGTT CTGCTAAAAT    60

GCA                                                                 63

(2) INFORMATION FOR SEQ ID NO:81:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:81:

TTTTAGCAGA ACCGCCACCA TAAGAGGATC CACCGAAGCT GCCACCACGG CCCTC         55

(2) INFORMATION FOR SEQ ID NO:82:

(i) SEQUENCE CHARACTERISTICS:
        (A) LENGTH: 175 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:82:

```
GCTAAACTGA ATTGGCAGAA GCGAAGCTGG AGCTGGCAGA AGCTAAACTG AAGTTAGCGG      60

AAGCTAAACT GGAGCTCGCG GAAGCCAAAC TGAAGCTGGC GGAGGCTAAA TTGGAACTGG     120

CCGAGGGCCG TGGTGGCAGC TTCGGTGGAT CCTCTTATGG TGGCGGTTCT GCTAA          175
```

(2) INFORMATION FOR SEQ ID NO:83:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:83:

```
Ala Lys Leu Lys Leu Ala Glu Ala Lys Leu Glu Leu Ala Glu Ala Lys
 1               5                  10                  15

Leu Lys Leu Ala Glu Ala Lys Leu Glu Leu Ala Glu Ala Lys Leu Lys
                20                  25                  30

Leu Ala Glu Ala Lys Leu Glu Leu Ala Glu Gly Arg Gly Gly Ser Phe
                35                  40                  45

Gly Gly Ser Ser Tyr Gly Gly Gly Ser Ala Lys
 50                  55
```

(2) INFORMATION FOR SEQ ID NO:84:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:84:

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
                20                  25                  30

Met Gly Ala Gly Cys Ser Ser Ala Lys Leu Lys Leu Ala Glu Ala Lys
                35                  40                  45

Leu Glu Leu Ala Glu Ala Lys Leu Lys Leu Ala Glu Ala Lys Leu Glu
                50                  55                  60

Leu Ala Glu Ala Lys Leu Lys Leu Ala Glu Ala Lys Leu Glu Leu Ala
 65                  70                  75                  80

Glu Gly Arg Gly Gly Ser Phe Gly Gly Ser Ser Tyr Gly Gly Gly Ser
                85                  90                  95

Ala Lys Met His Ala His Pro Pro Gly Ser Ile Ser Asp Gln Leu Ser
                100                 105                 110

Ala Gly Arg Tyr His Tyr Gln Leu Val Trp Cys Gln Lys
                115                 120                 125
```

(2) INFORMATION FOR SEQ ID NO:85:

(i) SEQUENCE CHARACTERISTICS:
        (A) LENGTH: 5 amino acids
        (B) TYPE: amino acid
        (C) STRANDEDNESS: single
        (D) TOPOLOGY: linear

```
        (ii) MOLECULE TYPE: peptide (xi) SEQUENCE DESCRIPTION: SEQ ID NO:85:

Tyr Ile Gly Ser Arg
1               5

(2) INFORMATION FOR SEQ ID NO:86:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:86:

Pro Glu Tyr Asp Gly Glu Thr Arg Ala Lys Val Lys Ala His Ser Gln
1               5                  10                  15

Thr His Arg Val Asp Thr Leu Arg Tyr
            20                  25

(2) INFORMATION FOR SEQ ID NO:87:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:87:

Thr Arg Lys Trp Ala Ala His Val Glu Gln Leu Arg Ala Tyr Glu Gly
1               5                  10                  15

Thr Val Glu Trp Arg Tyr
            20

(2) INFORMATION FOR SEQ ID NO:88:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:88:

Asp Pro Gly Lys
1

(2) INFORMATION FOR SEQ ID NO:89:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:89:

Asn Pro Gly Cys
1
```

(2) INFORMATION FOR SEQ ID NO:90:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:90:

Arg Pro Gly Glu
1

(2) INFORMATION FOR SEQ ID NO:91:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:91:

Gly Ala Gly Asp
1

(2) INFORMATION FOR SEQ ID NO:92:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:92:

Gly Ala Gly Cys
1

(2) INFORMATION FOR SEQ ID NO:93:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:93:

Gly Ala Gly Lys
1

(2) INFORMATION FOR SEQ ID NO:94:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:94:

Gly Glu Gly Val Pro
1              5

(2) INFORMATION FOR SEQ ID NO:95:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:95:

```
Gly Cys Gly Val Pro
1               5
```

(2) INFORMATION FOR SEQ ID NO:96:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:96:

```
Gly Lys Gly Val Pro
1               5
```

(2) INFORMATION FOR SEQ ID NO:97:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:97:

```
Gly Ala Gly Ala Gly Gln Gly Ala Gly Ala Gly Gln Gly Ala Gly Ala
1               5                   10                  15
Gly Gln Gly Ala Gly Ala Gly Gln Gly Ala Gly Ala Gly Gln Gly Ala
            20                  25                  30
Gly Ala Gly Gln
        35
```

(2) INFORMATION FOR SEQ ID NO:98:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:98:

```
Gly Ala Gly Ala Gly Ser Gly Ala Gly Ala Gly Ser Gly Ala Gly Ala
1               5                   10                  15
Gly Ser Gly Ala Gly Ala Gly Ser Gly Ala Gly Ala Gly Ser Gly Ala
            20                  25                  30
Gly Ala Gly Ser Gly Ala Gly Ala Gly Ser Gly Ala Gly Ala Gly Ser
        35                  40                  45
Gly Ala Gly Ala Gly Ser Gly Ala Ala Gly Tyr Gly Ala Gly Tyr
    50                  55                  60
```

(2) INFORMATION FOR SEQ ID NO:99:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:99:

```
Gly Ala Gly Ala Gly Ser Gly Ala Gly Ala Gly Ser Gly Ala Gly Ala
1               5                   10                  15
Gly Ser Gly Ala Gly Ala Gly Ser Gly Ala Gly Ala Gly Ser Gly Ala
                20                  25                  30
Gly Ala Gly Ser Gly Ala Gly Ala Gly Ser Gly Ala Gly Ala Gly Ser
                35                  40                  45
Gly Ala Gly Ala Gly Ser Gly Ala Ala Ala Arg Pro Ser Thr Lys Arg
                50                  55                  60
Gln Arg Phe Arg His Arg Asn Arg Lys Gly Tyr Arg Ser Gln Arg Gly
65                  70                  75                  80
His Ser Arg Gly Arg Asn Gln Asn Ser Arg Arg Pro Ser Ala Ala Gly
                85                  90                  95
Tyr
```

(2) INFORMATION FOR SEQ ID NO:100:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:100:

```
Trp Pro Cys Asp Asx Val Pro Glx Cys Arg Ile Glu Arg Cys Pro Ile
1               5                   10                  15
Xaa Xaa Xaa Trp Xaa Xaa Xaa His Pro Leu Ala Ser Glu Arg Glu Thr
                20                  25                  30
Ile Ile Ile His Pro Leu Ala Ser Ile Ile Ile Pro Arg Ser Xaa Xaa
                35                  40                  45
Tyr Xaa Xaa Asx Gly Ala Gly Ala Gly Ser Gly Ala Gly Ala Gly Ser
                50                  55                  60
Gly Ala Gly Ala Gly Ser Gly Ala Gly Ala Gly Ser Gly Ala Gly Ala
65                  70                  75                  80
Gly Ser Gly Ala Gly Ala Gly Ser Gly Ala Gly Ala Gly Ser Gly Ala
                85                  90                  95
Gly Ala Gly Ser Gly Ala Gly Ala Gly Ser Gly Ala Ala Ala Arg Pro
                100                 105                 110
Ser Leu Thr Lys Lys Gln Arg Phe Arg His Arg Asn Arg Lys Gly Tyr
                115                 120                 125
Arg Ser Gln Arg Gly His Ser Arg Arg Pro Ser Ala Gly Tyr
                130                 135                 140
```

(2) INFORMATION FOR SEQ ID NO:101:

(i) SEQUENCE CHARACTERISTICS:
        (A) LENGTH: 83 amino acids
        (B) TYPE: amino acid

```
              (C) STRANDEDNESS: single
              (D) TOPOLOGY: linear (ii) MOLECULE TYPE: peptide (xi) SEQUENCE DESCRIPTION: SEQ ID NO:101:

Gly Ala Gly Ala Gly Ser Gly Ala Gly Ala Gly Ser Gly Ala Gly Ala
1               5                  10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
            35                  40                  45

Gly Ala Gly Ala Gly Ser Gly Met Val Thr Gly Arg Gly Asp Ser Pro
        50                  55                  60

Ala Ser Ala Ala Val Cys Glu Pro Gly Tyr Ile Gly Ser Arg Cys Asp
65                  70                  75                  80

Ala Gly Tyr (2) INFORMATION FOR SEQ ID NO:102:

(i) SEQUENCE CHARACTERISTICS:
              (A) LENGTH: 86 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:102:

Gly Ala Gly Ala Gly Ser Gly Ala Gly Ala Gly Ser Gly Ala Gly Ala
1               5                  10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
            35                  40                  45

Gly Ala Gly Ala Gly Ser Gly Ala Ala Val Thr Gly Arg Gly Asp Ser
        50                  55                  60

Pro Ala Ser Ala Ala Leu Cys Val Ser Glu Pro Gly Tyr Ile Gly Ser
65                  70                  75                  80

Arg Cys Asp Ala Gly Tyr
            85

(2) INFORMATION FOR SEQ ID NO:103:

(i) SEQUENCE CHARACTERISTICS:
              (A) LENGTH: 123 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:103:

Gly Ala Gly Ala Gly Ser Gly Ala Gly Ala Gly Ser Gly Ala Gly Ala
1               5                  10                  15

Gly Ser Gly Ala Gly Ala Gly Ser Gly Ala Gly Ala Gly Ser Gly Val
            20                  25                  30

Gly Val Gly Gly Val Gly Val Gly Val Gly Val Val Gly Gly Val Gly
            35                  40                  45

Val Gly Gly Val Gly Val Gly Gly Val Gly Val Gly Val Gly Gly Val
        50                  55                  60
```

Gly Gly Val Gly Val Gly Gly Ala Gly Ala Gly Ala Gly Ala
65                  70                  75                  80

Gly Ser Gly Ala Gly Ala Gly Ser Gly Ala Gly Ala Gly Ser Gly Ala
            85                  90                  95

Gly Ala Gly Ser Gly Ala Gly Ala Gly Ser Gly Ala Ala Val Thr Gly
            100                 105                 110

Arg Gly Asp Ser Pro Ala Ser Ala Ala Gly Tyr
            115                 120

(2) INFORMATION FOR SEQ ID NO:104:

(i) SEQUENCE CHARACTERISTICS:
        (A) LENGTH: 159 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:104:

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
            35                  40                  45

Gly Val Gly Val Gly Gly Val Gly Val Gly Val Gly Val Gly Gly
            50                  55                  60

Val Gly Val Gly Gly Val Gly Val Gly Gly Val Gly Val Gly Gly Val
65                  70                  75                  80

Gly Val Gly Gly Val Gly Val Gly Gly Ala Gly Ala Gly Ser Gly Ala
            85                  90                  95

Gly Ala Gly Ser Gly Ala Gly Ala Gly Ser Gly Ala Gly Ala Gly Ser
            100                 105                 110

Gly Ala Gly Ala Gly Ser Gly Ala Gly Ala Gly Ser Gly Ala Gly Ala
            115                 120                 125

Gly Ser Gly Ala Gly Ala Gly Ser Gly Ala Gly Ala Gly Ser Gly Ala
            130                 135                 140

Ala Val Thr Gly Arg Gly Asp Ser Pro Ala Ser Ala Ala Gly Tyr
145                 150                 155

(2) INFORMATION FOR SEQ ID NO:105:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
            35                  40                  45

Gly Ala Gly Ala Gly Ser Gly Ala Ala Gly Ala Gly Cys Gly Asp Pro

-continued

```
            50                  55                  60
Gly Lys Gly Cys Cys Val Ala Gly Ala Gly Tyr Gly Ala Gly Ala Gly
 65                  70                  75                  80

Ser Gly Ala Gly Ala Gly Ser Gly Ala Gly Ala Gly Ser Gly Ala Gly
                 85                  90                  95

Ala Gly Ser Gly Ala Gly Ala Gly Ser Gly Ala Gly Ala Gly Ser Gly
                100                 105                 110

Ala Gly Ala Gly Ser Gly Ala Gly Ala Gly Ser Gly Ala Gly Ala Gly
                115                 120                 125

Ser Gly Ala Ala Val Thr Gly Arg Gly Asp Ser Pro Ala Ser Ala Ala
    130                 135                 140

Gly Tyr
145

(2) INFORMATION FOR SEQ ID NO:106:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:106:

Gly Ala Pro Gly Pro Pro Gly Pro Pro Gly Pro Pro Gly Pro Pro Gly
 1               5                  10                  15

Ala Pro Gly Pro Pro Gly Pro Pro Gly Pro Pro Gly Pro Ala Val Thr
                20                  25                  30

Gly Arg Gly Asp Ser Pro Ala Ser Ala Ala Gly Pro Val Gly Ser Pro
            35                  40                  45

(2) INFORMATION FOR SEQ ID NO:107:

(i) SEQUENCE CHARACTERISTICS:
        (A) LENGTH: 49 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

Gly Ala Pro Gly Pro Pro Gly Pro Pro Gly Pro Pro Gly Pro Pro Gly
 1               5                  10                  15

Ala Pro Gly Pro Pro Gly Pro Pro Gly Pro Pro Gly Pro Ala Val Cys
                20                  25                  30

Glu Pro Gly Tyr Ile Gly Ser Arg Cys Asp Ala Gly Pro Val Gly Ser
            35                  40                  45

Pro (2) INFORMATION FOR SEQ ID NO:108:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:108:
```

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Ala Ser Cys
                20                  25                  30

Val Ser Glu Pro Gly Tyr Ile Gly Ser Arg Cys Asp Ala Gly Pro Val
        35                  40                  45

Gly Ser Pro
    50

(2) INFORMATION FOR SEQ ID NO:109:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:109:

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Ala Ala Arg
                20                  25                  30

Pro Ser Leu Thr Lys Lys Gln Arg Phe Arg His Arg Asn Arg Lys Gly
        35                  40                  45

Tyr Arg Ser Gln Arg Gly His Ser Arg Gly Arg Asn Gln Asn Ser Arg
    50                  55                  60

Arg Pro Ser Gly Pro Val Gly Ser Pro
65                  70

(2) INFORMATION FOR SEQ ID NO:110:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:110:

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Ala Ala Arg
                20                  25                  30

Pro Ser Leu Thr Lys Lys Gln Arg Phe Arg His Arg Asn Arg Lys Gly
        35                  40                  45

Tyr Arg Ser Gln Arg Gly His Ser Arg Gly Arg Asn Gln Asn Ser Arg
    50                  55                  60

Arg Pro Ser Gly Pro Val Gly Ser Pro
65                  70

(2) INFORMATION FOR SEQ ID NO:111:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:111:

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Leu Pro Gly Pro
            20                  25                  30

Lys Gly Asp Arg Gly Asp Ala Gly Pro Lys Gly Ala Asp Gly Ser Pro
            35                  40                  45

Gly Pro Ala Val Thr Gly Arg Gly Asp Ser Pro Ala Ser Ala Ala Gly
        50                  55                  60

Pro Val Gly Ser Pro
65

(2) INFORMATION FOR SEQ ID NO:112:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:112:

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Leu Pro Gly Pro
            20                  25                  30

Lys Gly Asp Arg Gly Asp Ala Gly Pro Lys Gly Asp Gly Ser Pro Gly
            35                  40                  45

Pro Ala Val Cys Glu Pro Gly Tyr Ile Gly Ser Arg Cys Asp Ala Gly
        50                  55                  60

Pro Val Gly Ser Pro
65

(2) INFORMATION FOR SEQ ID NO:113:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:113:

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Leu Pro Gly Pro
            20                  25                  30

Lys Gly Asp Arg Gly Asp Ala Gly Pro Lys Gly Ala Asp Gly Ser Pro
            35                  40                  45

Gly Pro Ala Leu Cys Val Ser Glu Pro Gly Tyr Ile Gly Ser Arg Cys
        50                  55                  60

Asp Ala Gly Pro Val Gly Ser Pro
65                  70

(2) INFORMATION FOR SEQ ID NO:114:

(i) SEQUENCE CHARACTERISTICS:
        (A) LENGTH: 85 amino acids
        (B) TYPE: amino acid (C) STRANDEDNESS: single
            (D) TOPOLOGY: linear (ii) MOLECULE TYPE: peptide (xi) SEQUENCE DESCRIPTION: SEQ ID NO:114:

Gly Ala Pro Gly Pro Pro Gly Pro Pro Gly Pro Pro Gly Pro Pro Gly
1               5                  10                  15

Ala Pro Gly Pro Pro Gly Pro Pro Gly Pro Pro Gly Pro Pro Gly Leu
                20                  25                  30

Pro Gly Pro Lys Gly Asp Arg Gly Asp Ala Gly Pro Lys Gly Ala Asp
            35                  40                  45

Gly Ser Pro Gly Pro Ala Val Thr Gly Arg Gly Asp Ser Pro Ala Ser
        50                  55                  60

Ala Ala Val Cys Glu Pro Gly Tyr Ile Gly Ser Arg Cys Asp Ala Gly
65                  70                  75                  80

Pro Val Gly Ser Pro
                85

(2) INFORMATION FOR SEQ ID NO:115:

(i) SEQUENCE CHARACTERISTICS:
            (A) LENGTH: 83 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:115:

Gly Ala Pro Gly Pro Pro Gly Pro Pro Gly Pro Pro Gly Pro Pro Gly
1               5                  10                  15

Ala Pro Gly Pro Pro Gly Pro Pro Gly Pro Pro Gly Leu Pro Gly Pro
                20                  25                  30

Lys Gly Asp Arg Gly Asp Ala Gly Pro Lys Gly Ala Asp Gly Ser Gly
            35                  40                  45

Pro Ala Val Thr Gly Arg Gly Asp Ser Pro Ala Ser Ala Ala Leu Cys
        50                  55                  60

Val Ser Glu Pro Gly Tyr Ile Gly Ser Arg Cys Asp Ala Gly Pro Val
65                  70                  75                  80

Gly Ser Pro (2) INFORMATION FOR SEQ ID NO:116:

(i) SEQUENCE CHARACTERISTICS:
            (A) LENGTH: 30 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:116:

Tyr Lys Ala Lys Pro Ser Tyr Pro Pro Thr Tyr Lys Ala Lys Pro Ser
1               5                  10                  15

Tyr Pro Pro Thr Tyr Lys Ala Lys Pro Ser Tyr Pro Pro Thr
                20                  25                  30

(2) INFORMATION FOR SEQ ID NO:117:

(i) SEQUENCE CHARACTERISTICS:
            (A) LENGTH: 92 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:117:

Gly Ala Gly Ala Gly Ser Gly Ala Gly Ala Gly Ser Gly Ala Gly Ala
1               5                  10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Val Thr Tyr Lys Ala Lys Pro
    50                  55                  60

Ser Tyr Pro Pro Thr Tyr Lys Ala Lys Pro Ser Tyr Pro Pro Thr Tyr
65                  70                  75                  80

Lys Ala Lys Pro Ser Tyr Pro Pro Thr Ala Gly Tyr
                85                  90

(2) INFORMATION FOR SEQ ID NO:118:

(i) SEQUENCE CHARACTERISTICS:
           (A) LENGTH: 69 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:118:

Gly Ala Pro Gly Pro Pro Gly Pro Pro Gly Pro Pro Gly Pro Pro Gly
1               5                  10                  15

Ala Pro Gly Pro Pro Gly Pro Pro Gly Pro Pro Gly Pro Pro Thr Tyr
            20                  25                  30

Lys Ala Lys Pro Ser Tyr Pro Pro Thr Tyr Lys Ala Lys Pro Ser Tyr
        35                  40                  45

Pro Pro Thr Tyr Lys Ala Lys Pro Ser Tyr Pro Pro Gly Pro Ala Cys
    50                  55                  60

Pro Val Gly Ser Pro
65

(2) INFORMATION FOR SEQ ID NO:119:

(i) SEQUENCE CHARACTERISTICS:
           (A) LENGTH: 6 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:119:

Gly Ala Gly Ala Gly Ser
1               5
```